(12) United States Patent
Wagner et al.

(10) Patent No.: US 11,642,142 B2
(45) Date of Patent: May 9, 2023

(54) OSTEOTOMY SYSTEMS, DEVICES AND METHODS

(71) Applicant: Paragon 28, Inc., Englewood, CO (US)

(72) Inventors: Pablo Wagner, Santiago (CL); Emilio Wagner, Santiago (CL); John Mullins, Dublin (IE); Laura Zagrocki Brinker, Lone Tree, CO (US)

(73) Assignee: Paragon 28, Inc., Englewood, CO (US)

( * ) Notice: Subject to any disclaimer, the term of this patent is extended or adjusted under 35 U.S.C. 154(b) by 280 days.

(21) Appl. No.: 16/841,317

(22) Filed: Apr. 6, 2020

(65) Prior Publication Data

US 2020/0229828 A1 Jul. 23, 2020

Related U.S. Application Data

(63) Continuation of application No. 15/792,730, filed on Oct. 24, 2017, now Pat. No. 10,610,241.
(Continued)

(51) Int. Cl.
*A61B 17/15* (2006.01)
*A61B 17/88* (2006.01)
(Continued)

(52) U.S. Cl.
CPC ........ *A61B 17/1775* (2016.11); *A61B 17/151* (2013.01); *A61B 17/8061* (2013.01);
(Continued)

(58) Field of Classification Search
CPC .............. A61B 17/151; A61B 17/1775; A61B 17/8061
See application file for complete search history.

(56) References Cited

U.S. PATENT DOCUMENTS

| 5,350,380 A | 9/1994 | Goble |
| 5,352,228 A | 10/1994 | Kummer |

(Continued)

FOREIGN PATENT DOCUMENTS

| EP | 0617927 | 10/1994 |
| EP | 1273271 | 8/2007 |

(Continued)

OTHER PUBLICATIONS

Partial Supplementary European Search Report issued in European Patent Application No. 18777784.2, dated Jan. 14, 2021, 13 pages.
(Continued)

*Primary Examiner* — Christian A Sevilla
(74) *Attorney, Agent, or Firm* — Heslin Rothenberg Farley & Mesiti P.C.; Jacquelyn A. Graff, Esq.

(57) ABSTRACT

Osteotomy systems, devices, and methods for using the osteotomy systems are disclosed. The osteotomy system including an alignment device, at least one k-wire for insertion into the alignment device, and a cut guide with at least one hole for receiving at least one k-wire and a slot for receiving a saw blade. An osteotomy kit including an alignment device, cut guide, and position rotation device. The alignment device, cut guide, position rotation device, and bone plate are also disclosed. Finally, a method for fusing bones using the osteotomy system is also disclosed.

18 Claims, 66 Drawing Sheets

Related U.S. Application Data

(60) Provisional application No. 62/531,176, filed on Jul. 11, 2017, provisional application No. 62/411,768, filed on Oct. 24, 2016.

(51) Int. Cl.
  *A61B 17/17*  (2006.01)
  *A61B 17/80*  (2006.01)
  *A61B 17/16*  (2006.01)
  *A61B 17/56*  (2006.01)

(52) U.S. Cl.
  CPC ...... *A61B 17/8866* (2013.01); *A61B 17/8897* (2013.01); *A61B 17/1682* (2013.01); *A61B 17/8057* (2013.01); *A61B 2017/565* (2013.01)

(56) References Cited

U.S. PATENT DOCUMENTS

| | | |
|---|---|---|
| 5,429,641 A | 7/1995 | Gotfried |
| 5,458,602 A | 10/1995 | Goble |
| 6,342,057 B1 | 1/2002 | Brace |
| 6,454,771 B1* | 9/2002 | Michelson ......... A61B 17/7058 606/76 |
| 6,692,496 B1 | 2/2004 | Wardlaw |
| 7,011,665 B2 | 3/2006 | Null |
| 7,316,687 B2 | 1/2008 | Aikins |
| 7,785,326 B2 | 8/2010 | Green |
| 7,819,877 B2 | 10/2010 | Guzman |
| 8,206,389 B2 | 6/2012 | Huebner |
| 8,231,627 B2 | 7/2012 | Huebner |
| 8,535,355 B2 | 9/2013 | Prasad |
| 9,044,250 B2 | 6/2015 | Olsen et al. |
| 9,161,796 B2 | 10/2015 | Chiodo |
| 9,241,744 B2 | 1/2016 | Blake |
| 9,421,103 B2 | 8/2016 | Jeng et al. |
| 2003/0009217 A1 | 1/2003 | McKernan |
| 2004/0102776 A1 | 5/2004 | Huebner |
| 2004/0102777 A1 | 5/2004 | Huebner |
| 2004/0193165 A1* | 9/2004 | Orbay ................ A61B 17/8095 606/280 |
| 2005/0033301 A1 | 2/2005 | Lombardo |
| 2006/0189996 A1 | 8/2006 | Orbay |
| 2007/0173843 A1 | 7/2007 | Matityahu |
| 2007/0225714 A1 | 9/2007 | Gradl |
| 2007/0239168 A1 | 10/2007 | Kuenzi |
| 2007/0265634 A1 | 11/2007 | Weinstein |
| 2007/0270850 A1 | 11/2007 | Geissler |
| 2008/0015590 A1 | 1/2008 | Sanders |
| 2008/0091197 A1 | 4/2008 | Coughlin |
| 2008/0188852 A1 | 8/2008 | Matityahu |
| 2009/0036931 A1 | 2/2009 | Pech |
| 2009/0088767 A1 | 4/2009 | Leyden |
| 2009/0093849 A1 | 4/2009 | Grabowski |
| 2010/0087824 A1 | 4/2010 | Collazo |
| 2010/0121324 A1 | 5/2010 | Tyber |
| 2010/0179597 A1* | 7/2010 | Henderson ......... A61B 17/7055 606/279 |
| 2011/0046681 A1 | 2/2011 | Prandi et al. |
| 2011/0125200 A1* | 5/2011 | Hanson .................. A61B 90/39 606/86 R |
| 2011/0144647 A1 | 6/2011 | Appenzeller |
| 2011/0144700 A1 | 6/2011 | Konieczynski |
| 2011/0218576 A1 | 9/2011 | Galm |
| 2011/0224734 A1 | 9/2011 | Schelling |
| 2011/0264149 A1 | 10/2011 | Pappalardo |
| 2011/0270319 A1 | 11/2011 | Sheffer |
| 2011/0282397 A1 | 11/2011 | Richter |
| 2012/0078252 A1* | 3/2012 | Huebner ............. A61B 17/808 606/70 |
| 2012/0209268 A1 | 8/2012 | Overes |
| 2012/0271314 A1 | 10/2012 | Stemniski |
| 2012/0303038 A1 | 11/2012 | Durante |
| 2012/0316562 A1 | 12/2012 | Costa |
| 2013/0046311 A1 | 2/2013 | Blake et al. |
| 2013/0150903 A1 | 6/2013 | Vincent |
| 2013/0172942 A1 | 7/2013 | Lewis et al. |
| 2013/0231668 A1 | 9/2013 | Olsen |
| 2014/0066996 A1 | 3/2014 | Price et al. |
| 2014/0107798 A1 | 4/2014 | Jeng et al. |
| 2014/0180348 A1 | 6/2014 | Thoren et al. |
| 2015/0032168 A1 | 1/2015 | Orsak et al. |
| 2015/0150683 A1 | 6/2015 | Donner et al. |
| 2015/0182267 A1 | 7/2015 | Wolf et al. |
| 2015/0245923 A1 | 9/2015 | Abdou |
| 2015/0359580 A1 | 12/2015 | Dacosta et al. |
| 2016/0030064 A1 | 2/2016 | DaCosta et al. |
| 2016/0135858 A1 | 5/2016 | Dacosta et al. |
| 2016/0235414 A1 | 8/2016 | Hatch et al. |
| 2016/0242791 A1 | 8/2016 | Fallin et al. |
| 2016/0310191 A1 | 10/2016 | Seykora |
| 2016/0324552 A1 | 11/2016 | Baker et al. |
| 2016/0354128 A1 | 12/2016 | Jeng |
| 2017/0056031 A1 | 3/2017 | Awtrey et al. |
| 2017/0216043 A1 | 8/2017 | Surma et al. |
| 2018/0242987 A1 | 8/2018 | Lintula et al. |
| 2018/0242988 A1 | 8/2018 | Dacosta et al. |
| 2018/0280069 A1 | 10/2018 | Barmes et al. |
| 2019/0015140 A1 | 1/2019 | Dacosta et al. |
| 2019/0038326 A1 | 2/2019 | Hedgeland et al. |

FOREIGN PATENT DOCUMENTS

| | | |
|---|---|---|
| EP | 2745786 | 6/2014 |
| EP | 3023068 | 5/2016 |
| FR | 3030221 | 6/2016 |
| JP | 04250156 | 9/1992 |
| JP | 2009112954 | 5/2009 |
| WO | 9415556 | 7/1994 |
| WO | 2005089660 | 9/2005 |
| WO | 2009052294 | 4/2009 |
| WO | 2012103335 | 8/2012 |
| WO | 2012106477 | 8/2012 |
| WO | 2013009574 | 1/2013 |
| WO | 2014105750 | 7/2014 |
| WO | 2015094409 | 6/2015 |
| WO | 2015138542 | 9/2015 |
| WO | 2017004221 | 1/2017 |
| WO | 2017011656 | 1/2017 |
| WO | 2018157168 | 8/2018 |
| WO | 2018157170 | 8/2018 |
| WO | 2018183875 | 10/2018 |
| WO | 2019014356 | 1/2019 |

OTHER PUBLICATIONS

Extended European Search Report issued in European Patent Application No. 18757770.5, dated Mar. 9, 2021, 10 pages.
Extended European Search Report issued in European Patent Application No. 18758239.0, dated Apr. 8, 2021, 12 pages.
Extended European Search Report issued in European Patent Application No. 18831633.5, dated Apr. 16, 2021, 10 pages.
Extended European Search Report issued in European Patent Application No. 18777784.2, dated Apr. 16, 2021, 11 pages.
Extended European Search Report (EESR) for EP Application No. 17863986.0, dated Sep. 15, 2020 (13 pages).
Partial Supplementary European Search Report issued in European Patent Application No. 18757770.5 dated Dec. 3, 2020, 11 pages.
Partial Supplementary European Search Report issued in European Patent Application No. 18758239.0, dated Dec. 10, 2020, 11 pages.
European Communication Pursuant to Article 94(3) EPC (Office Action) for EP Application No. 18201132.0 dated Feb. 12, 2021, 5 pages.
Budny et al. "Naviculocuneiform Arthrodesis," Clinics in Podiatric Medicine and Surgery, vol. 24, pp. 753-763, Oct. 2007.
Kamat et al. "Laparoscopic extraction of fractured Kirschner wire from the pelvis," Journal of Minimal Access Surgery, vol. 10, No. 2, pp. 97-98, Jun. 2014.

* cited by examiner

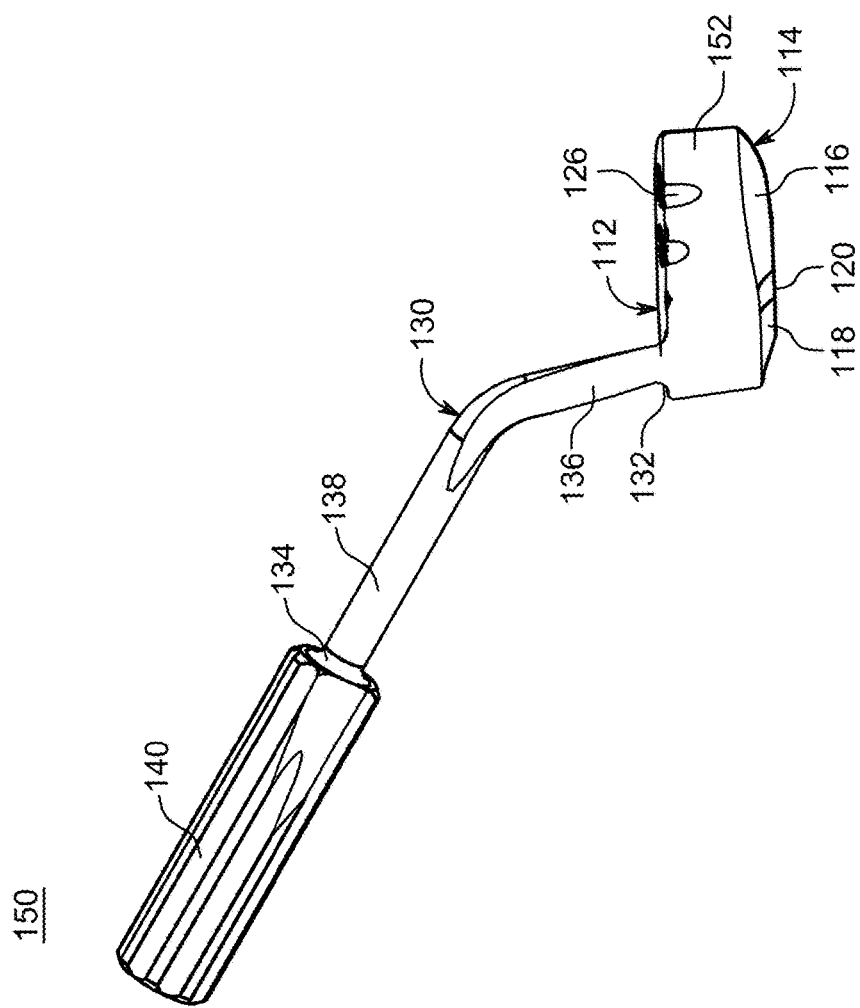
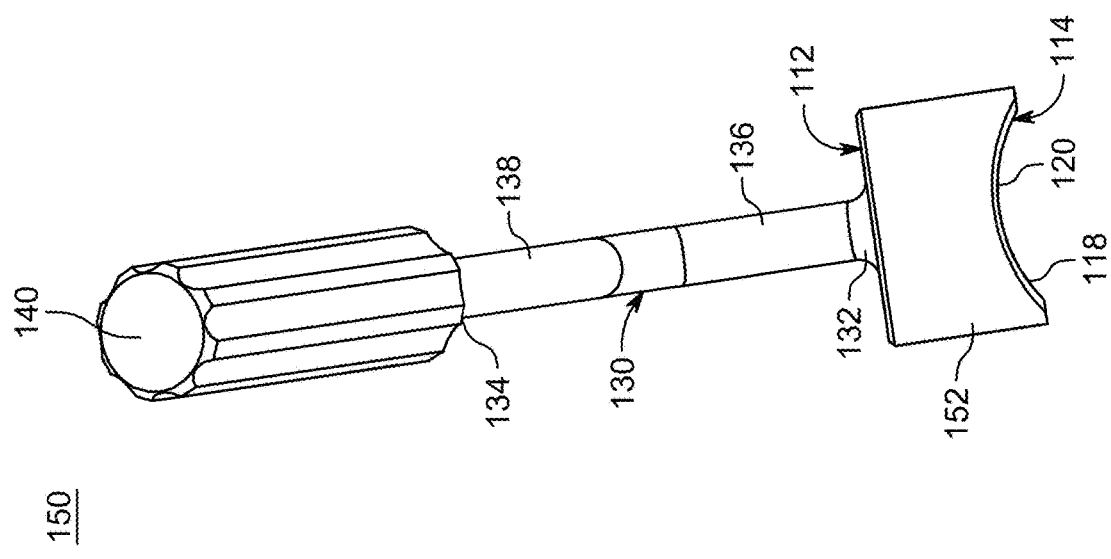

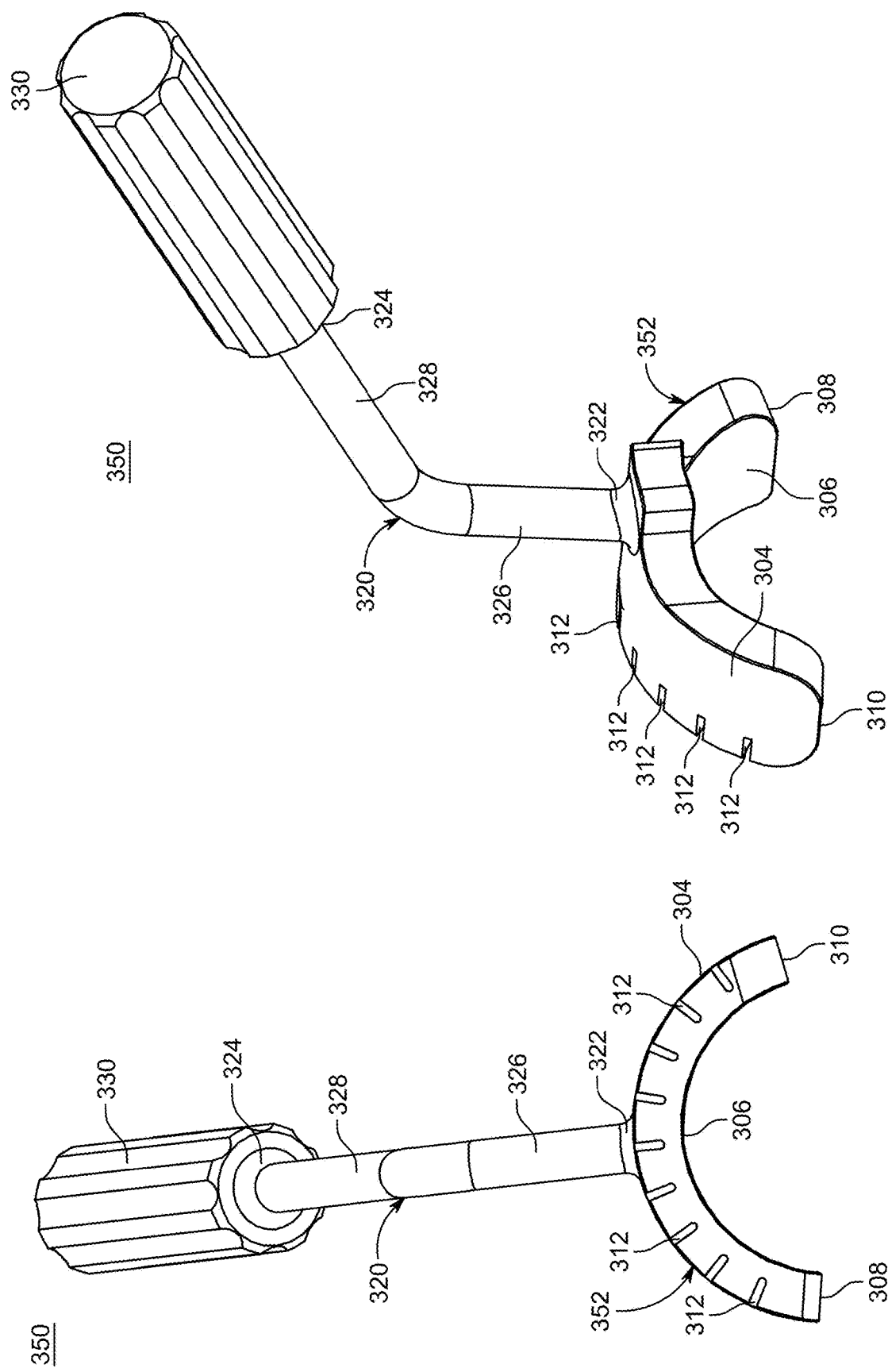

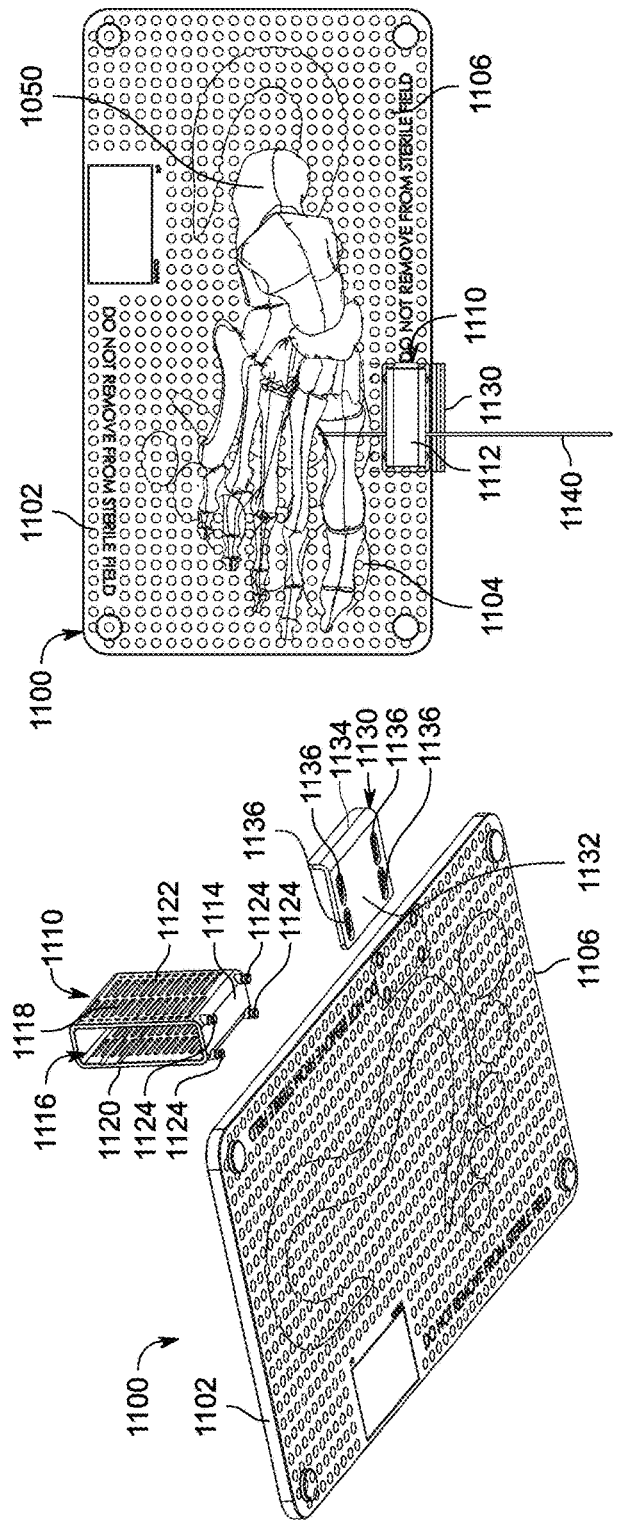
FIG. 88
FIG. 89
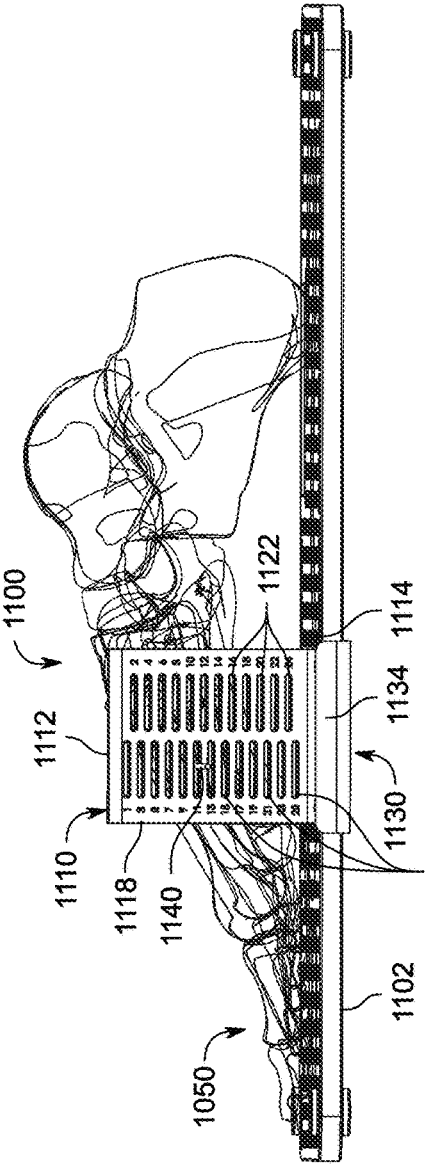
FIG. 90

OSTEOTOMY SYSTEMS, DEVICES AND METHODS

CROSS REFERENCE TO RELATED APPLICATION

This application is a continuation of U.S. application Ser. No. 15/792,730 filed Oct. 24, 2017, which claims priority benefit under 35 U.S.C. § 119(e) of U.S. provisional application Nos. 62/411,768 filed Oct. 24, 2016 and 62/531,176 filed Jul. 11, 2017, which are incorporated herein by reference in their entireties.

FIELD OF THE INVENTION

The present invention relates generally to general surgery, orthopaedic implants used for achieving bone fusion. More specifically, but not exclusively, the present invention relates to osteotomy systems, devices, and methods for using the osteotomy systems.

BACKGROUND OF THE INVENTION

The current surgical techniques for hallux valgus deformities are designed for mild, moderate or severe deformities depending on their correction power. In general, most currently available surgical techniques only correct the deformity in the transverse and/or sagittal planes. One surgical technique for correction of hallux valgus is an osteotomy procedure. Osteotomies have had good success rates and reliability over time. The recurrence rate of the deformity depends on the preoperative deformity, as well as the postoperative sesamoid reduction quality. The recurrence rate being higher if the hallux valgus angle is greater than 37-40 degrees and if postoperatively there is an incomplete reduction of the sesamoids. Most osteotomies are performed in just one plane, generally the transverse plane. None of the current procedures correct the known malrotation that exists in all hallux valgus cases. The malrotation is one possible factor that could be a contributing source to the recurrence of an operated hallux valgus. Thus, new methods for performing osteotomies are needed to correct hallux valgus in all three planes and to reduce the recurrence rate.

SUMMARY OF THE INVENTION

Aspects of the present invention provide osteotomy systems, devices, and methods for using the osteotomy systems for fusing bones.

In one aspect, provided herein is an osteotomy system including an alignment device, at least one first k-wire for insertion into the alignment device, and a cut guide with at least one hole for receiving at least one second k-wire and a slot for receiving a saw blade.

In another aspect, provided herein is an osteotomy kit including an alignment device, a cut guide, and a position rotation device.

In yet another aspect, provided herein is an alignment device including a base with a top surface and a bottom surface, a shaft coupled to the top surface of the base and extending away from the base, and at least one angled opening extending through the base from the top surface to the bottom surface.

In still another aspect, provided herein is a cut guide including a top surface, a bottom surface opposite the top surface, a securement opening positioned at a first end of the cut guide and extending through the cut guide from the top surface to the bottom surface, at least one opening positioned at a second end of the cut guide and extending through the cut guide from a top surface to a bottom surface, and a cutting slot positioned between the first end and the second end and extending through the cut guide from a top surface to a bottom surface.

In another aspect, provided herein is a position rotation device including a base with a first end and a second end, wherein the base is curved from the first end to the second end, at least one angle opening extending through the base, and a shaft coupled to the top surface of the base and extending away from the base.

In yet another aspect, provided herein is a bone plate including a first portion, a second portion coupled to the first portion, at least one first opening positioned in the first portion, at least one second opening position in the second portion, and wherein the second portion is curved as it extends away from the first portion.

In another aspect, provided herein is a surgical method including inserting a first k-wire into a bone and sliding an alignment device over the first k-wire and into contact with the bone. The method also includes inserting a second k-wire through the alignment device and into the bone that corresponds to a rotation angle and removing the first k-wire and the alignment device. In addition, the method includes determining a hole in a cut guide that corresponds to an osteotomy cut angle and positioning the cut guide on the bone and inserting a third k-wire into a distal end of the cut guide. The method also includes guiding a sagittal saw through the cut guide and cutting the bone to form an osteotomy site and removing the cut guide. Further, the method includes rotating the distal end of the bone with respect to the proximal end to a desired angle of rotation and securing the rotated bone.

In still another aspect, provided herein is another surgical method including placing an alignment device on a bone, inserting a k-wire into the alignment device to correspond to a rotation angle, removing the alignment device, determining a hole in the cut guide that corresponds to an osteotomy cut angle, sliding the selected hole of the cut guide over the k-wire, guiding a sagittal saw through the cut guide and cutting the bone, removing the k-wire and cut guide, rotating the distal end of the bone with respect to the proximal end to a desired angle of rotation, and securing the rotated bone.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 15 is a rear view of the alignment device of FIG. 10, in accordance with an aspect of the present invention;

FIG. 16 is a cross-sectional side view of the alignment device of FIG. 11 taken along line 16-16, in accordance with an aspect of the present invention;

FIG. 33 is a front view of the position rotation device of FIG. 29, in accordance with an aspect of the present invention;

FIG. 34 is a rear perspective view of the position rotation device of FIG. 29, in accordance with an aspect of the present invention;

FIG. 88 is an exploded, bottom perspective view of a portion of a foot plate guide, in accordance with an aspect of the present invention;

FIG. 89 is an assembled, top view of the foot plate guide of FIG. 88, in accordance with an aspect of the present invention;

FIG. 90 is an assembled, side view of the foot plate guide of FIG. 88 with a foot positioned on the foot plate, in accordance with an aspect of the present invention;

FIG. 119 is a top view of the position rotation device of FIG. 115, in accordance with an aspect of the present invention;

FIG. 120 is a bottom view of the position rotation device of FIG. 115, in accordance with an aspect of the present invention;

FIG. 121 is a first end view of the position rotation device of FIG. 115, in accordance with an aspect of the present invention;

FIG. 122 is a second end view of the position rotation device of FIG. 115, in accordance with an aspect of the present invention;

FIG. 123 is a cross-sectional view of the position rotation device of FIG. 115 taken along line 123-123 in FIG. 119, in accordance with an aspect of the present invention;

FIG. 124 is a perspective view of an embodiment of an osteotomy system, in accordance with an aspect of the present invention.

DETAILED DESCRIPTION FOR CARRYING OUT THE INVENTION

Figure 1:
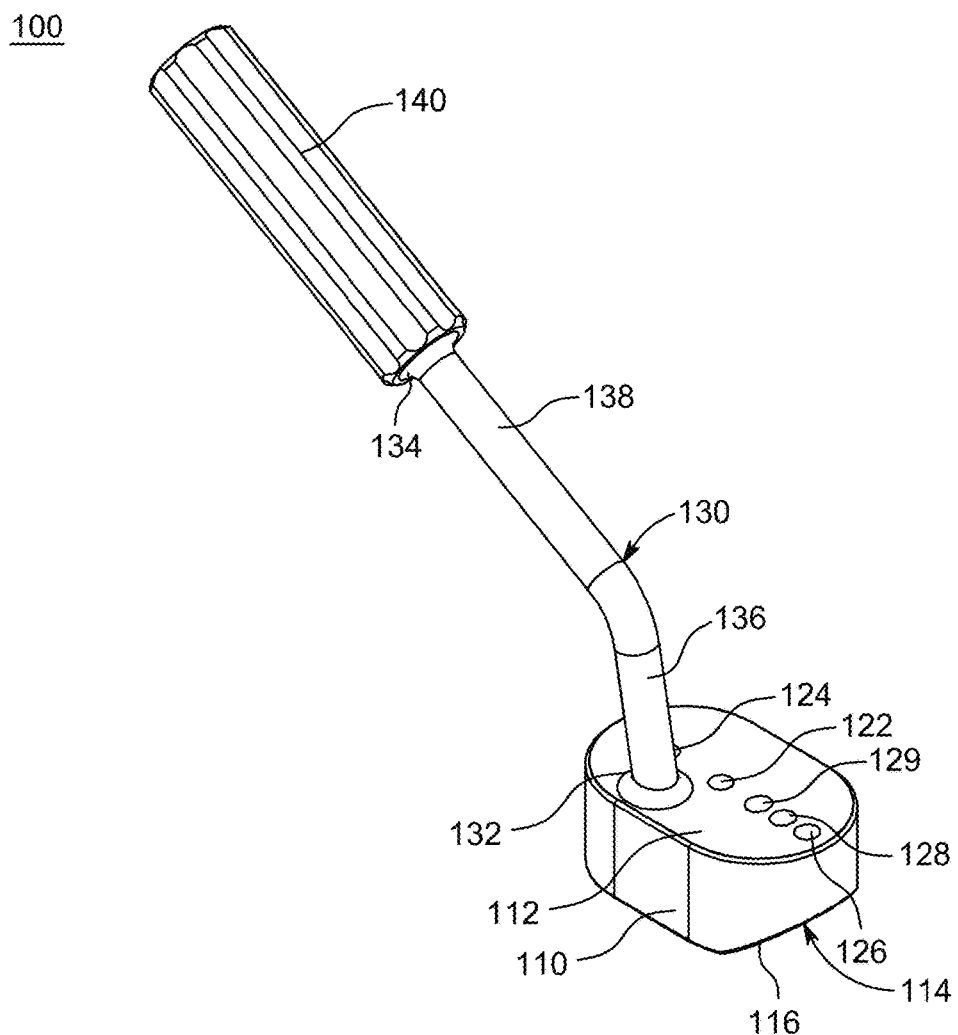
FIG. 1 is a perspective view of one embodiment of an alignment device, in accordance with an aspect of the present invention.
Figure 2:
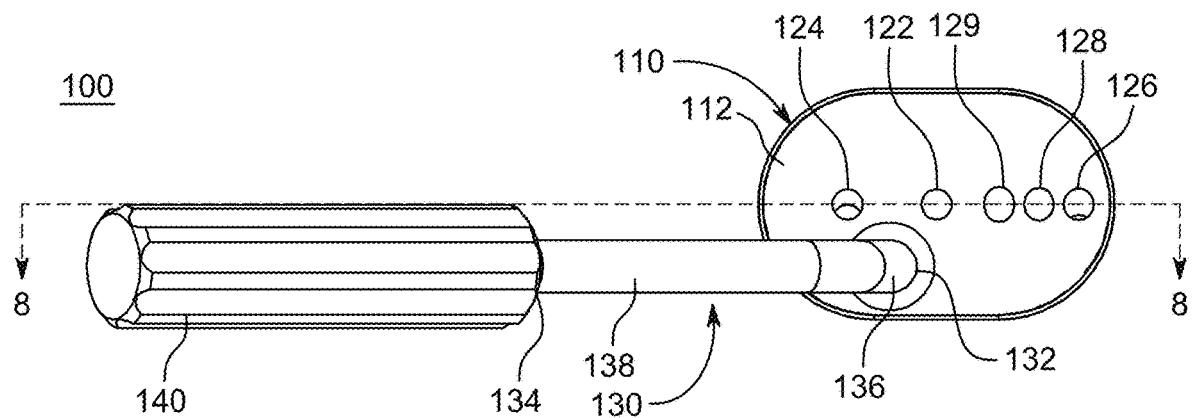
FIG. 2 is a top view of the alignment device of FIG. 1, in accordance with an aspect of the present invention.
Figure 3:
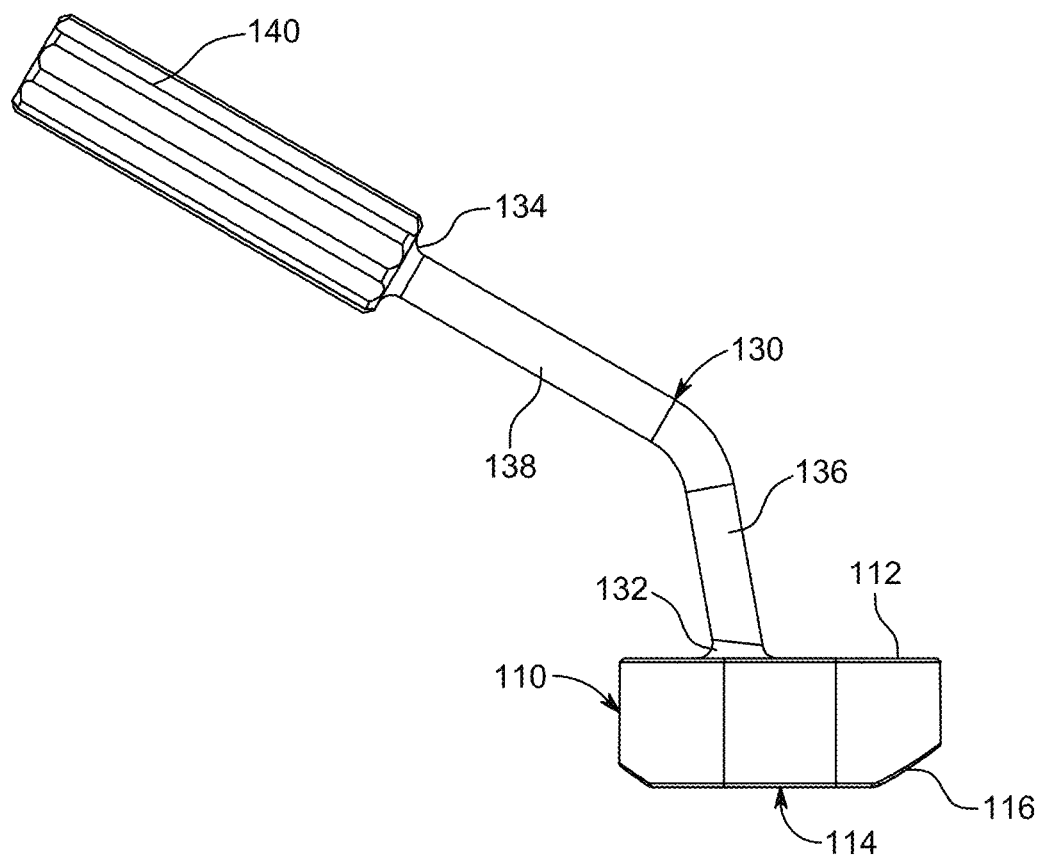
FIG. 3 is a side view of the alignment device of FIG. 1, in accordance with an aspect of the present invention.

Generally stated, disclosed herein are osteotomy systems, kits, devices and implants. Further, a surgical method for using the osteotomy systems, kits, devices and implants are discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Similarly, positions or directions may be used herein with reference to anatomical structures or surfaces. For example, as the current devices and methods are described herein with reference to use with the bones of the foot, the bones of the foot, ankle and lower leg may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices and methods, and the aspects, components, features and the like thereof, described herein with respect to a right foot may be mirrored so that they likewise function with a left foot and vice versa. Further, the devices and methods, and the aspects, components, features and the like thereof, disclosed herein are described with respect to the foot for brevity purposes, but it should be understood that the devices and methods may be used with other bones of the body having similar structures, for example the upper extremity, and more specifically, with the bones of the wrist, hand, and arm.

Referring to the drawings, wherein like reference numerals are used to indicate like or analogous components throughout the several views, and with particular reference to FIGS. 1-48, there are illustrated the devices of the osteotomy systems. In addition, the devices of the osteotomy systems are shown in use on a bone in FIGS. 49-58. One embodiment of an osteotomy system may include, for example, an alignment device 100, 150, a cut guide 200, a position rotating device 300, 350, k-wires or fixation devices 410, 412, a k-wire or fixation device 420, an electric oscillating microsagittal saw or saw blade 430, and a plate 500, 550.

Figure 4:
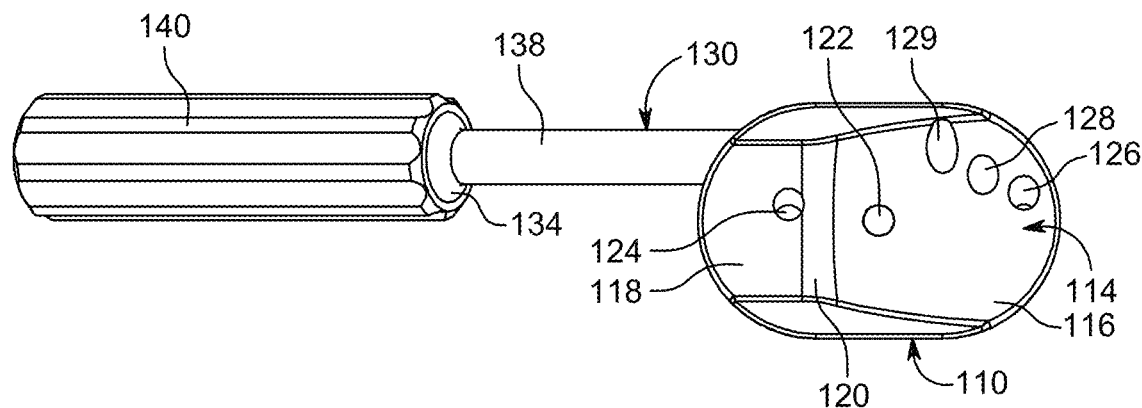
FIG. 4 is a bottom view of the alignment device of FIG. 1, in accordance with an aspect of the present invention.
Figure 6:
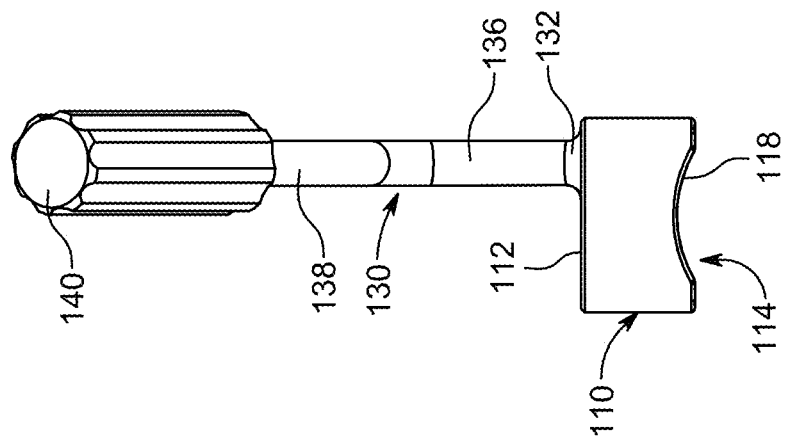
FIG. 6 is a rear view of the alignment device of FIG. 1, in accordance with an aspect of the present invention.
Figure 5:
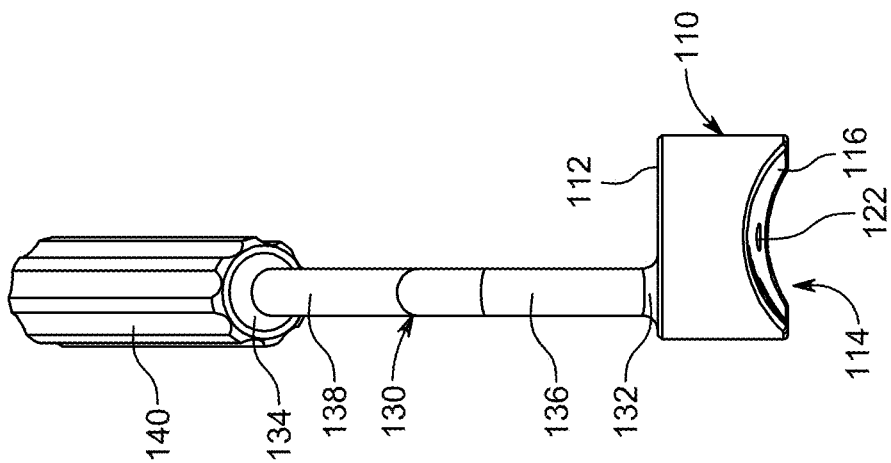
FIG. 5 is a front view of the alignment device of FIG. 1, in accordance with an aspect of the present invention.
Figure 7:
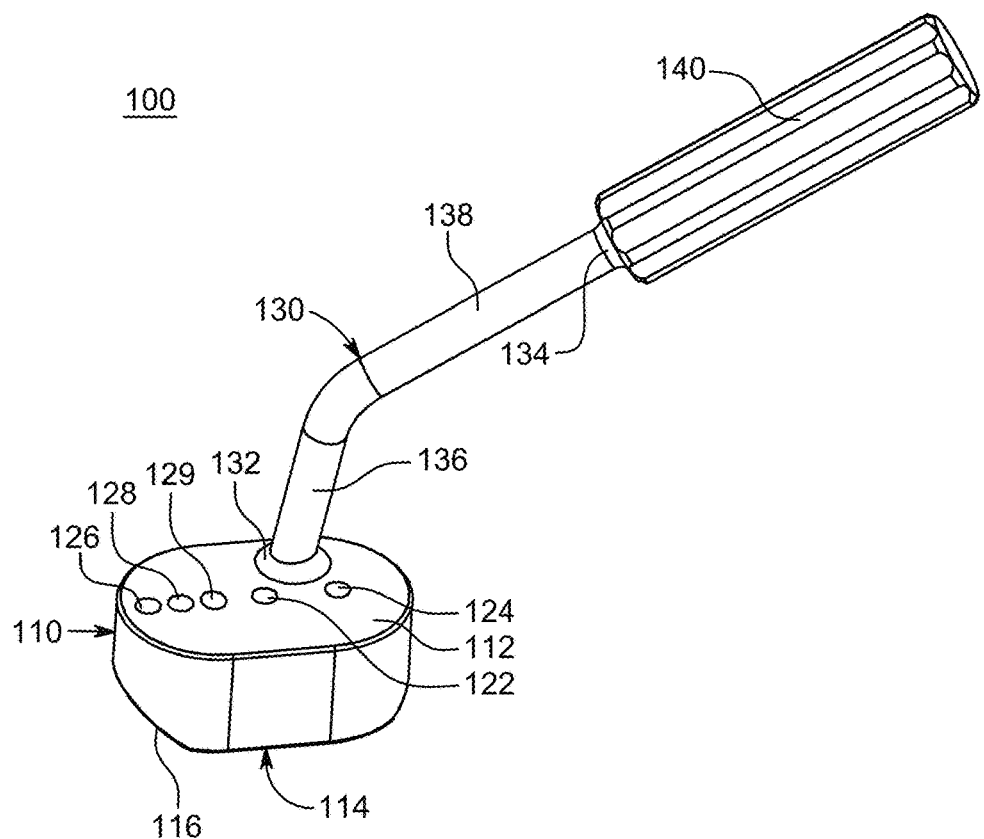
FIG. 7 is a top perspective view of the alignment device of FIG. 1, in accordance with an aspect of the present invention.
Figure 8:
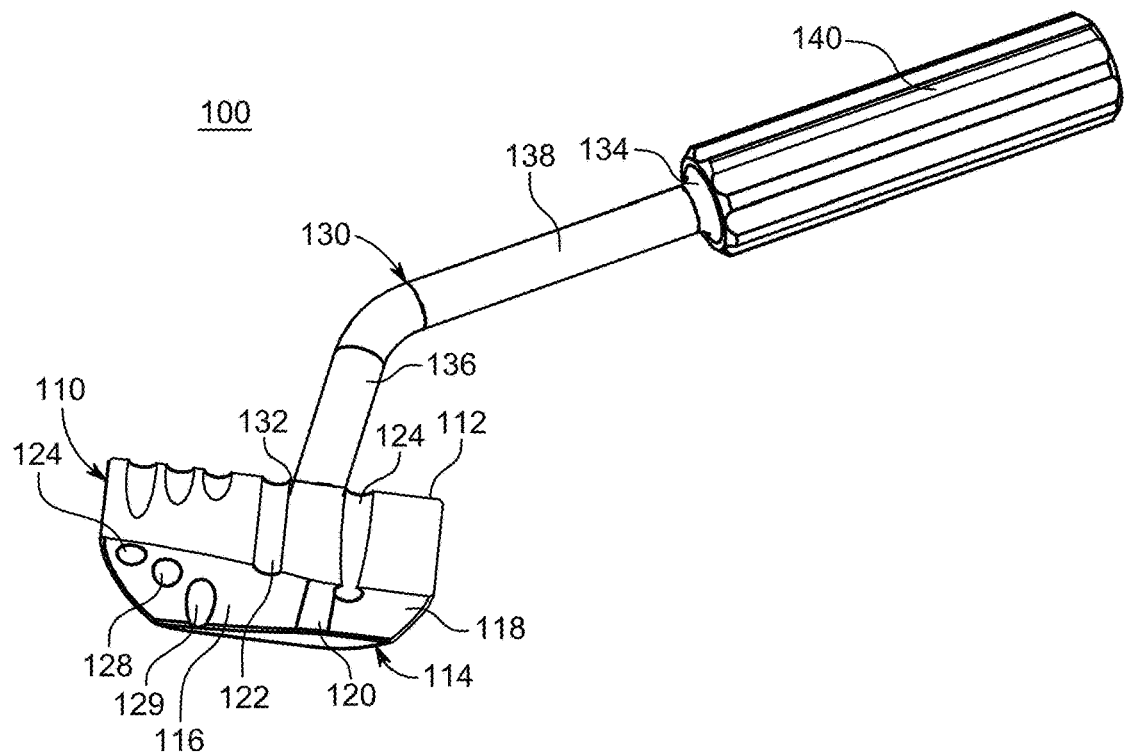
FIG. 8 is a cross-sectional bottom, side perspective view of the alignment device of FIG. 2 taken along line 8-8, in accordance with an aspect of the present invention.
Figure 9:
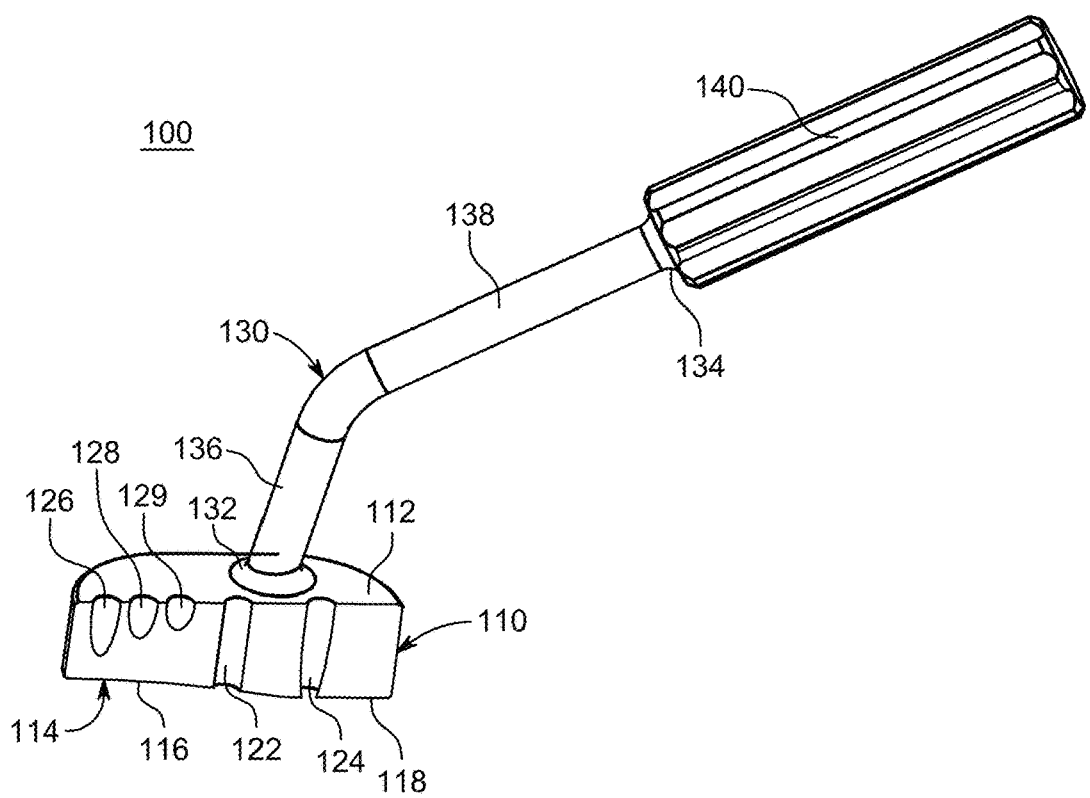
FIG. 9 is a cross-sectional top, side perspective view of the alignment device of FIG. 2 taken along line 8-8, in accordance with an aspect of the present invention.

The alignment device 100 is shown in FIGS. 1-9. The alignment device 100 may include a base 110, a shaft 130 coupled to the base 110, and a handle 140 coupled to the shaft 130. The base 110 may include a top surface 112 and a bottom surface 114. As best seen in FIG. 5-7, the bottom surface 114 includes a first portion 116 with a first curvature, a second portion 118 with a second curvature, and a transition zone 120 with a third curvature. The first portion 116 is positioned at a first angle with respect to the transition zone 120 and the second portion 118 is positioned at a second angle with respect to the transition zone 120. For example, in the depicted embodiment, the first angle is greater than the second angle. As shown in FIG. 4, the first portion 116, second portion 118 and transition zone 120 may only be inset into a portion of the base 110 leaving sidewall portions along at least a portion of the length of the base 110.

As shown in FIGS. 1, 2, 4, and 7-9, the base 110 may also include a zero opening 122 positioned near the shaft 130. A first angled opening 124 positioned between the zero opening 122 and the proximal end of the base 110. A second angled opening 126 positioned near the distal end of the base 110. A third angled opening 128 positioned between the zero opening 122 and the second angled opening 126. A fourth angled opening 129 positioned between the zero opening 122 and the third angled opening 128. The openings 122, 124, 126, 128, 129 may each be positioned at a specific rotation angle as it passes through the base 110 from a top surface 112 to a bottom surface 114. For example, the zero opening 122 may have an angle of 0° for positioning and aligning the alignment device 100. The first angled opening 124 may be angled, for example, 7.5° and may have a rotation angle of, for example, 15°. The second angled opening 126 may be angled, for example, 15° and may have a rotation angle of, for example, 30°. The third angled opening 128 may be angled, for example, 22.5° and may have a rotation angle of, for example, 45°. The fourth angled opening 129 may be angled, for example, 30° and may have a rotation angle of, for example, 60°. As illustrated in the depicted embodiment of FIGS. 1-9, the openings 122, 124, 126, 128, 129 may be positioned linearly along the top surface 112 of the base 110. The openings 122, 124, 126, 128, 129 may be positioned in any 2D layout to ensure that the plantar portion of the osteotomy terminates a certain distance from the joint line, for example, approximately 10 mm.

With continued reference to FIGS. 1-9, the shaft 130 includes a first end 132 coupled to the base 110 and a second end 134 coupled to the handle 140. The shaft 130 may include a first segment 136 near the first end 132 and a second segment 138 near the second end 134. The first segment 136 may be angled relative to the second segment 138. The shaft 130 may be positioned offset to one side of the top surface 112 and between a center and proximal end of the base 110.

Figure 13:
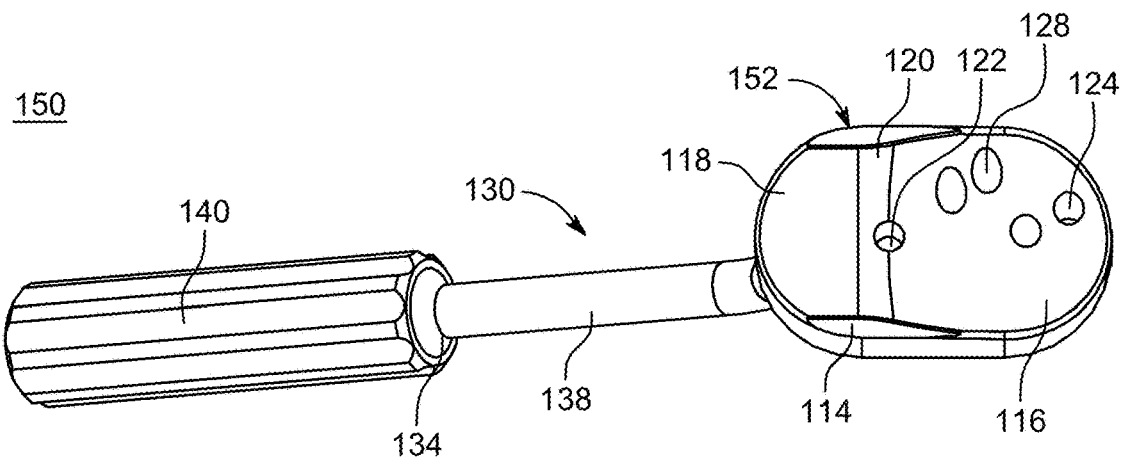
FIG. 13 is a bottom view of the alignment device of FIG. 10, in accordance with an aspect of the present invention.
Figure 14:
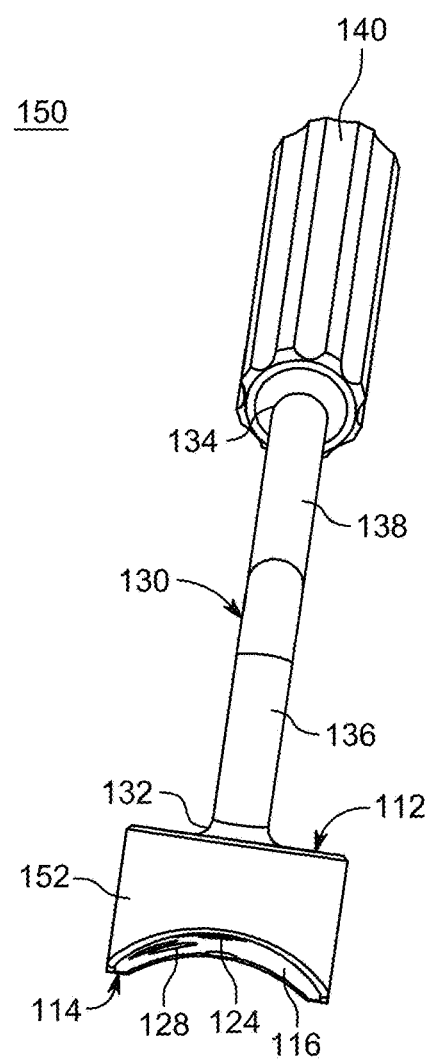
FIG. 14 is a front perspective view of the alignment device of FIG. 10, in accordance with an aspect of the present invention.
Figure 17:
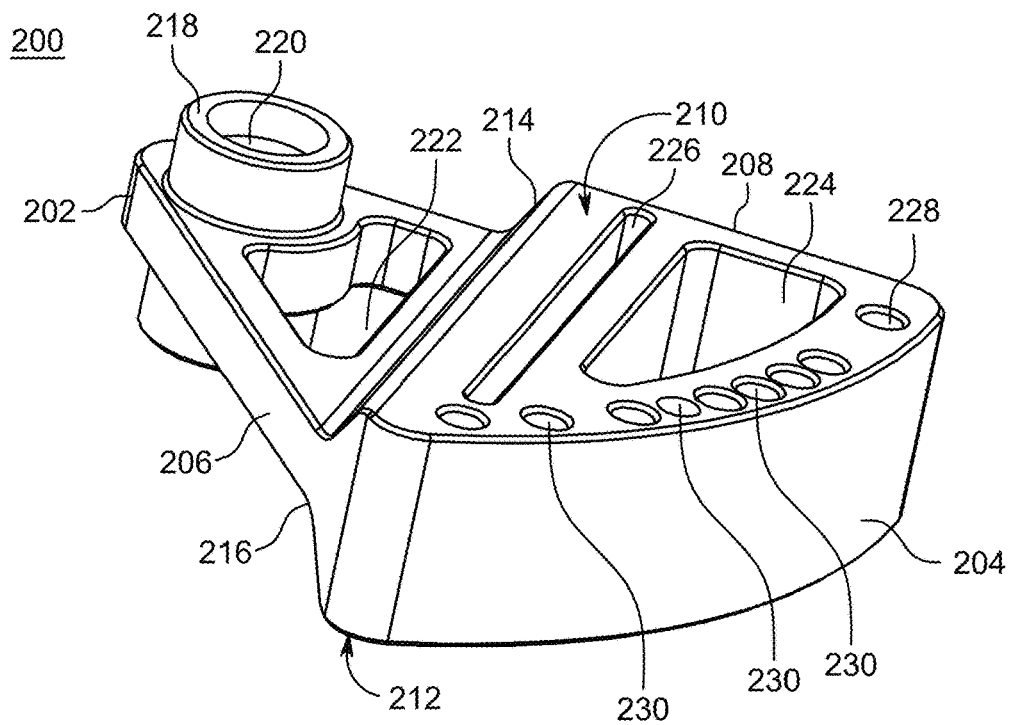
FIG. 17 is a side perspective view of a cut guide, in accordance with an aspect of the present invention.
Figure 18:
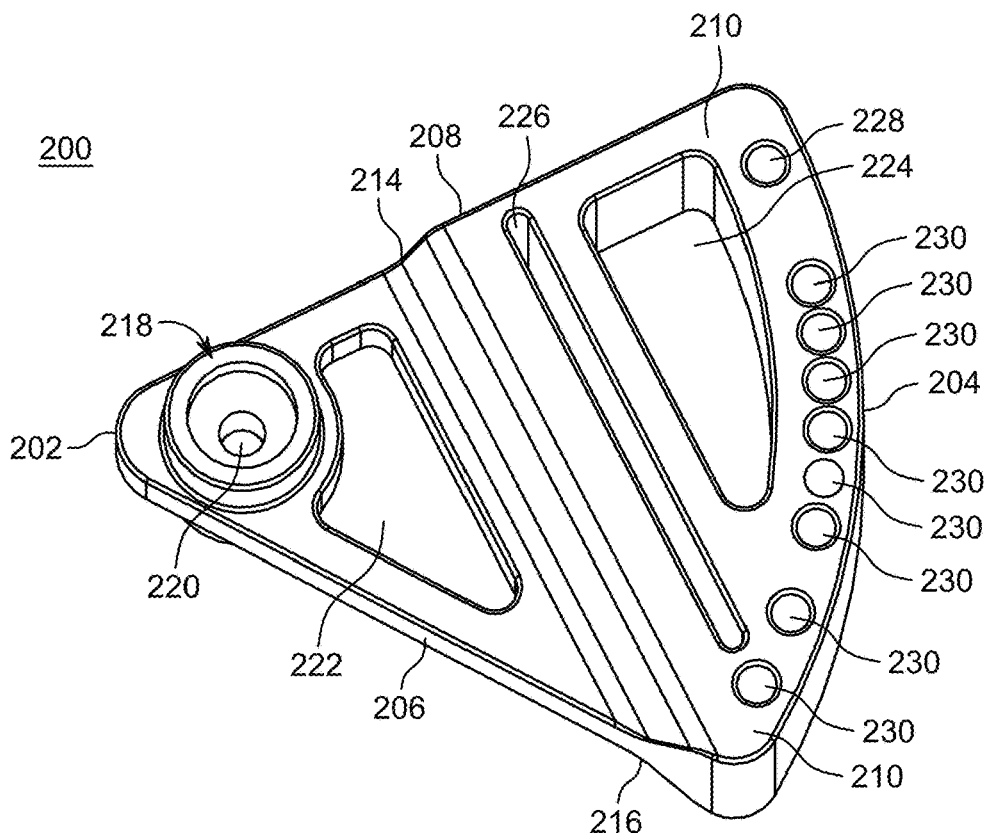
FIG. 18 is a top view of the cut guide of FIG. 17, in accordance with an aspect of the present invention.

Referring now to FIGS. 10-16, another embodiment of an alignment device 150 is shown. The alignment device 150 may include a base 152, a shaft 130 coupled to the proximal end of the base 152, and a handle 140 coupled to the shaft 130. The shaft 130 is as described above with reference to FIGS. 1-9 and will not be described again here for brevity sake. The base 152 may include a top surface 112 and a bottom surface 114. As best seen in FIG. 13-15, the bottom surface 114 includes a first portion 116 with a first curvature, a second portion 118 with a second curvature, and a transition zone 120 with a third curvature. The first portion 116 is positioned at a first angle with respect to the transition zone 120 and the second portion 118 is positioned at a second angle with respect to the transition zone 120. For example, in the depicted embodiment, the first angle is greater than the second angle. As shown in FIG. 13, the first portion 116, second portion 118 and transition zone 120 may only be inset into a portion of the base 110 leaving sidewall portions along at least a portion of the length of the base 110.

Figure 10:
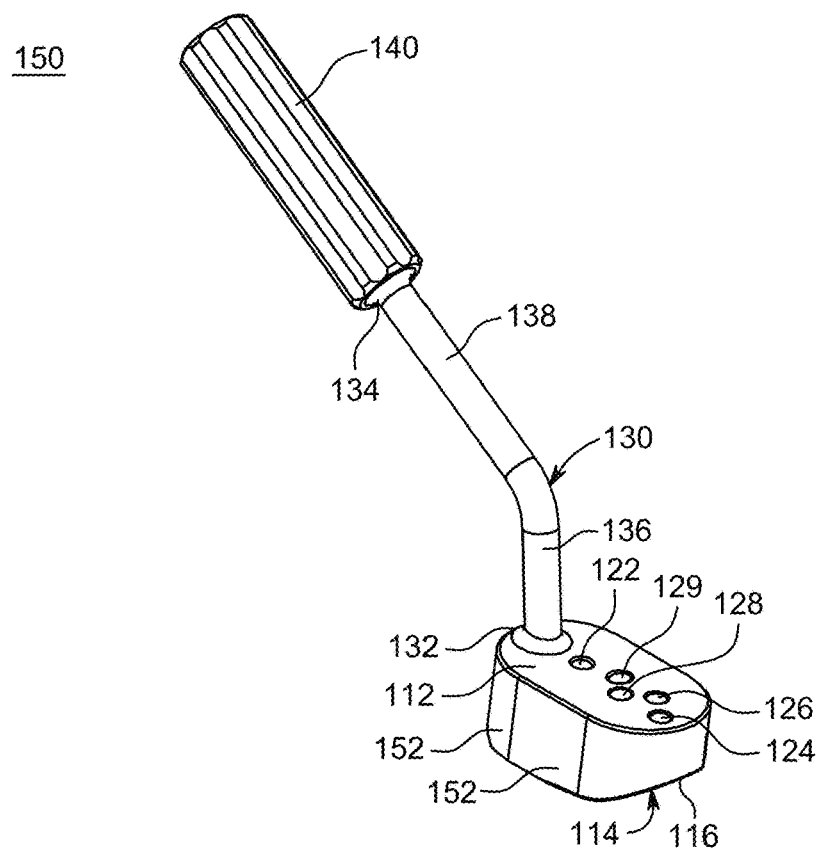
FIG. 10 is a perspective view of another embodiment of an alignment device, in accordance with an aspect of the present invention.
Figure 11:
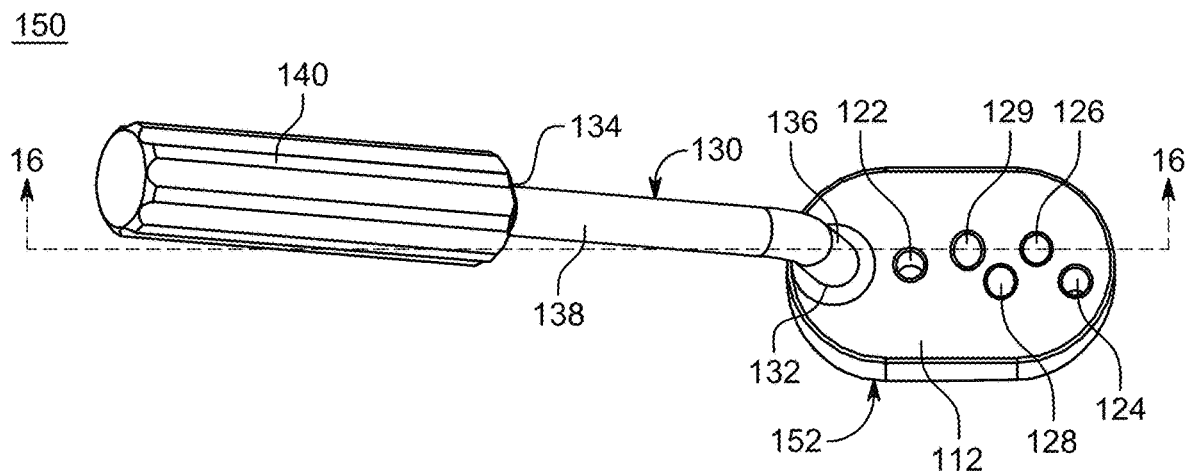
FIG. 11 is a top view of the alignment device of FIG. 10, in accordance with an aspect of the present invention.
Figure 12:
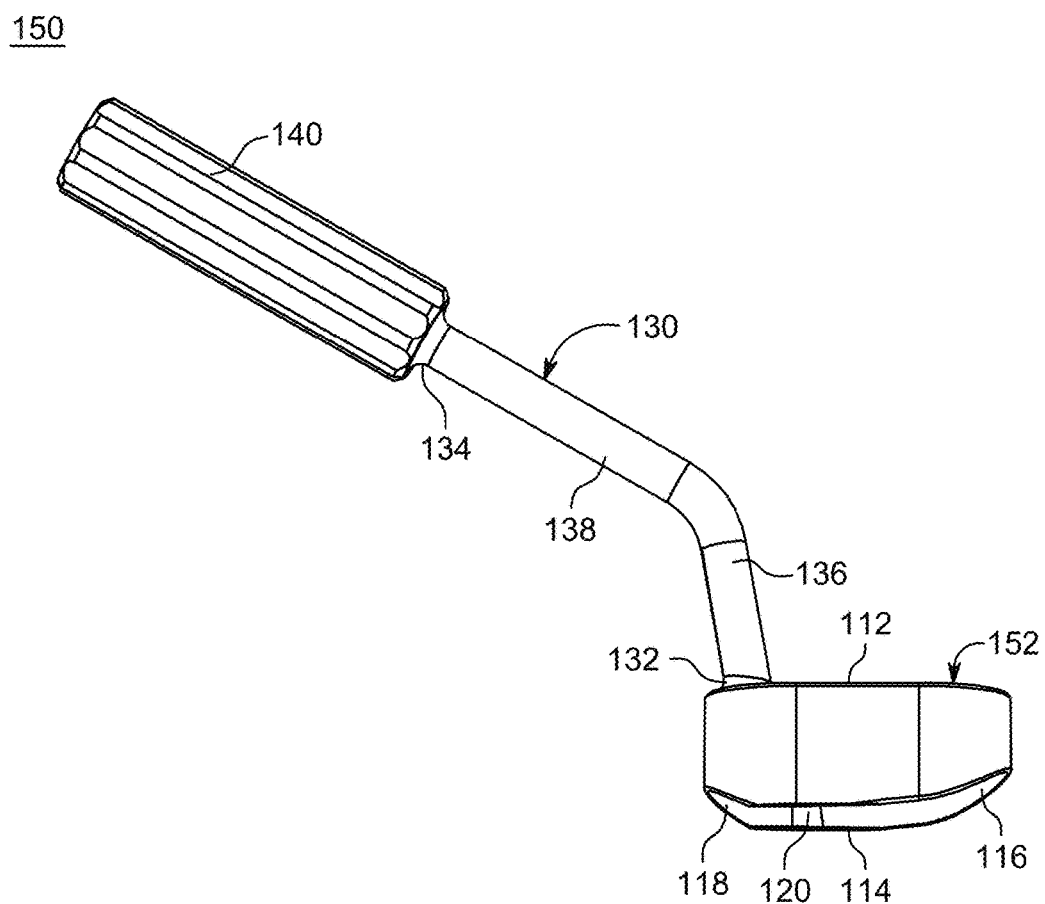
FIG. 12 is a side perspective view of the alignment device of FIG. 10, in accordance with an aspect of the present invention.

As shown in FIGS. 10, 11 and 13, the base 152 may also include openings 122, 124, 126, 128, 129. The openings 122, 124, 126, 128, 129 may be positioned extending through the base 152 from a top surface 112 through the bottom surface 114. The zero opening 122 may be positioned near the shaft 130. The first angled opening 124 positioned near the distal end of the base 152. The second angled opening 126 positioned between the first angled opening 124 the third angled opening 128 and offset from the first and third angled openings 124, 128. The third angled opening 128 positioned between the second angled opening 126 and the fourth angled opening 129. The fourth angled opening 129 positioned between the zero opening 122 and the third angled opening 128 and offset from the zero opening 122 and the third angled opening 128. The openings 122, 124, 126, 128, 129 may each be positioned at a specific rotation angle as it passes through the base 152 from a top surface 112 to a bottom surface 114. For example, the zero opening 122 may have an angle of 0° for positioning and aligning the alignment device 150. The first angled opening 124 may have a rotation angle of, for example, 15°. The second angled opening 126 may have a rotation angle of, for example, 30°. The third angled opening 128 may have a rotation angle of, for example, 45°. The fourth angled opening 129 may have a rotation angle of, for example, 60°. As illustrated in the depicted embodiment of FIGS. 10-16, the openings 122, 124, 126, 128, 129 may be positioned offset or staggered from the adjacent openings 122, 124, 126, 128, 129 along the top surface 112 of the base 152. Alternative positions for the openings 122, 124, 126, 128, 129 are also contemplated to allow for each opening 122, 124, 126, 128, 129 to be positioned at a desired angle with respect to the base 152 and to not intersect with any other opening 122, 124, 126, 128, 129. The openings 122, 124, 126, 128, 129 may be positioned in any 2D layout to ensure that the plantar portion of the osteotomy terminates a certain distance from the joint line, for example, approximately 10 mm.

Referring to FIGS. 17-22, the cut guide 200 is shown. The cut guide 200 includes a first end 202 and a second end 204. The cut guide 200 may also include a first side 206 and a second side 208 extending from the first end 202 to the second end 204. The cut guide 200 may have, for example, a relatively triangular shape with a point at the first end 202 and the second end 204, the first side 206, and the second side 208 making up the three sides of the triangle. The second end 204 may be curved between the first and second sides 206, 208. The cut guide 200 may also include a top surface 210 and a bottom surface 212. In addition, the cut guide 200 may include a transition zone 214, 216 positioned between the first end 202 and the second end 204.

Figure 19:
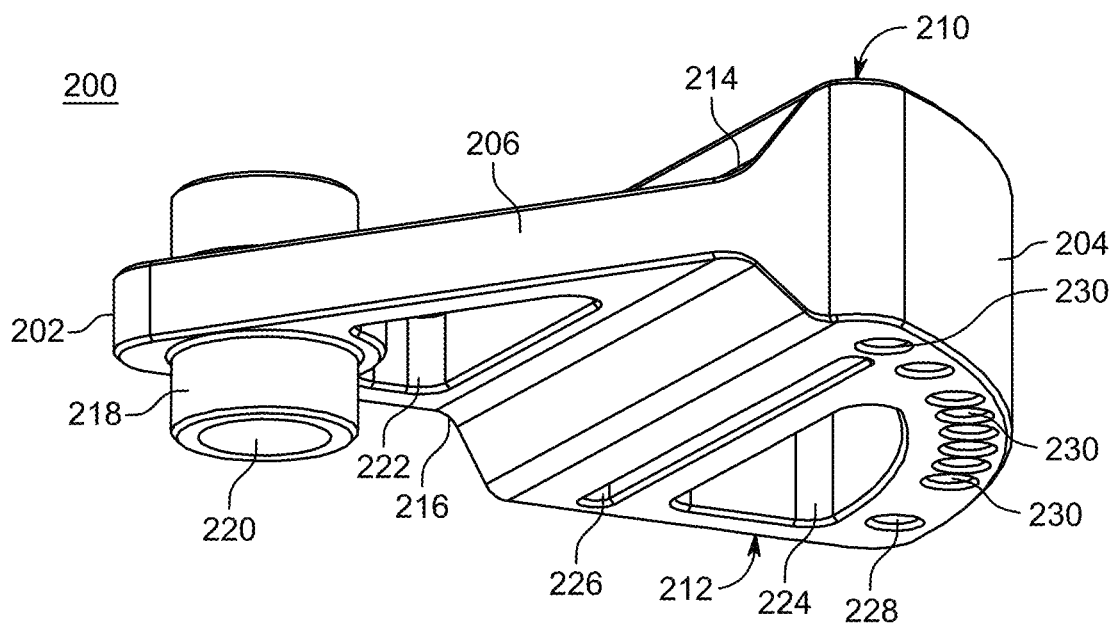
FIG. 19 is a bottom perspective view of the cut guide of FIG. 17, in accordance with an aspect of the present invention.
Figure 20:
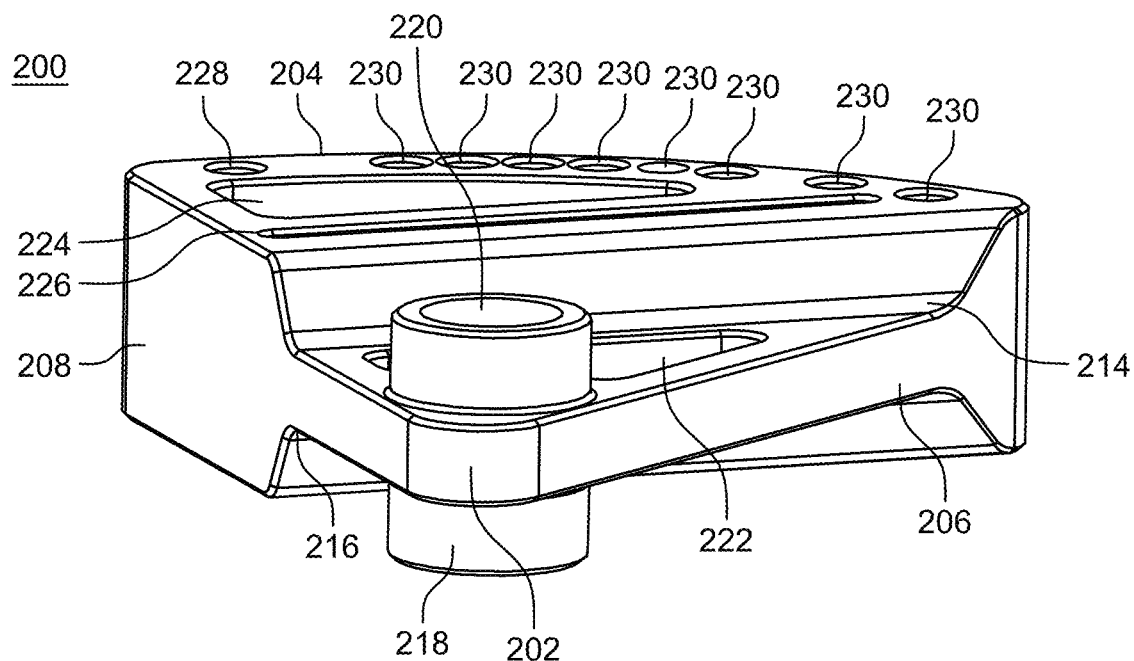
FIG. 20 is an end perspective view of the cut guide of FIG. 17, in accordance with an aspect of the present invention.
Figure 21:
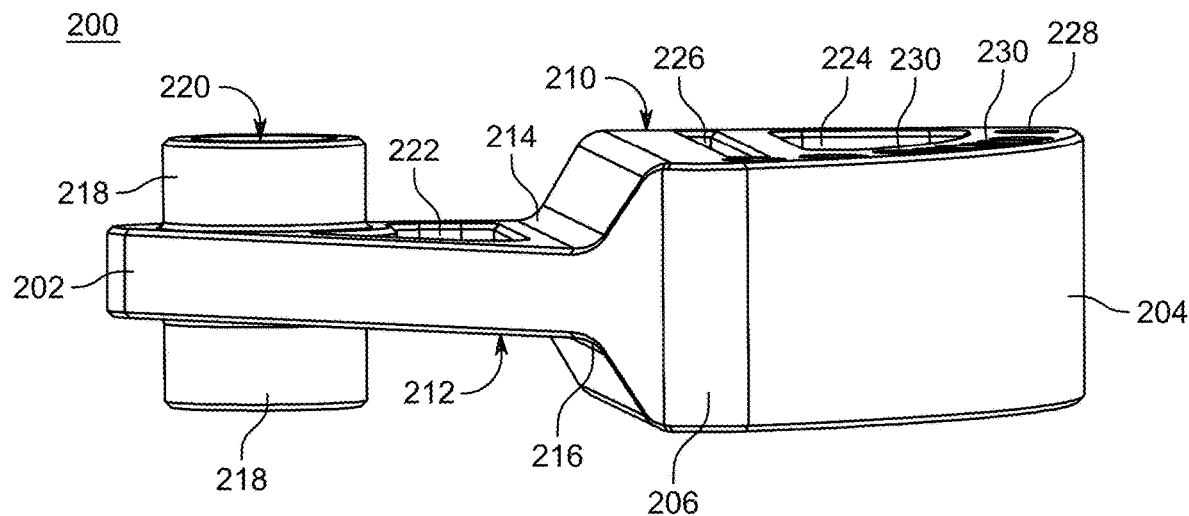
FIG. 21 is a side view of the cut guide of FIG. 17, in accordance with an aspect of the present invention.

As shown in FIGS. 19-21, the first end 202 of the cut guide 200 may have a thickness between the top and bottom surfaces 210, 212 that is less than the thickness at the second end 204 between the top and bottom surfaces 210, 212. The first transition zone 214 may be angled on the top surface 210 between the first end 202 and the second end 204. The second transition zone 216 may be angled on the bottom surface 212 between the first end and the second end 204. The transition zone 214, 216 may be angled with respect to the second end 204.

With continued reference to FIGS. 17-21, the cut guide 200 may also include a securement member 218 positioned near the first end 202 of the cut guide 200. The securement member 218 may also include an opening 220 extending through the securement member 218 from the top surface 210 through the bottom surface 212. The cut guide 200 may further include a first window 222 positioned near the first end 202 and a second window 224 positioned near the second end 204. The windows 222, 224 may extend through the cut guide 200 from the top surface 210 to the bottom surface 212. The first and second windows 222, 224 may be positioned and sized to provide visualization of the bone. The first window 222 may be positioned, for example, between the securement member 218 and the transition zone 214, 216. The second window 224 may be positioned, for example, between the transition zone 214, 216 and the second end 204. In addition, the cut guide 200 may include at least one cutting slot 226 extending between the first side 206 and the second side 208. The at least one cutting slot 226 may be positioned, for example, adjacent and parallel to the transition zone 214, 216. In one embodiment, the cut guide 200 may include multiple cutting slots 226 positioned next to each other on and generally adjacent to the second end 204 of the cut guide 200.

Figure 22:
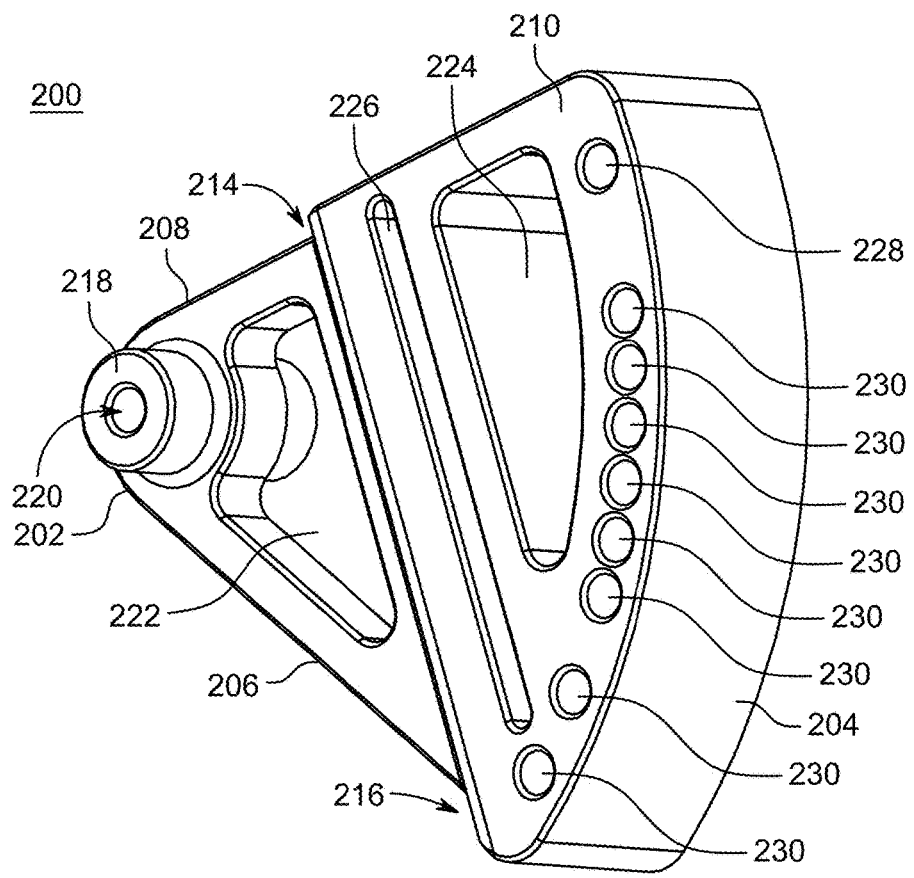
FIG. 22 is a top perspective view of another cut guide, in accordance with an aspect of the present invention.
Figure 23:
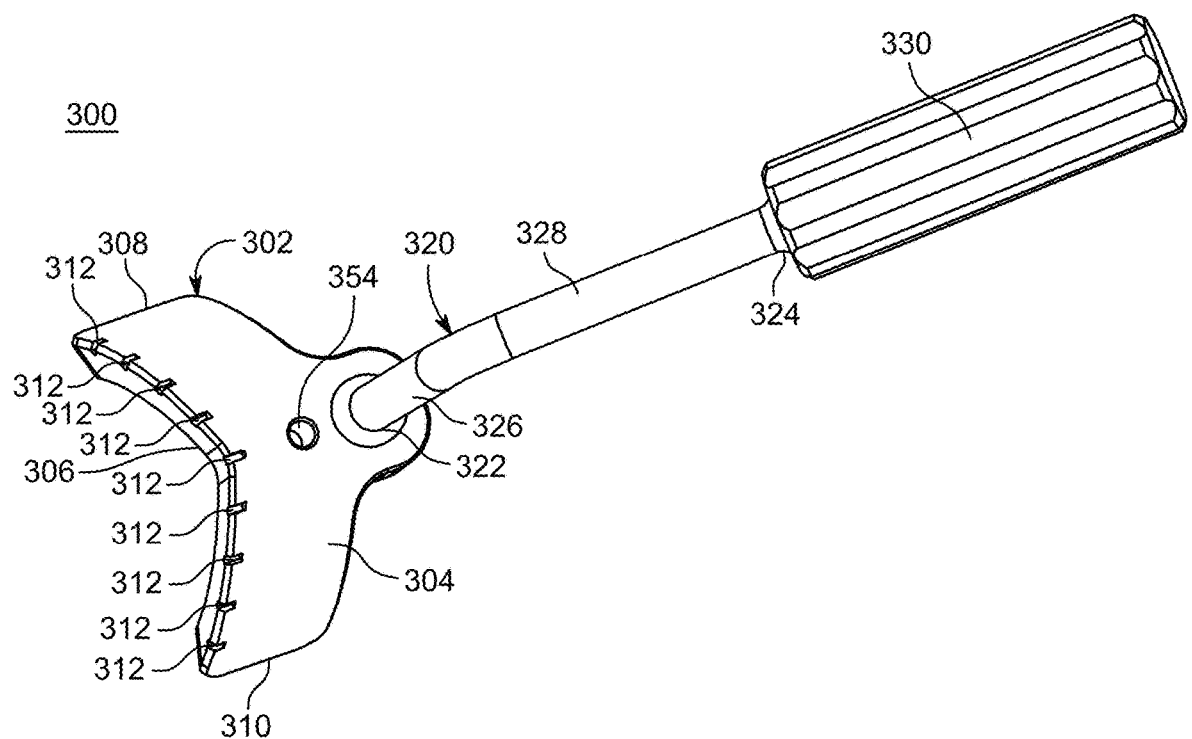
FIG. 23 is a perspective view of a position rotation device, in accordance with an aspect of the present invention.
Figure 24:
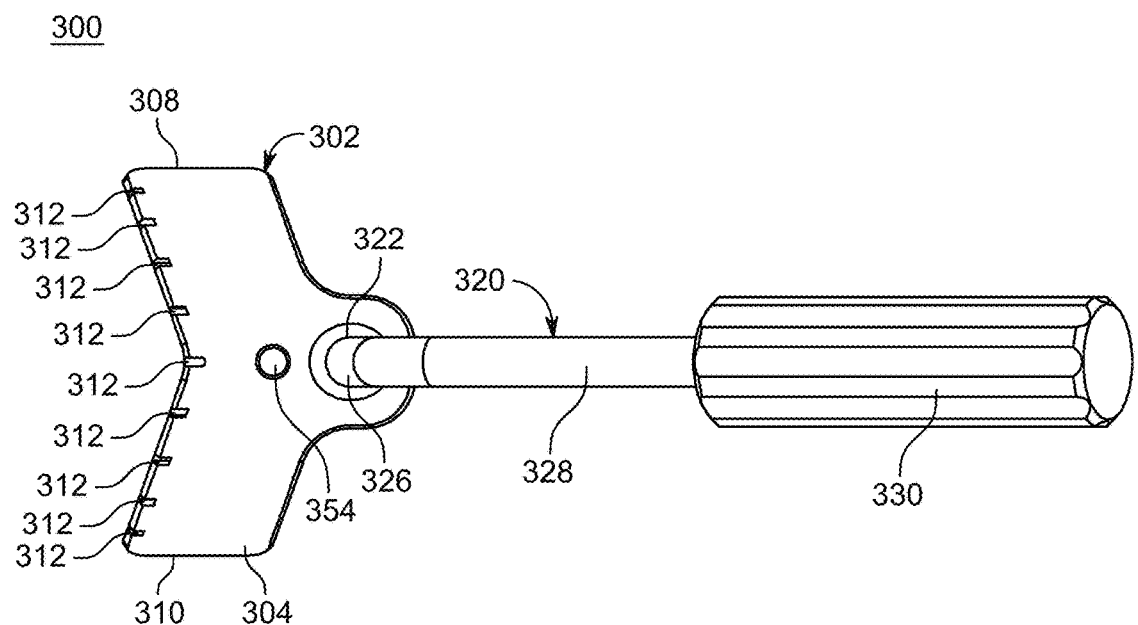
FIG. 24 is a top view of the position rotation device of FIG. 23, in accordance with an aspect of the present invention.
Figure 25:
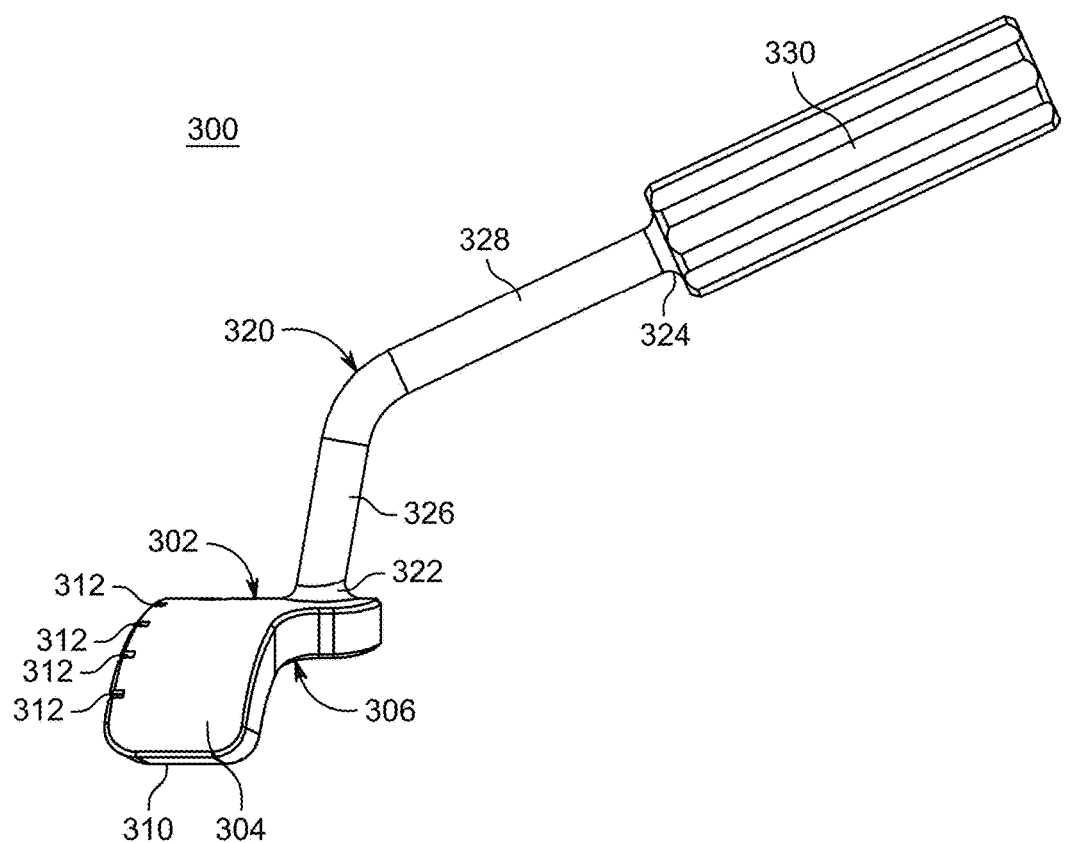
FIG. 25 is a side view of the position rotation device of FIG. 23, in accordance with an aspect of the present invention.
Figure 26:
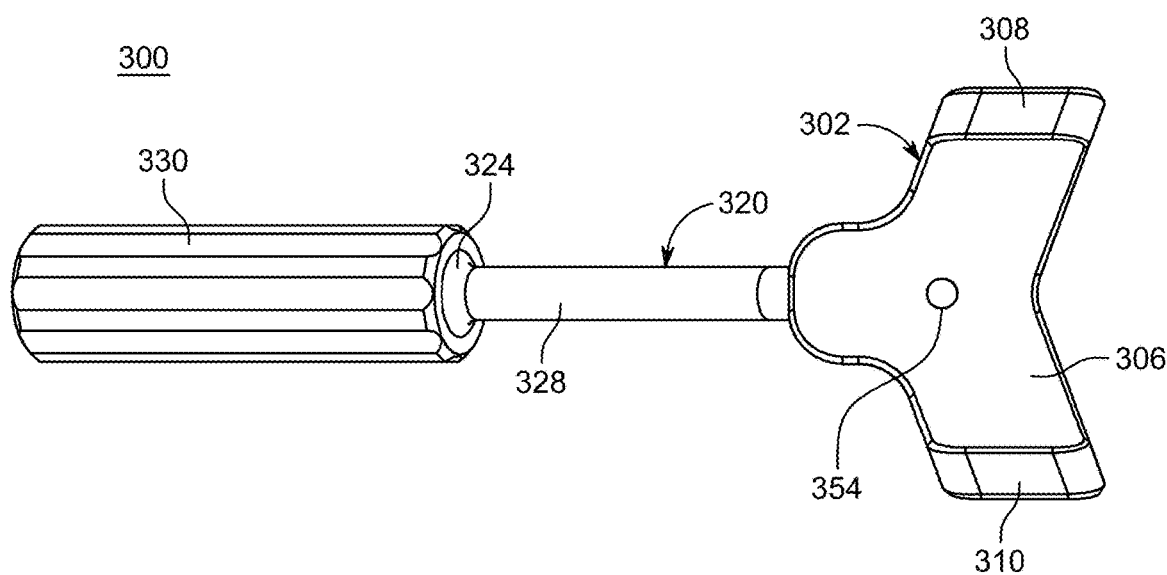
FIG. 26 is a bottom view of the position rotation device of FIG. 23, in accordance with an aspect of the present invention.
Figure 28:
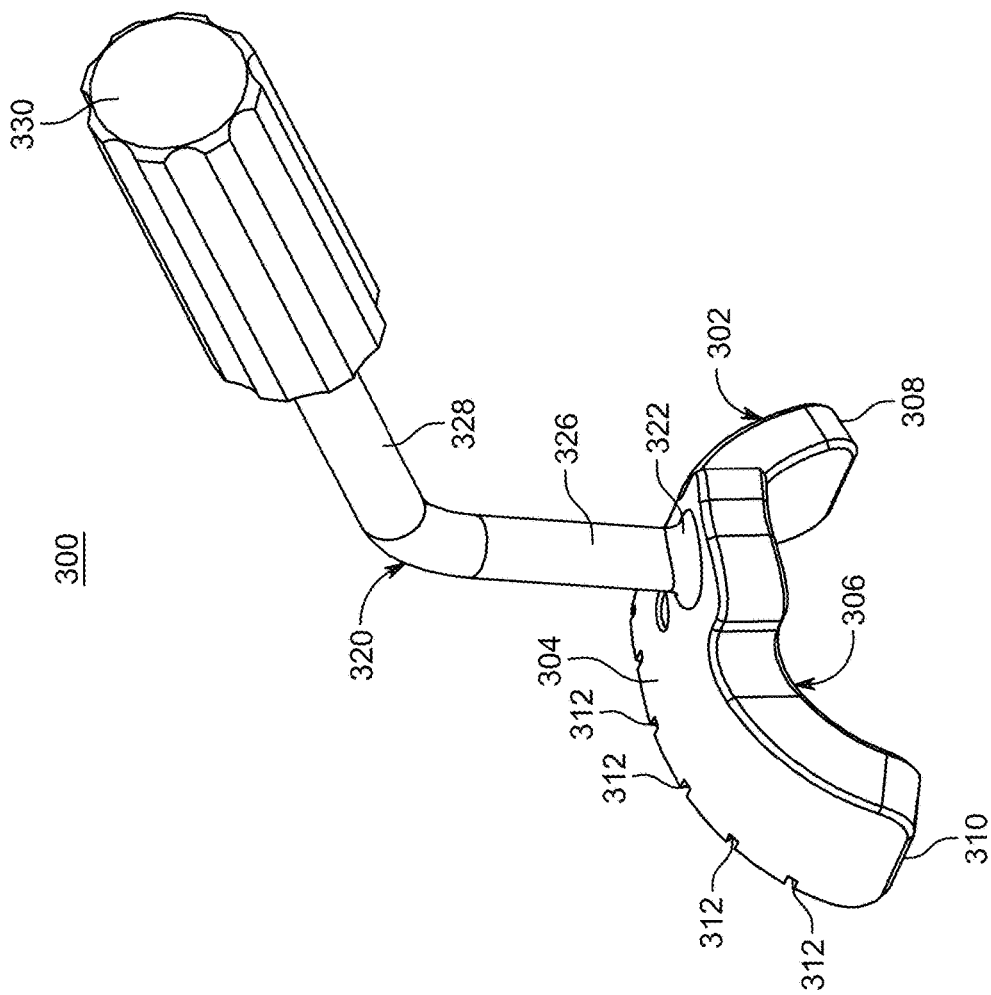
FIG. 28 is a rear perspective view of the position rotation device of FIG. 23, in accordance with an aspect of the present invention.
Figure 27:
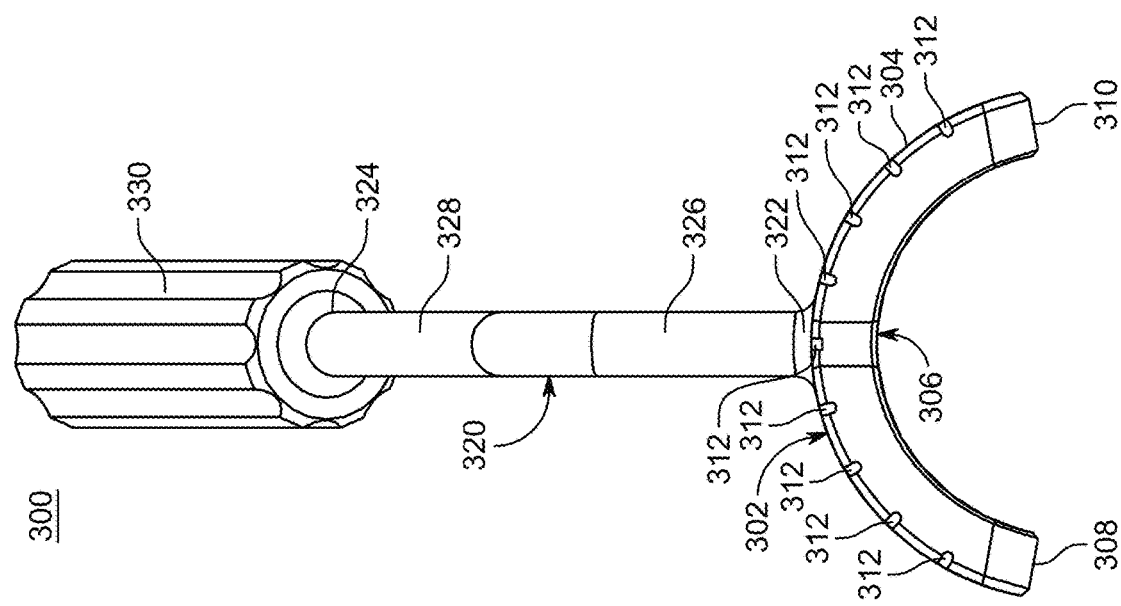
FIG. 27 is a front view of the position rotation device of FIG. 23, in accordance with an aspect of the present invention.
Figure 29:
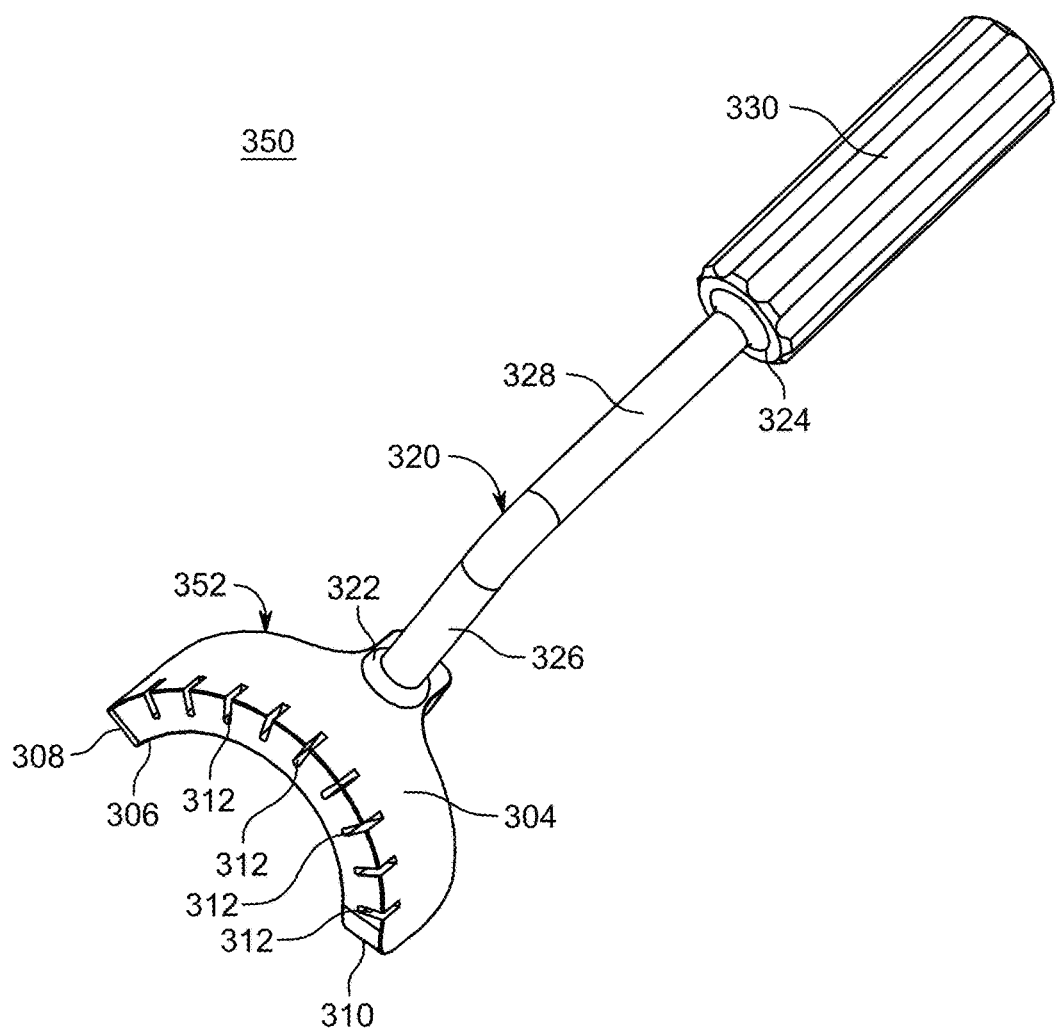
FIG. 29 is a perspective view of another position rotation device, in accordance with an aspect of the present invention.
Figure 30:
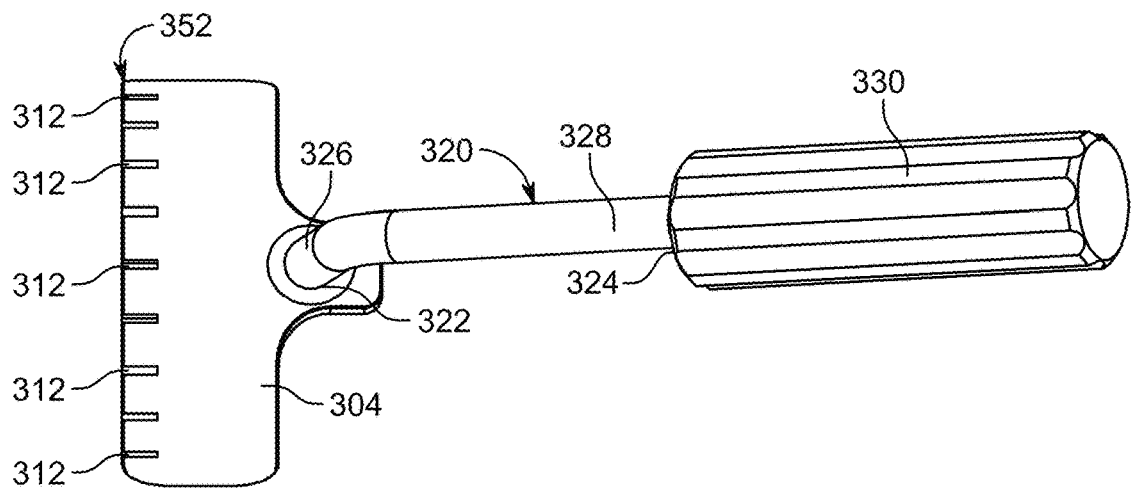
FIG. 30 is a top view of the position rotation device of FIG. 29, in accordance with an aspect of the present invention.
Figure 31:
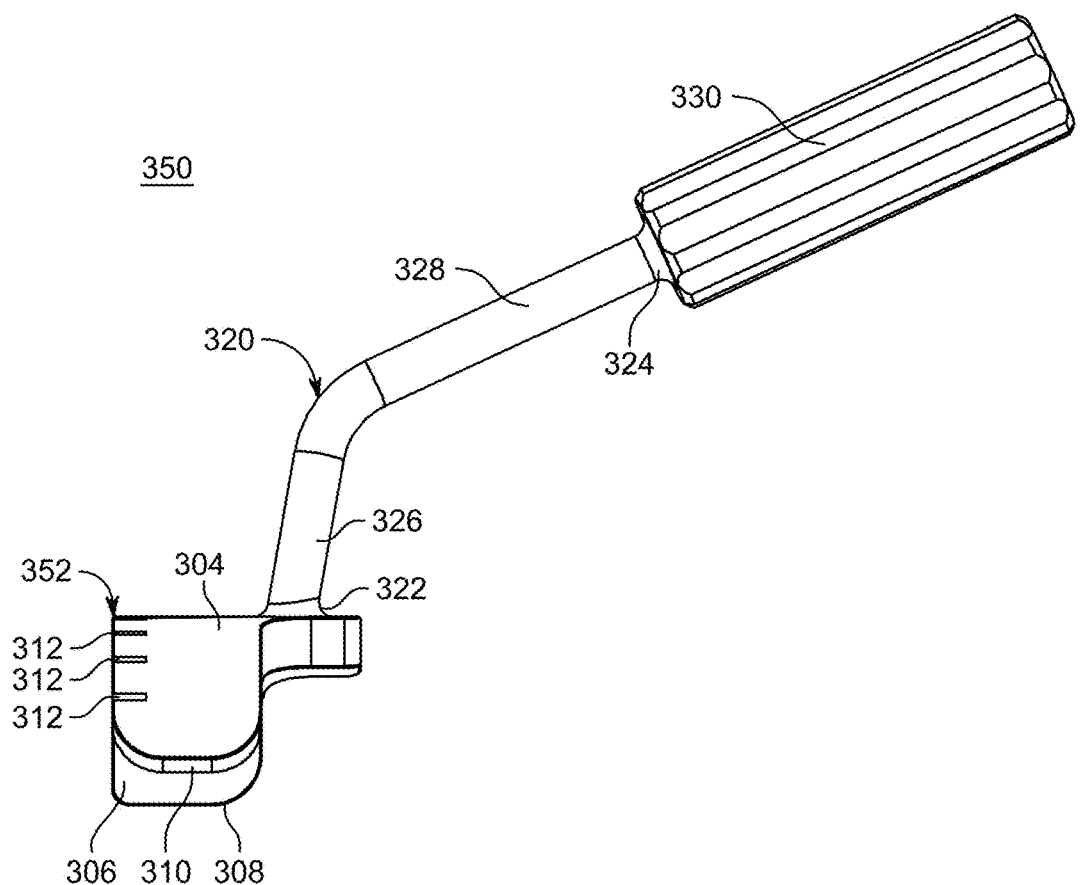
FIG. 31 is a side view of the position rotation device of FIG. 29, in accordance with an aspect of the present invention.
Figure 32:
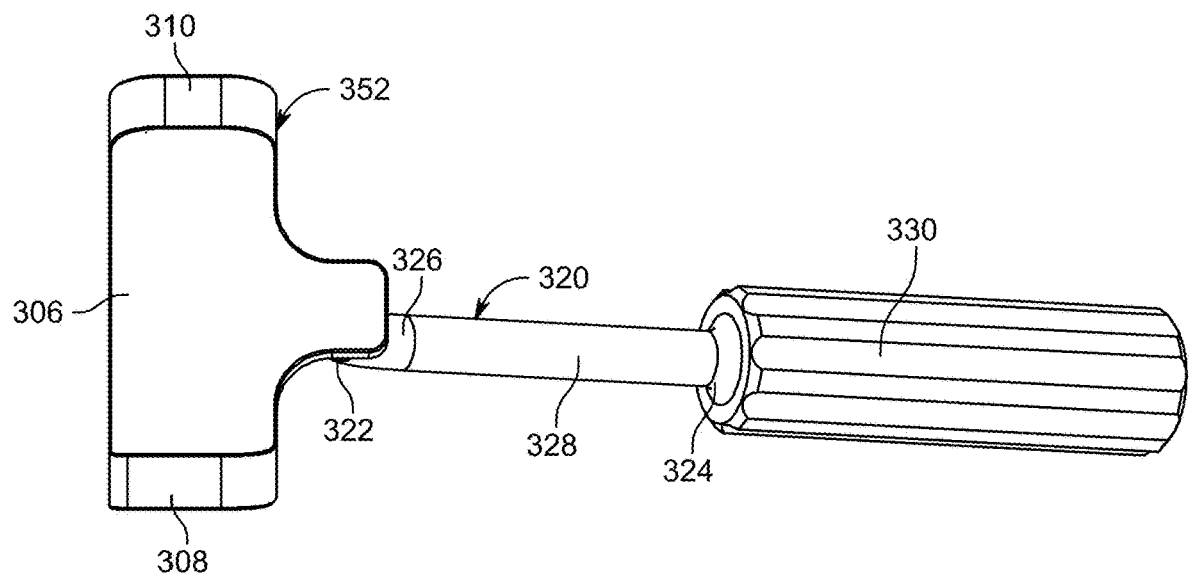
FIG. 32 is a bottom view of the position rotation device of FIG. 29, in accordance with an aspect of the present invention.
Figure 35:
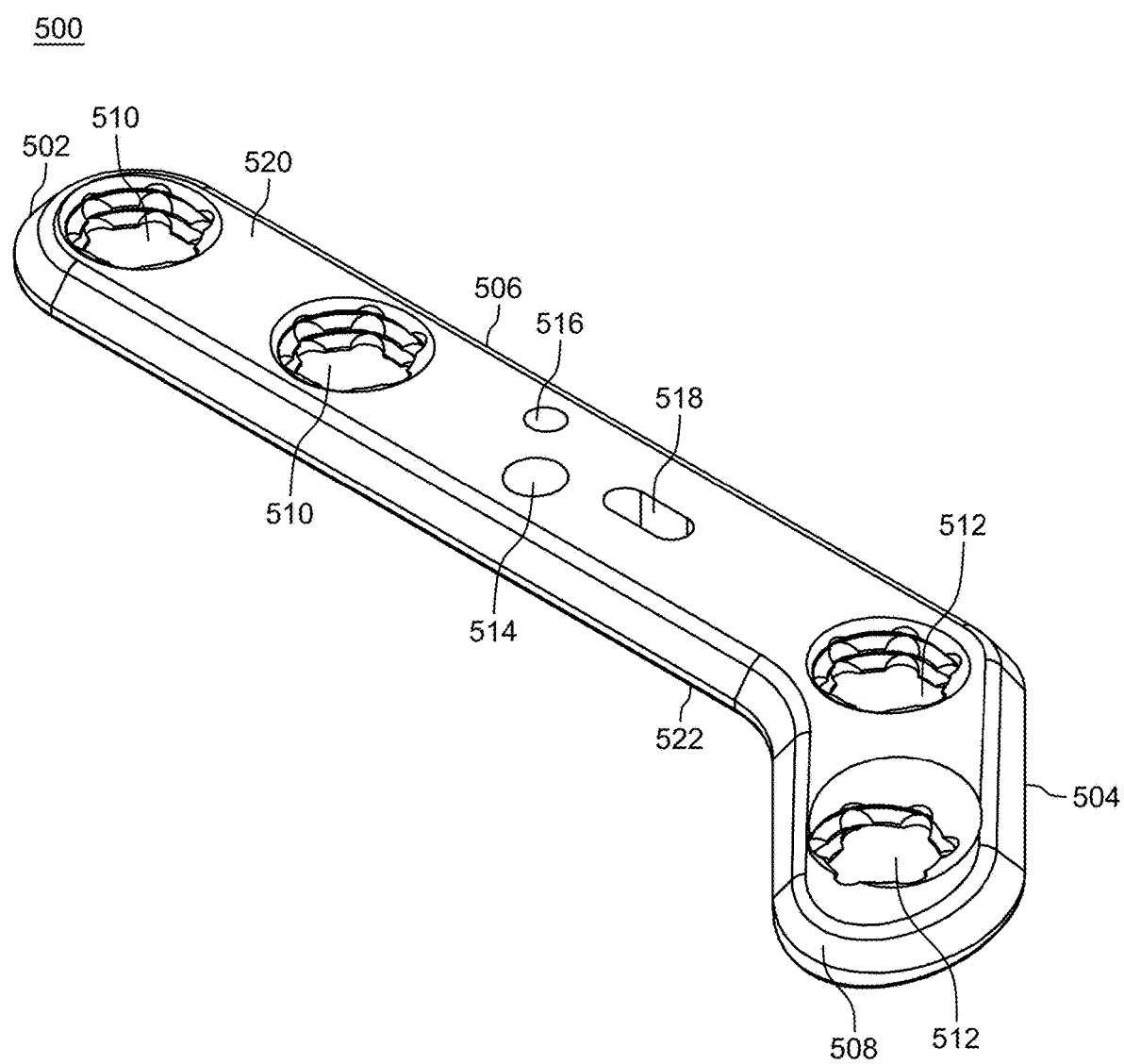
FIG. 35 is a top perspective view of a first plate, in accordance with an aspect of the present invention.
Figure 36:
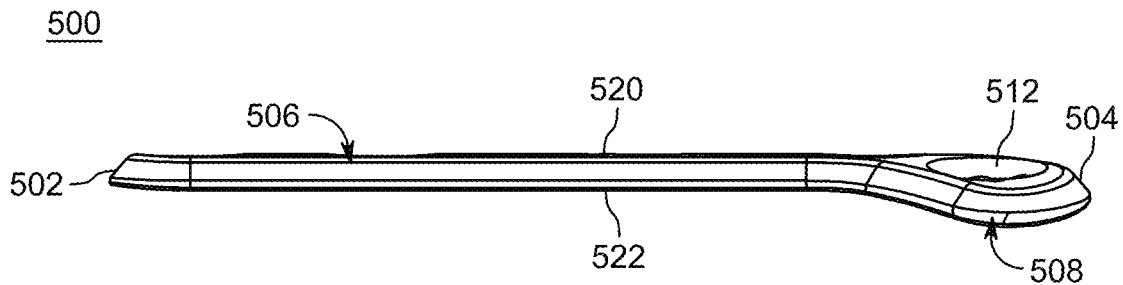
FIG. 36 is a first side view of the plate of FIG. 35, in accordance with an aspect of the present invention.
Figure 37:
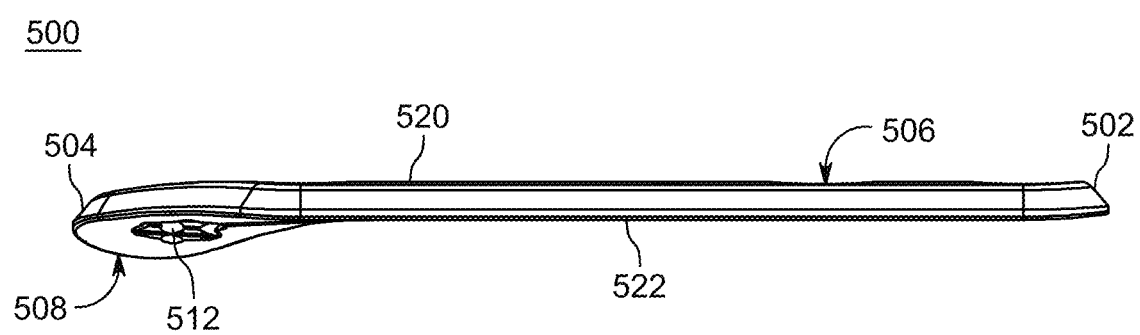
FIG. 37 is a second side view of the plate of FIG. 35, in accordance with an aspect of the present invention.
Figure 38:
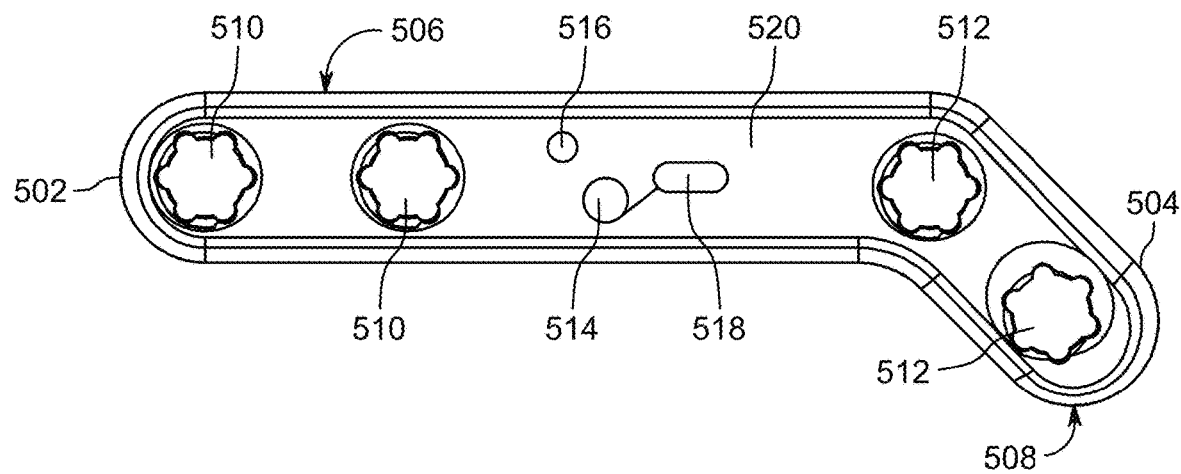
FIG. 38 is a top view of the plate of FIG. 35, in accordance with an aspect of the present invention.
Figure 39:
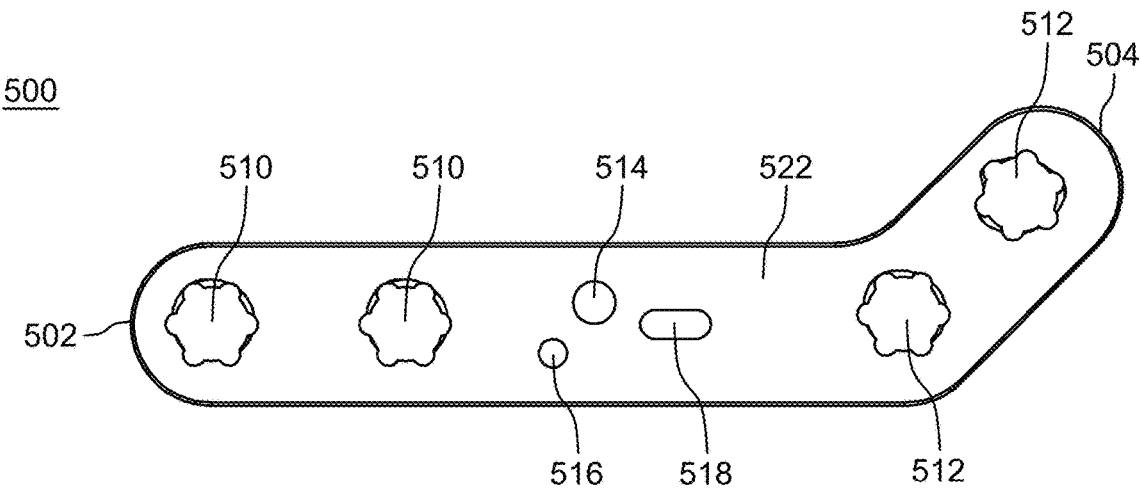
FIG. 39 is a bottom view of the plate of FIG. 35, in accordance with an aspect of the present invention.
Figure 40:
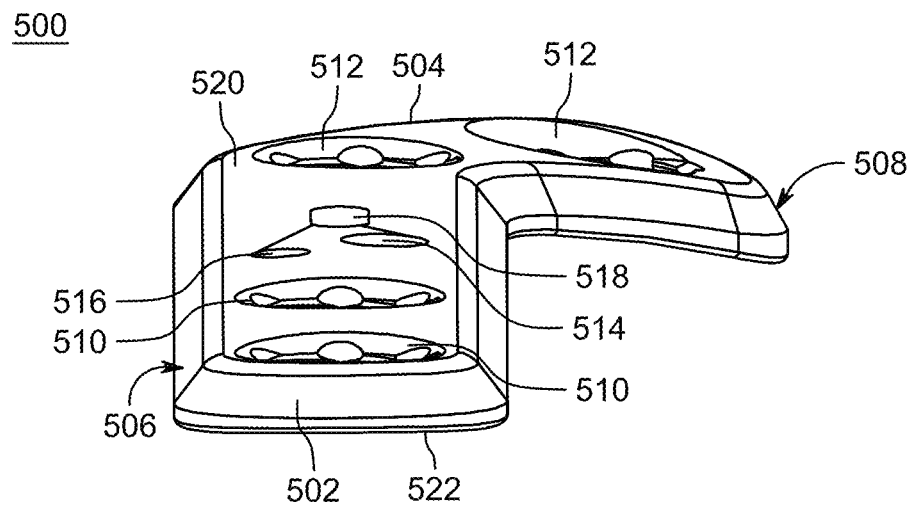
FIG. 40 is a first end perspective view of the plate of FIG. 35, in accordance with an aspect of the present invention.
Figure 41:
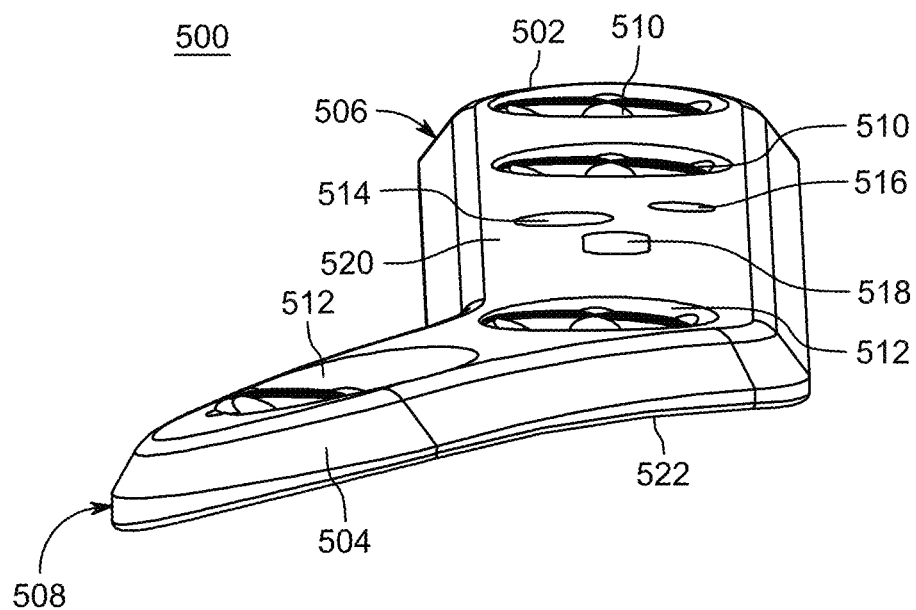
FIG. 41 is a second end perspective view of the plate of FIG. 35, in accordance with an aspect of the present invention.
Figure 42:
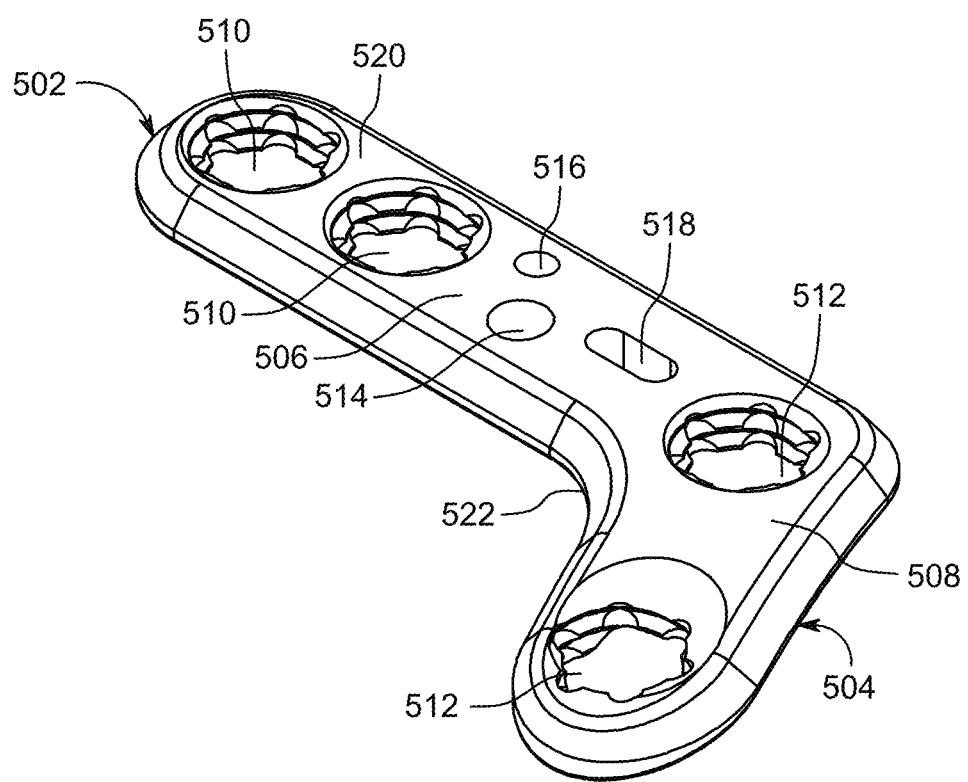
FIG. 42 is a top perspective view of a second plate, in accordance with an aspect of the present invention.
Figure 43:
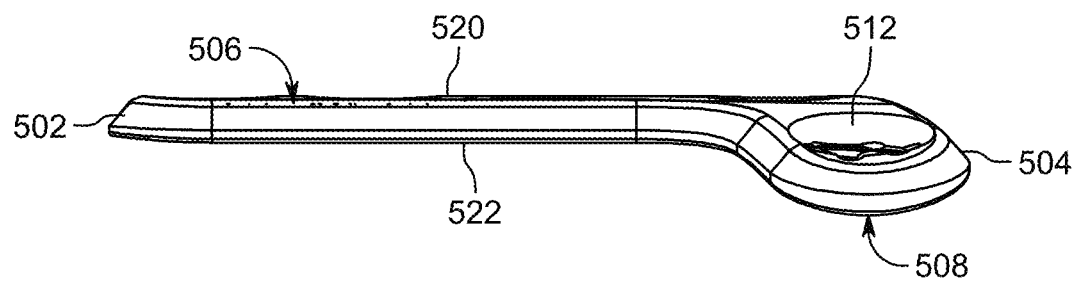
FIG. 43 is a first side view of the plate of FIG. 42, in accordance with an aspect of the present invention.
Figure 44:
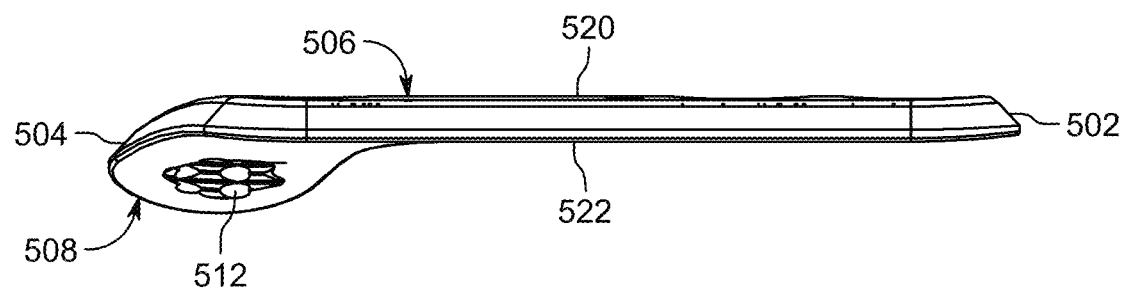
FIG. 44 is a second side view of the plate of FIG. 42, in accordance with an aspect of the present invention.
Figure 45:
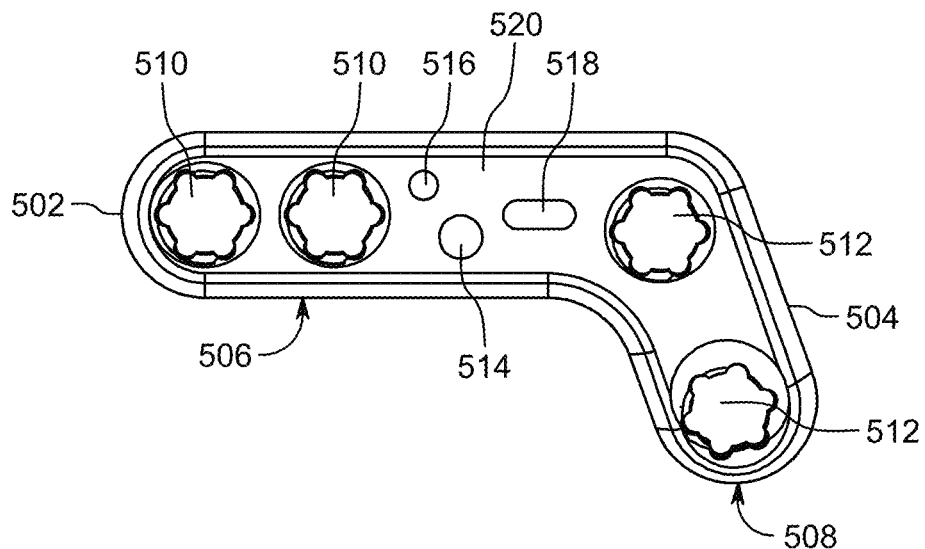
FIG. 45 is a top view of the plate of FIG. 42, in accordance with an aspect of the present invention.
Figure 46:
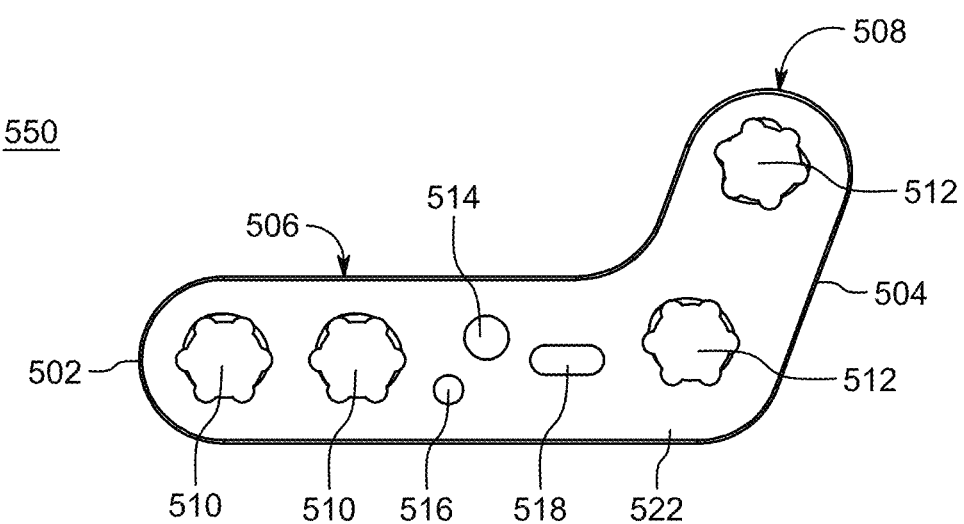
FIG. 46 is a bottom view of the plate of FIG. 42, in accordance with an aspect of the present invention.
Figure 47:
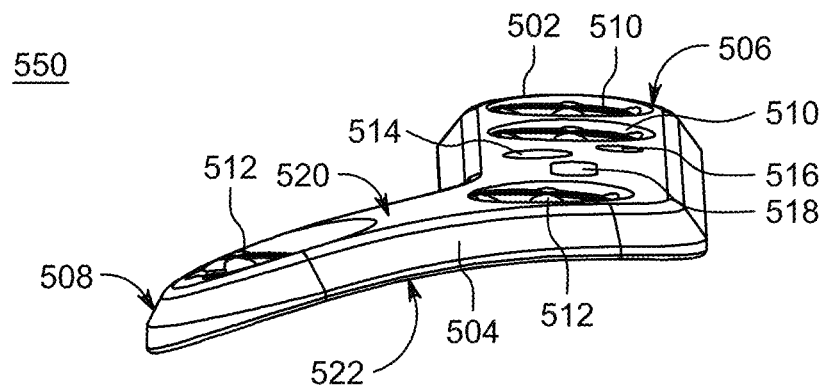
FIG. 47 is a first end perspective view of the plate of FIG. 42, in accordance with an aspect of the present invention.
Figure 48:
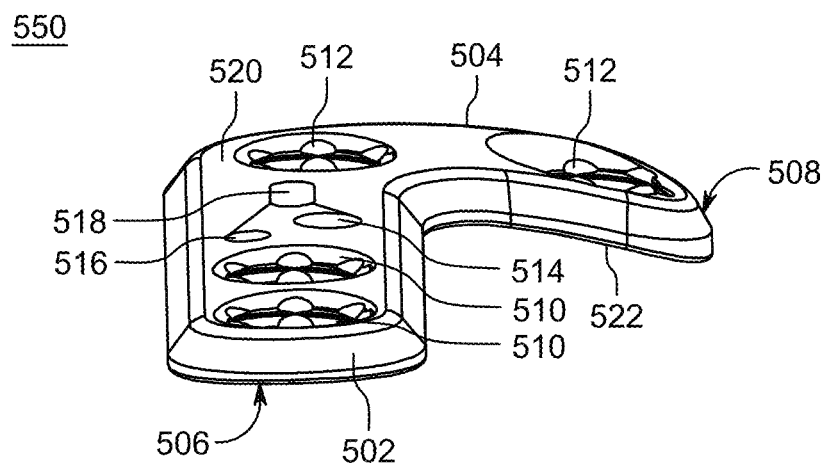
FIG. 48 is a second end perspective view of the plate of FIG. 42, in accordance with an aspect of the present invention.

The cutting guide 200 may further include a first opening 228 and a plurality of second openings 230 positioned along the second end 204, as shown in FIGS. 17-22. The second openings 230 may be, for example, positioned linearly along the curvature of the second end 204. The openings 228, 230 may be sized to receive a k-wire 410, 412. Referring now to FIG. 22, the first opening 228 may be, for example, a 0° opening, and the plurality of second openings 230 may have angles ranging from, for example, approximately 13° to 55°. In the depicted embodiment, the plurality of second openings 230 include angles of, for example, approximately 13°, 18°, 23°, 28°, 33°, 38°, 47°, and 55°.

Referring now to FIGS. 23-28, a position rotation device 300 is shown. The rotation device 300 includes a base 302 with a top surface 304, a bottom surface 306 opposite the top surface 304, a first end 308, and a second end 310. The base 302 may be, for example, curved to form a semi-circle. The base 302 may be angled along a side from the first end 308 to a center position of the base 302 and from the second end 310 to the center position forming a point inset into the base 302 at the center. The base 302 may also include a plurality of angle markings 312 positioned along a side of the base 302. The base 302 may also include an opening 354 positioned adjacent to the shaft 320. The opening 354 may be sized to receive a k-wire or fastener to secure the position rotation device 300 to a bone. The shaft 320 may include a first end 322 and a second end 324. The first end 322 may be coupled to the top surface 304 of the base 302 near a center point. The second end 324 may be coupled to a handle 330. The shaft 320 may include a first segment 326 near the first end 322 and a second segment 328 near the second end 324. The first segment 326 may be angled relative to the second segment 328.

Another position rotation device 350 is shown in FIGS. 29-34. The rotation device 300 includes a base 352 with a top surface 304, a bottom surface 306 opposite the top surface 304, a first end 308, and a second end 310. The base 352 may be, for example, curved to form a semi-circle. The base 352 may also include a plurality of angle markings 312 positioned along a side of the base 302. The side of the base 352 with the plurality of angle markings 312 may be straight from the first end 308 to the second end 310. The shaft 320 may include a first end 322 and a second end 324. The first end 322 may be coupled to the top surface 304 of the base 302 near a center point. The second end 324 may be coupled to a handle 330. The shaft 320 may include a first segment 326 near the first end 322 and a second segment 328 near the second end 324. The first segment 326 may be angled relative to the second segment 328.

Referring now to FIGS. 35-41, a first plate 500 is shown. The first plate 500 may include a first end 502 and a second end 504 opposite the first end 502. The first plate 500 may also include a first portion 506 extending from a first end 502. The plate 500 may further include a second portion 508 extending away from the first portion 506 at an angle toward the second end 504. The plate may include a top surface 520 and bottom surface 522. The first portion 506 may include at least one first opening 510. The at least one first opening 510 may extend from a top surface 520 to a bottom surface 522. The at least one first opening 510 may include a threaded portion on the interior surface of the opening 510. The threaded portion may have, for example, at least one scallop or cutout forming a break in the threads of the threaded portion. The threaded portion may be, for example, a screw hole for receiving a fastener or screw. The threaded portion and at least one cutout are shaped to lock the fastener or screw in the opening 510. The at least one first opening 510 may be tapered from the top surface 520 to the bottom surface 522 of the plate 500. Although only two first openings 510 are shown in the depicted embodiment, it is also contemplated that the first portion 506 may include, for example, more than two first openings 510 to provide for additional fastening locations to secure the first portion 506 of the plate 500 to a patient's bones.

With continued reference to FIGS. 35-41, the second portion 508 may include at least one second opening 512. The at least one second opening 512 may extend through the plate 500 from a top surface 520 to a bottom surface 522. The second opening 512 may include a threaded portion on the interior surface of the opening 512. The threaded portion may have, for example, at least one scallop or cutout forming a break in the threads of the threaded portion. The threaded portion and at least one cutout may be, for example, a screw hole for receiving a fastener or screw. The threaded portion and at least one cutout are shaped to lock the fastener or screw in the opening 512. The at least one second opening 512 may be tapered from the top surface 520 to the bottom surface 520 of the plate 500. Although only two second openings 512 are shown in the depicted embodiment, it is also contemplated that the second portion 508 may include, for example, more than two second openings 512 to provide for additional fastening locations to secure the second portion 508 of the plate 500 to the patient's bones.

The first plate 500 may also include a first alignment opening 514 and a second alignment opening 516, as shown in FIGS. 35-41. Each opening 514, 516 may be sized and shaped to receive a corresponding alignment protrusion (not shown) from a plate alignment device (not shown). For example, the opening 514 may be threaded to receive a threaded peg of the alignment device (not shown). The plate 500 may further include an alignment slot 518 which may be sized and shaped to receive a temporary fixation device (not shown) or a bone compression device (not shown). The alignment openings 514, 516 and alignment slot 518 may be positioned near a midpoint of the first portion 506 of the plate 500. As shown in FIGS. 36, 37, 40 and 41, the second portion 508 of the plate 500 may be curved as it extends away from the first portion 506. For example, the second portion 508 of the plate may be curved to match the base of the first metatarsal and the first portion 506 of the plate 500 may be curved to match the shaft of the first metatarsal. The second end 504 may be in an offset plane from the first end 502 of plate 500 such that the plate 500 matches the anatomic contour of the first metatarsal. Further, the bottom surface 522 of the plate 500 may be curved to correspond to the shape of a corrected bone.

A second plate 550 is shown in FIGS. 42-48. The second plate 550 may include a first end 502 and a second end 504 opposite the first end 502. The second plate 550 may also include a first portion 506 extending from the first end 502. The second plate 550 may further include a second portion 508 extending away from the first portion 506 at an angle toward the second end 504. The second plate 550 may include a top surface 520 and bottom surface 522. The first portion 506 may include at least one first opening 510. The at least one first opening 510 may extend through the plate 550 from a top surface 520 to a bottom surface 522. The at least one first opening 510 may include a threaded portion on the interior surface of the opening 510. The threaded portion may have, for example, at least one scallop or cutout forming a break in the threads of the threaded portion. The threaded portion may be, for example, a screw hole for receiving a fastener or screw. The threaded portion and at least one cutout are shaped to lock the fastener or screw in the opening 510. The at least one first opening 510 may be tapered from the top surface 520 to the bottom surface 522 of the plate 550. Although only two first openings 510 are shown in the depicted embodiment, it is also contemplated that the first portion 506 may include, for example, more than two first openings 510 to provide for additional fastening locations to secure the first portion 506 of plate 550 to a patient's bones.

With continued reference to FIGS. 42-48, the second portion 508 may include at least one second opening 512. The at least one second opening 512 may extend through the plate 550 from a top surface 520 to a bottom surface 522. The second opening 512 may include a threaded portion on the interior surface of the opening 512. The threaded portion may have, for example, at least one scallop or cutout forming a break in the threads of the threaded portion. The threaded portion may be, for example, a screw hole for receiving a fastener or screw. The threaded portion and at least one cutout are shaped to lock the fastener or screw in the opening 512. The at least one second opening 512 may be tapered from the top surface 520 to the bottom surface 522 of the plate 550. Although only two second openings 512 are shown in the depicted embodiment, it is also contemplated that the second portion 508 may include, for example, more than two second openings 512 to provide for additional fastening locations to secure the second portion 508 of plate 550 to a patient's bones.

The second plate 550 may also include a first alignment opening 514 and a second alignment opening 516, as shown in FIGS. 42-48. Each opening 514, 516 may be sized and shaped to receive a corresponding alignment protrusion (not shown) from a plate alignment device (not shown). For example, the opening 514 may be threaded to receive a threaded peg of the alignment device (not shown). The second plate 550 may further include an alignment slot 518 which may be sized and shaped to receive a temporary fixation device (not shown) or a bone compression device (not shown). The alignment openings 514, 516 and alignment slot 518 may be positioned near a midpoint of the first portion 506 of the second plate 550. As shown in FIGS. 43, 44, 47 and 48, the second portion 508 of the second plate 550 may be curved as it extends away from the first portion 506. For example, the second portion 508 of the plate may be curved to match the base of the first metatarsal and the first portion 506 of the plate 550 may be curved to match the shaft of the first metatarsal. The second end 504 may be in an offset plane from the first end 502 of plate 550 such that plate 550 matches the anatomic contour of the first metatarsal. Further, the bottom surface 522 of the second plate 550 may be curved to correspond to the shape of a corrected bone. The first plate 500 may be longer than the second plate 550.

Although only two plates 500, 550 are shown, it is contemplated that the plates 500, 550 may be available in varying lengths to correspond to the varying angles of the osteotomy and the vertical inclination angles. As would be understood by one of ordinary skill in the art, as the vertical inclination angle increases, the cut will correspondingly be longer, thus needing a longer plate 500, 550 for proper placement along the bones. As the size of the plate 500, 550 increases, the positions of the openings 510, 512, alignment openings 514, 516, and alignment slot 518 may vary to correctly position the alignment device 900 on the plate 500, 550 and the openings 510, 512 on the bone portions.

A surgical method using the osteotomy system is shown in FIGS. 49-58. The method may include exposing the bone with a deformity and placing the alignment device onto the bone. The method may also include inserting a first k-wire into a first opening in the alignment device and determining the rotation angle for the bone. In addition, the method may include selecting a second opening in the alignment device that corresponds to the rotation angle and inserting a second k-wire into the second opening in the alignment device. The method may further include removing the alignment device and the first k-wire and obtaining a cut guide. The method may also include determining the hole in the cut guide that corresponds to the osteotomy cut angle and sliding the selected hole of the cut guide over the second k-wire. The method may include fixing the cut guide to the bone along the axis of the bone with a k-wire or fixation device and obtaining a sagittal saw blade. Further, the method may include inserting the saw blade through a slot in the cut guide to cut the bone and removing the securement k-wire, second k-wire and cut guide. The method may also include completing a cut of the bone and obtaining a rotation device. In addition, the method may include positioning the rotation device on the cut bone and rotating the distal end of the bone with respect to the proximal end to the desired angle of rotation on the rotation device. Optionally, the second k-wire may be left in the patient's bone, the rotation device may be slid onto the second k-wire to assist with the rotation of the distal end of the bone, and then the second k-wire may be removed. Finally, the method may include securing rotated bone with a plate and/or cross screw and closing the patient's incision.

The surgical method is a proximal rotational metatarsal osteotomy performed through a proximal metatarsal oblique plane osteotomy correcting the deformity through rotation. The surgical method may correct a metatarsal internal rotation and the hallux valgus deformity by rotating the metatarsal through an oblique plane with no bone resection. The surgical procedure may be performed with no loss of metatarsal length and a broader bone surface contact exists than on a transverse proximal osteotomy. The surgical procedure also may allow for correcting a transverse plane deformity by locating the metatarsal parallel to the second metatarsal and correcting an axial plane deformity, i.e. malrotation, to position the bone on top of the sesamoids. The surgical method performs a complete transverse and coronal plane deformity correction.

The hallux valgus surgery is performed to relocate the first metatarsal 400 above the sesamoids. First, the intermetatarsal angle is measured to evaluate the severity of the deformity on an anterior-posterior foot x-ray. The intermetatarsal angle is obtained by measuring the divergence between the first and second metatarsals. Next, the angle to be corrected is measured to determine the degrees necessary to place the metatarsal head over the sesamoid complex. There may be a limited capacity to evaluate the metatarsal malrotation, due to sesamoid subluxation. In one embodiment, axial sesamoid x-rays can give a rough estimate of first ray malrotation. In another embodiment, a preoperative CT scan is performed, which could assess metatarsal rotation and sesamoid subluxation. In another embodiment, the metatarsal rotation angle may be assessed by measuring the angle between the floor and hallux with a goniometer.

Once the intermetatarsal angle and rotation angle are determined, then the angle of correction or osteotomy cut angle may be determined. The rotational orientation of the osteotomy or rotation angle may be determined using the following formula: Rotation Angle=R/2. The intermetatarsal angle is represented by "A". The angle of correction may be determined using, for example, the following formula: Osteotomy Cut Angle=arctan[sin (A/2)/tan (R/2)]. For example, a 30 degree great toe internal rotation with a 15 degree intermetatarsal angle may be corrected to 15 degrees of varus angulation to leave both metatarsals parallel and 30 degrees of internal rotation. In order to avoid having to perform calculations during surgery, the angle of correction or osteotomy cut angle may be determined using Table 1 or Table 2 below. Table 1 and Table 2 include commonly seen values for rotation angle and common intermetatarsal angles. In addition, Table 1 includes the actual osteotomy cut angles calculated using the above formulas. In another embodiment, the angle of correction may be determined using the following formula: Osteotomy Cut Angle or Vertical Inclination Angle=arctan[sin (A/2)/tan (R/2)]+α. The value of α may be, for example, approximately −10° to 25° and more specifically, −8° to 21°. The value α accounts for rounding of the vertical inclination angles to provide a reasonable number of corresponding openings in the alignment devices. An example of this alternative formula is shown in Table 2, which further simplifies Table 1 by grouping similar values together to reduce the number of openings 230 required in the cut guide 200. Therefore, it is also contemplated that in alternative embodiments the osteotomy cut angles listed in Table 2 may be different based on an alternative grouping of osteotomy cut angles. If there is a remaining interphalangeal deformity, then an optional phalangeal osteotomy, for example, an Akin osteotomy, may be performed.

TABLE 1

|  |  | Rotation Angle | | | |
|---|---|---|---|---|---|
|  |  | 15° | 30° | 45° | 60° |
| Intermetatarsal Angle | 12° | 38 | 21 | 14 |  |
|  | 15° | 45 | 26 | 17 | 13 |
|  | 17° | 48 | 29 | 20 | 14 |
|  | 20° | 53 | 33 | 23 | 17 |
|  | 25° | 59 | 39 | 28 | 21 |

TABLE 2

|  |  | Rotation Angle | | | |
|---|---|---|---|---|---|
|  |  | 15° | 30° | 45° | 60° |
| Intermetatarsal Angle | 12° | 38 | 23 | 13 |  |
|  | 15° | 47 | 28 | 18 | 13 |
|  | 17° | 47 | 28 | 18 | 13 |
|  | 20° | 55 | 33 | 23 | 18 |
|  | 25° | 55 | 38 | 28 | 23 |

In another embodiment as shown in Table 3, the angle of correction may be determined using the following formula: Osteotomy Cut Angle or Vertical Inclination Angle=arctan[sin (A/2)/tan (R/2)]. The formula of Table 3 may be calculated using an average value for each range of intermetatarsal angles and an average value for each range of rotation angles. The values of Table 3 may be rounded up only to the nearest whole number to obtain the osteotomy cut angle or vertical inclination angle. In yet another embodiment as shown in Table 4, the angle of correction may be determined using the following formula: Osteotomy Cut Angle or Vertical Inclination Angle=arctan[sin (A/2)/tan (R/2)]+β. The value of β may be, for example, approximately −20° to 15° and, more specifically −16° to 9°. The value β accounts for an additional factor to be added to provide a reasonable number of corresponding openings in the alignment device. In order to avoid having to perform calculations during surgery, the angle of correction or osteotomy cut angle may be determined using, for example, Table 3 or Table 4 below. If there is a remaining interphalangeal deformity then an optional phalangeal osteotomy, for example, an Akin osteotomy, may be performed.

TABLE 3

|  |  | Rotation Angle | | | |
|---|---|---|---|---|---|
|  |  | 10-19° | 20-29° | 30-39° | 40-50° |
| Intermetatarsal Angle | 8-10° | 31 | 19 | 14 | 11 |
|  | 11-12° | 38 | 25 | 18 | 14 |
|  | 13-14° | 43 | 29 | 21 | 16 |
|  | 15-17° | 47 | 32 | 24 | 19 |
|  | 18-20° | 51 | 37 | 28 | 22 |

TABLE 4

|  |  | Rotation Angle | | | |
|---|---|---|---|---|---|
|  |  | 10-19° | 20-29° | 30-39° | 40-50° |
| Intermetatarsal Angle | 8-10° | 31 | 19 | 15 | 15 |
|  | 11-12° | 39 | 27 | 19 | 15 |
|  | 13-14° | 43 | 31 | 23 | 15 |
|  | 15-17° | 47 | 31 | 23 | 23 |
|  | 18-20° | 47 | 39 | 27 | 23 |

Figure 49:
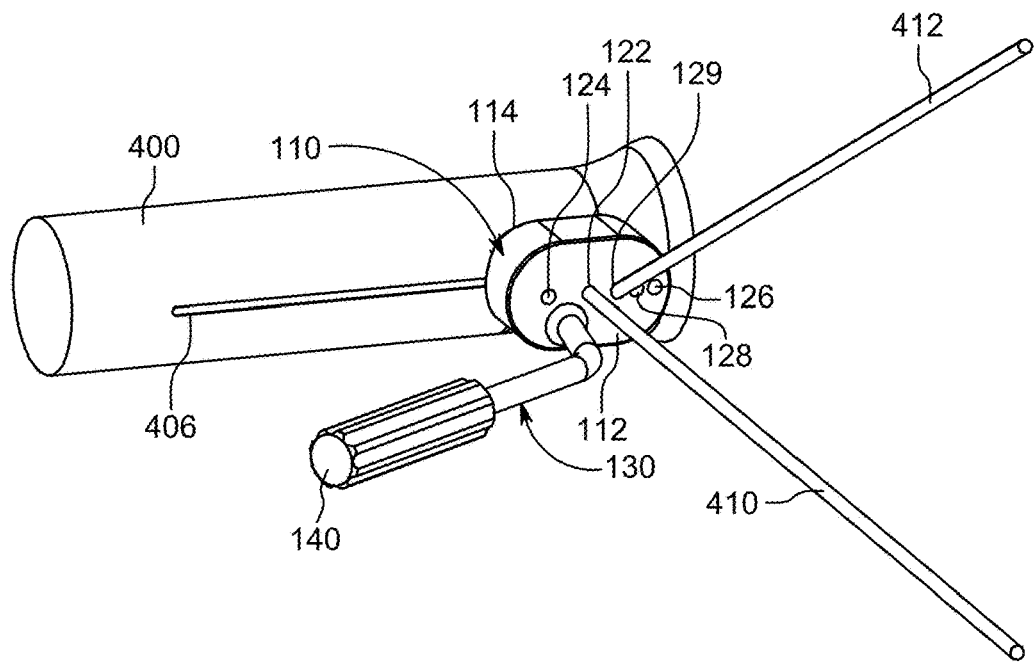
FIG. 49 is a perspective view of the alignment device of FIG. 1 positioned on a bone, in accordance with an aspect of the present invention.
Figure 50:
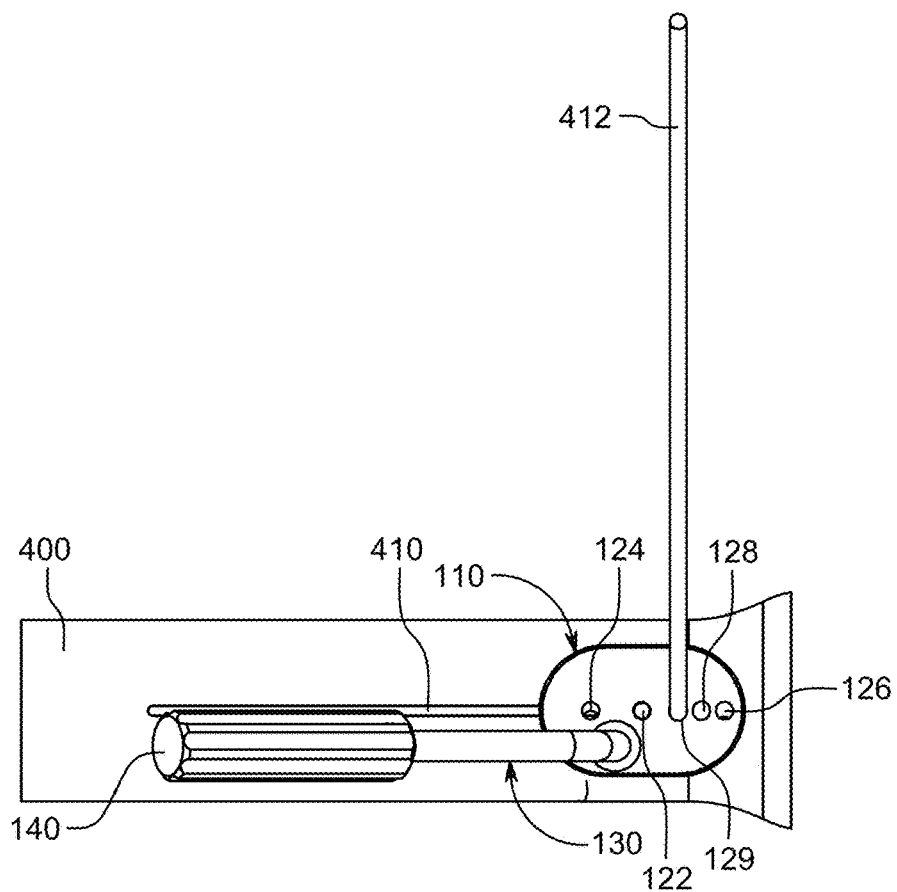
FIG. 50 is a side view of FIG. 49, in accordance with an aspect of the present invention.
Figure 51:
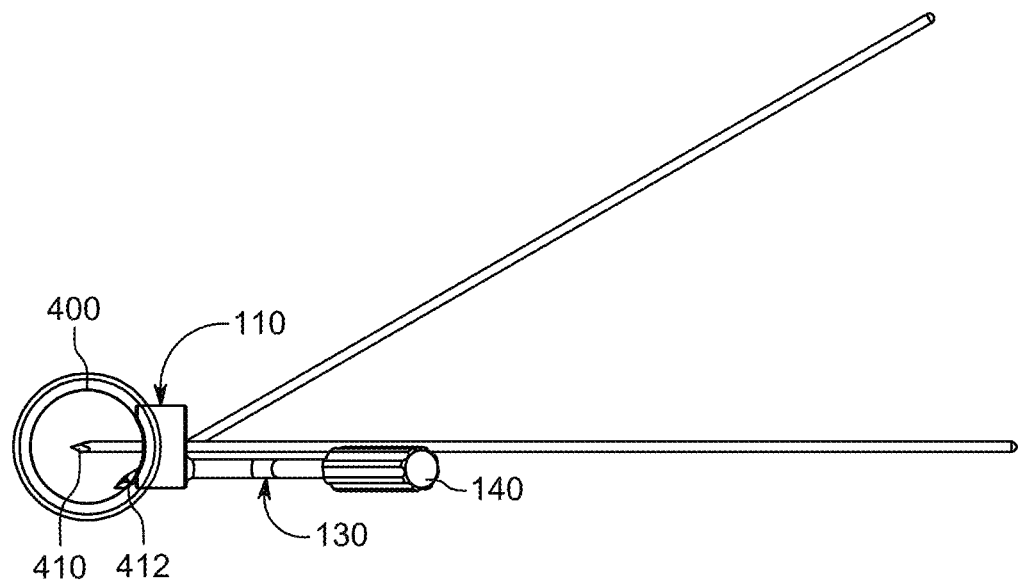
FIG. 51 is an end view of FIG. 49 with a transparent bone, in accordance with an aspect of the present invention.

Once the correction is determined, a transarticular capsulotomy through a medial approach may be performed. After the proximal metatarsal is exposed, a medial mid-axis line 406 may be drawn on the bone 400 using an electrocautery or marking pen, as shown in FIGS. 49 and 50. The first opening 122 of the alignment device 100 may be positioned over the mid-axis line 406 on the bone 400. As shown in FIGS. 49 and 50, the first k-wire 410 may then be inserted through the first opening 122 in the alignment device 100 into the bone 400. The angle of insertion of the first k-wire 410 may be, for example, dorsal-distal to plantar-proximal, as shown in FIG. 51. In another embodiment, the angle of insertion of the first k-wire 410 may be, for example, parallel to the floor and perpendicular to the midline of the bone. Based on the determined angle of correction, a second k-wire 412 may be inserted into the opening 124, 126, 128, 129 that corresponds to half the rotation angle from Table 1, as shown in FIGS. 49 and 50. In the depicted embodiment, the second k-wire 412 is inserted into the fourth angled opening 129. The angle of insertion of the second k-wire 412 may be, for example, medial to lateral, as shown in FIG. 51.

Figure 52:
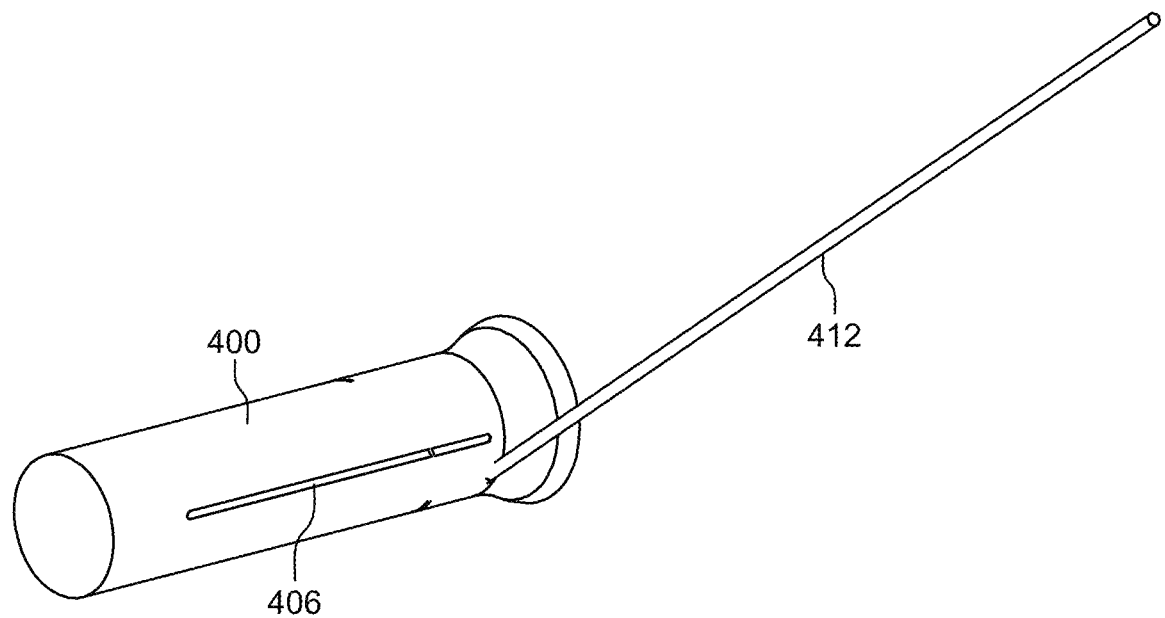
FIG. 52 is a perspective view of the bone and one k-wire of FIG. 49, in accordance with an aspect of the present invention.
Figure 53:
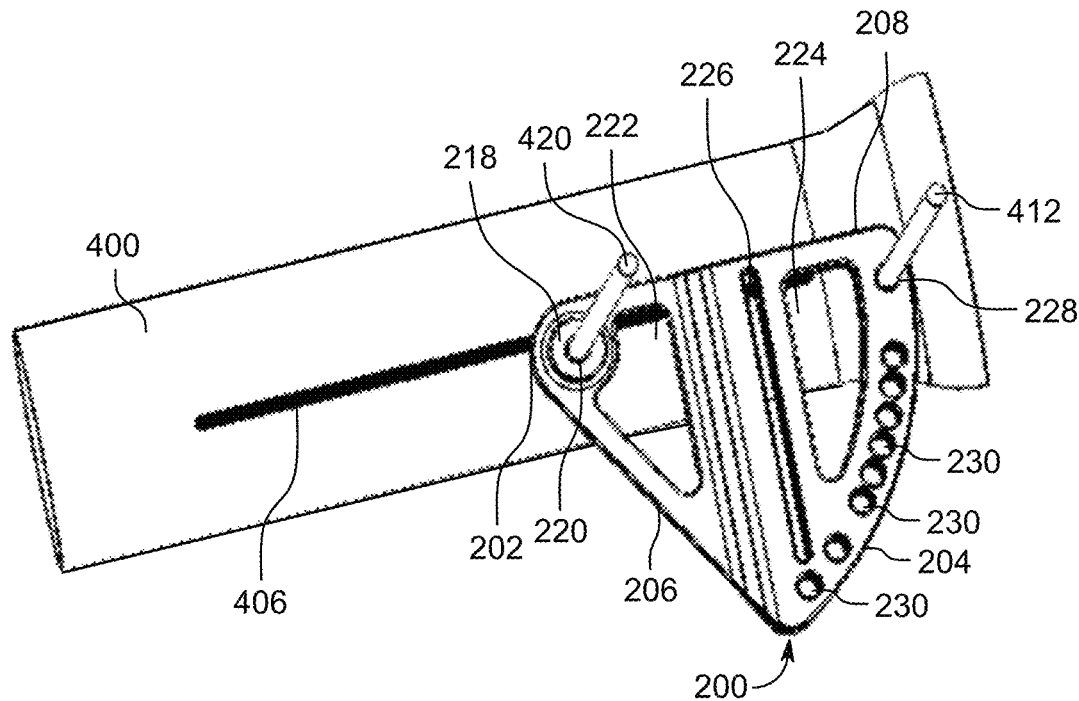
FIG. 53 is a perspective view of the bone and k-wire of FIG. 49 with a cut guide in a first position and a k-wire, in accordance with an aspect of the present invention.

Next, as shown in FIG. 52, the alignment device 100 and first k-wire 410 may be removed from the bone 400. The second k-wire 412 remains in the bone 400. As shown in FIG. 53, the cut guide 200 may then be inserted over the second k-wire 412 by, for example, sliding the zero opening 228 of the cut guide 200 onto the second k-wire 412. Once the cut guide 200 is positioned on the bone 400, the opening 220 at the first end 202 may be aligned with the mid-axis line 406. When the cut guide 200 is positioned the slot 226 should be generally perpendicular to the mid-axis line 406. Next, a securement k-wire 420 may be inserted into the opening 220, as shown in FIG. 53.

Figure 54:
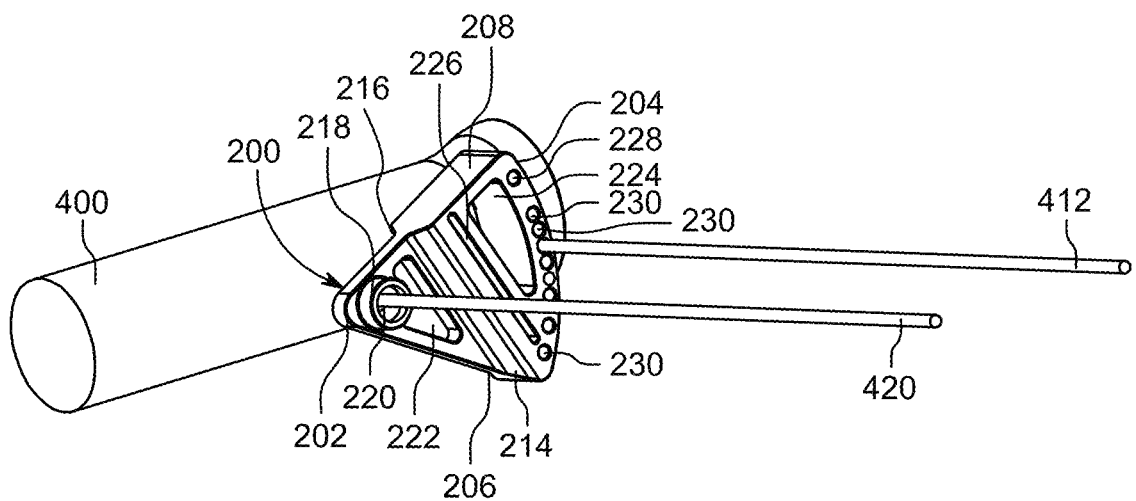
FIG. 54 is a perspective view of FIG. 53 with the cut guide in a second position, in accordance with an aspect of the present invention.
Figure 55:
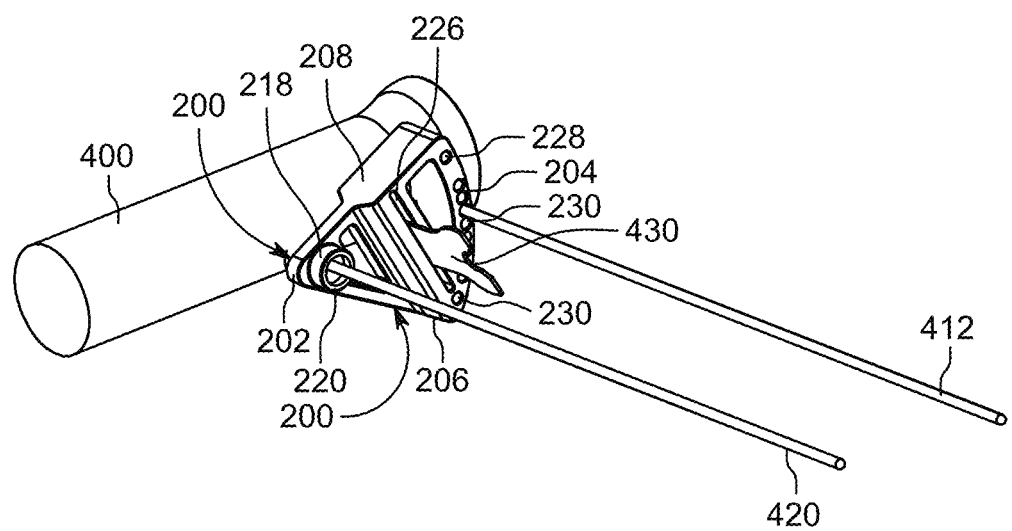
FIG. 55 is a perspective view of the cut guide of FIG. 54 with a saw inserted through the cut guide and into the bone, in accordance with an aspect of the present invention.
Figure 56:
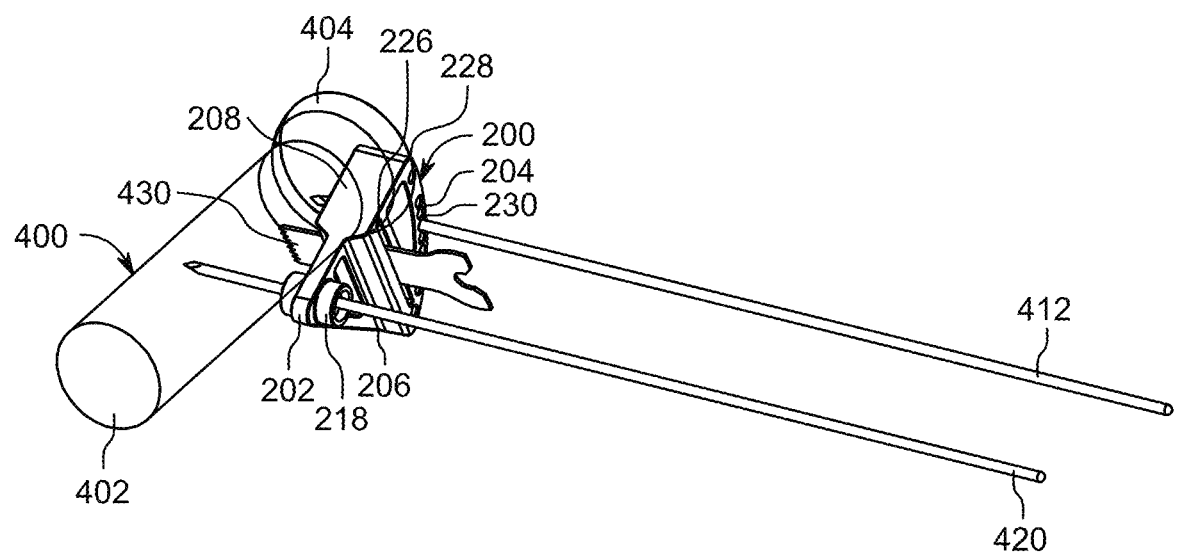
FIG. 56 is an end perspective view of FIG. 55 with a transparent bone, in accordance with an aspect of the present invention.
Figure 57:
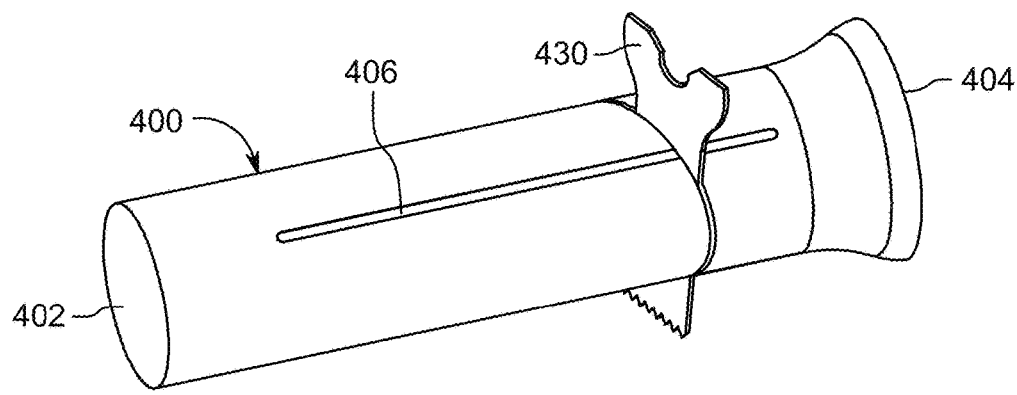
FIG. 57 is a perspective view of the bone and saw of FIG. 56 with the saw inserted through the bone, in accordance with an aspect of the present invention.

After the securement k-wire 420 is positioned, the cut guide 200 may be removed and replaced along the desired osteotomy cut angle, as shown in FIG. 54. The plurality of openings 230 may correspond to the varying osteotomy cut angles, for example, as shown in FIG. 22. Once the osteotomy cut angle is selected, the second k-wire 412 may be inserted into the selected one of the plurality of openings 230 that corresponds to the selected angle of correction or osteotomy cut angle. Once the cut guide 200 is positioned on the bone 400 at the desired correction angle, a saw 430, for example, a microsagittal saw, may be inserted into the cutting slot 226 of the cut guide 200, as shown in FIGS. 55 and 56. The bone 400 may then be cut by the saw 430 to form a first bone segment 402 and a second bone segment 404. If necessary, the k-wire 412 and securement k-wire 420 may be bent for access to the bone 400. As shown in FIG. 57, the cut of the bone 400 may be completed after removal of the cut guide 200 and optionally the k-wire 412 and securement k-wire 420.

Figure 58:
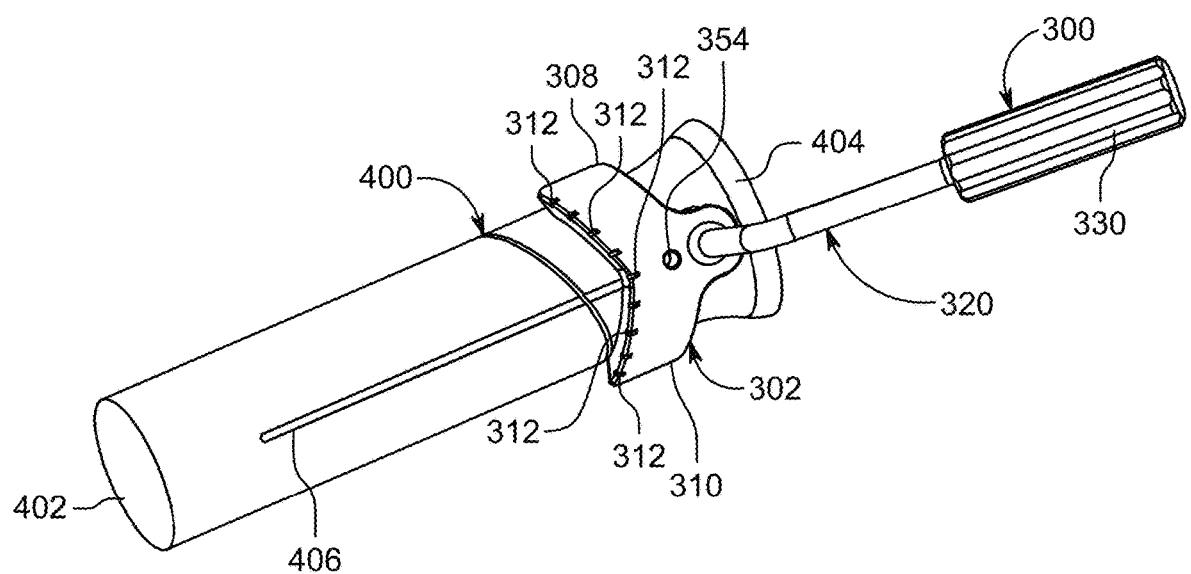
FIG. 58 is a perspective view of a position rotation device positioned on the bone of FIG. 57, in accordance with an aspect of the present invention.

Once the osteotomy is performed and the bone 400 is separated into a first bone segment 402 and a second bone segment 404, an instrument, for example, a field clamp or backhaus, may be used to grab the distal loose end 402 of the bone 400. Alternatively, if the k-wire 412 is left in the bone 400 the k-wire 412 may be used to grab the distal loose end 402. The position rotation device 300 may then be positioned on the bone 400, as shown in FIG. 58. If the k-wire 412 remains in the bone 400, then the opening 354 of the position rotation device 300 may be slid over the k-wire 412 to position the device 300. After the rotation device 300 is on the bone 400, the first bone segment 402 or distal end 402 of bone 400 may be rotated to the identified malrotation angle as indicated by the selected angle marking 312. Next, a k-wire (not shown) may be inserted perpendicularly through the osteotomy, as perpendicular as possible, for transient fixation. Another k-wire (not shown) may be inserted through the osteotomy to improve the temporary fixation stability. The deformity correction may then be checked using imaging to confirm that the first and second metatarsals are parallel. To secure the bone 400 a fastener, for example, a lag screw, may be inserted into the bone 400. Alternatively or in addition to the fastener, a bone plate 500, 550 may be positioned on and secured to the bone 400. After the bone is secured any k-wires that remain in the bone 400 may be removed. When necessary, depending on the interphalangeal angle and metatarsophalangeal soft tissue balance, an Akin osteotomy may be performed to complete the correction. Finally, the final toe rotation may be checked and once the desired rotation is achieved the patient may be closed.

Referring now to FIGS. 59-106, another osteotomy system is shown. The devices of the osteotomy system are shown in FIGS. 59-87. A method of using the devices of the osteotomy system on a patient is shown in FIGS. 88-106. The osteotomy system may include, for example, an alignment device 600, a cut guide 700, a position rotation device 800, an alignment guide 900, a plate 1000, a foot plate k-wire guide 1100, k-wires or fixation devices, an electric oscillating microsagittal saw or alternative saw 1200, bone screws 1162, 1164, 1166, 1168, and a compression fastener 1160.

Figure 61:
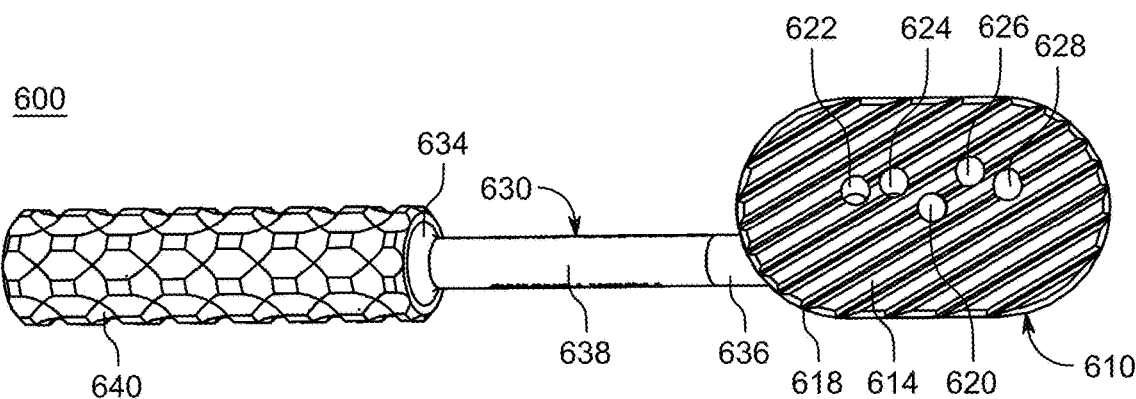
FIG. 61 is a bottom view of the alignment device of FIG. 59, in accordance with an aspect of the present invention.
Figure 62:
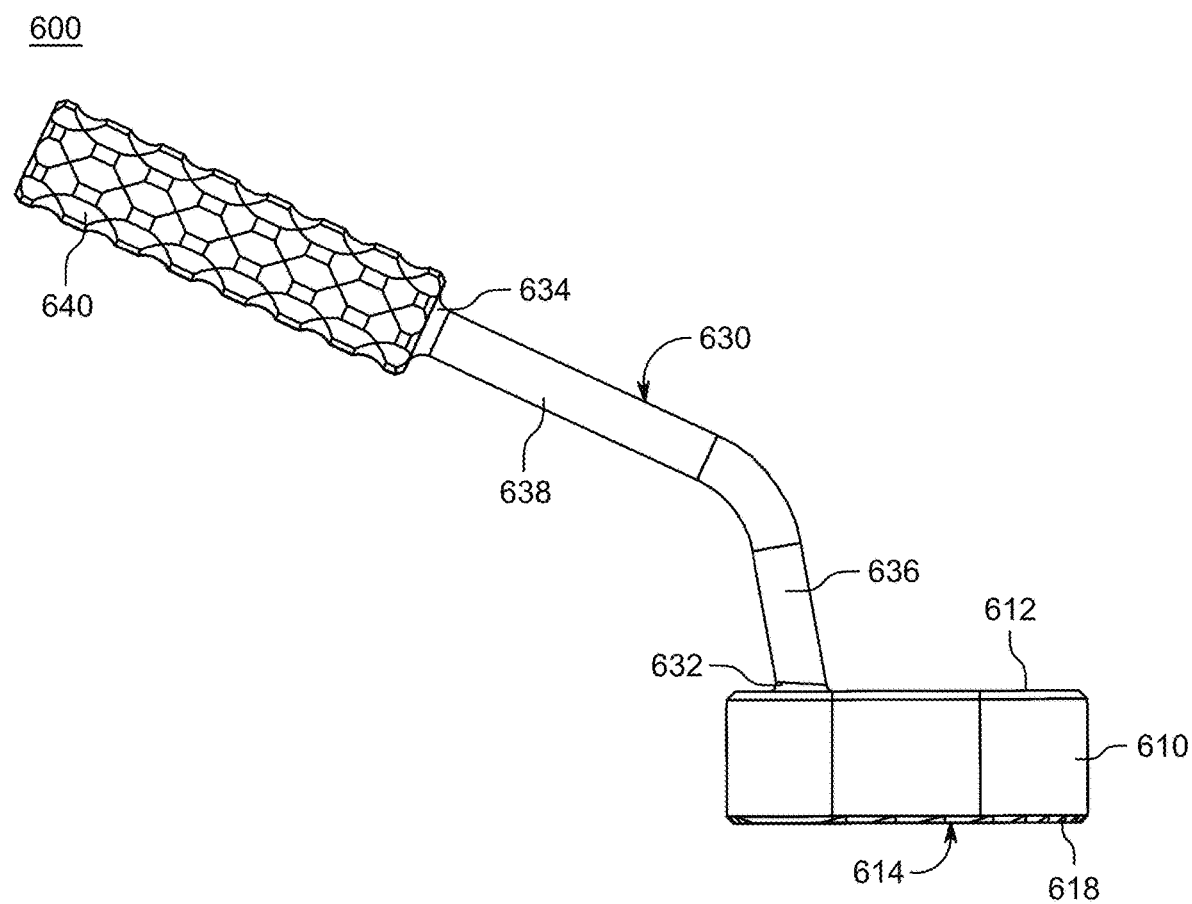
FIG. 62 is a side view of the alignment device of FIG. 59, in accordance with an aspect of the present invention.
Figure 63:
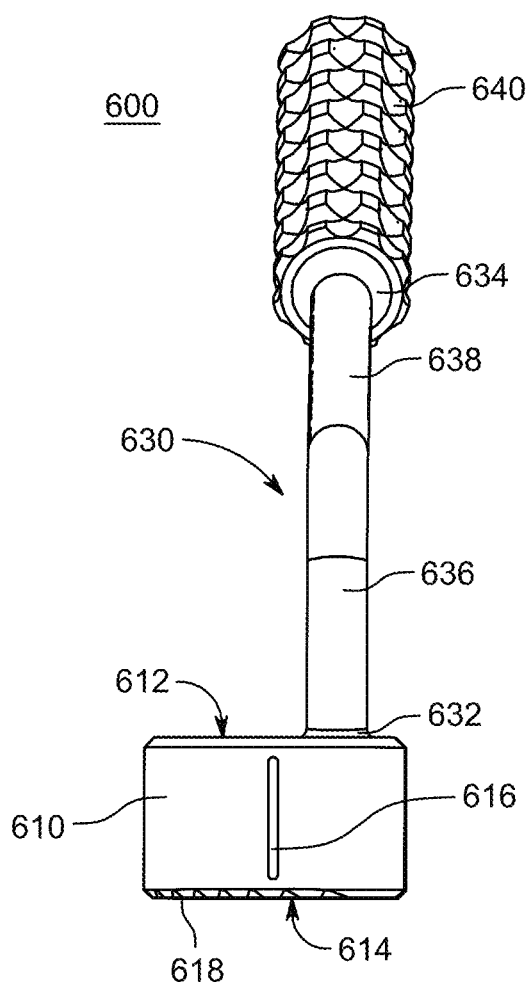
FIG. 63 is a front end view of the alignment device of FIG. 59, in accordance with an aspect of the present invention.
Figure 64:
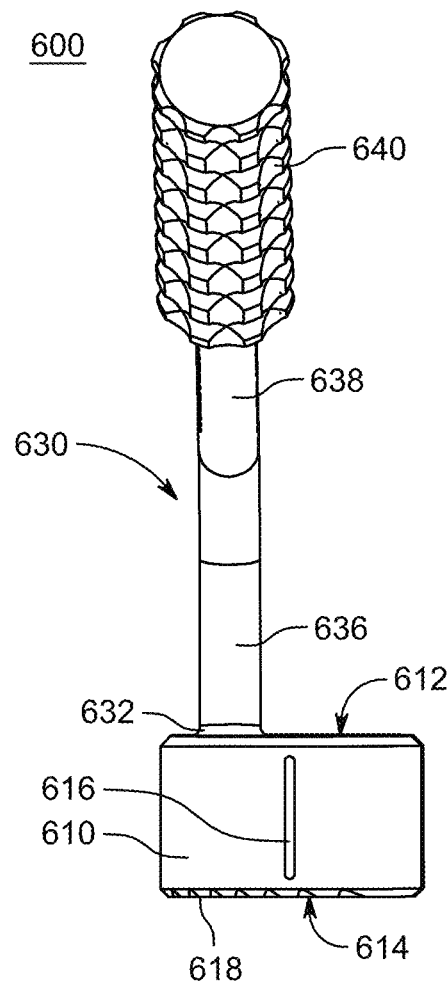
FIG. 64 is a back end view of the alignment device of FIG. 59, in accordance with an aspect of the present invention.
Figure 65:
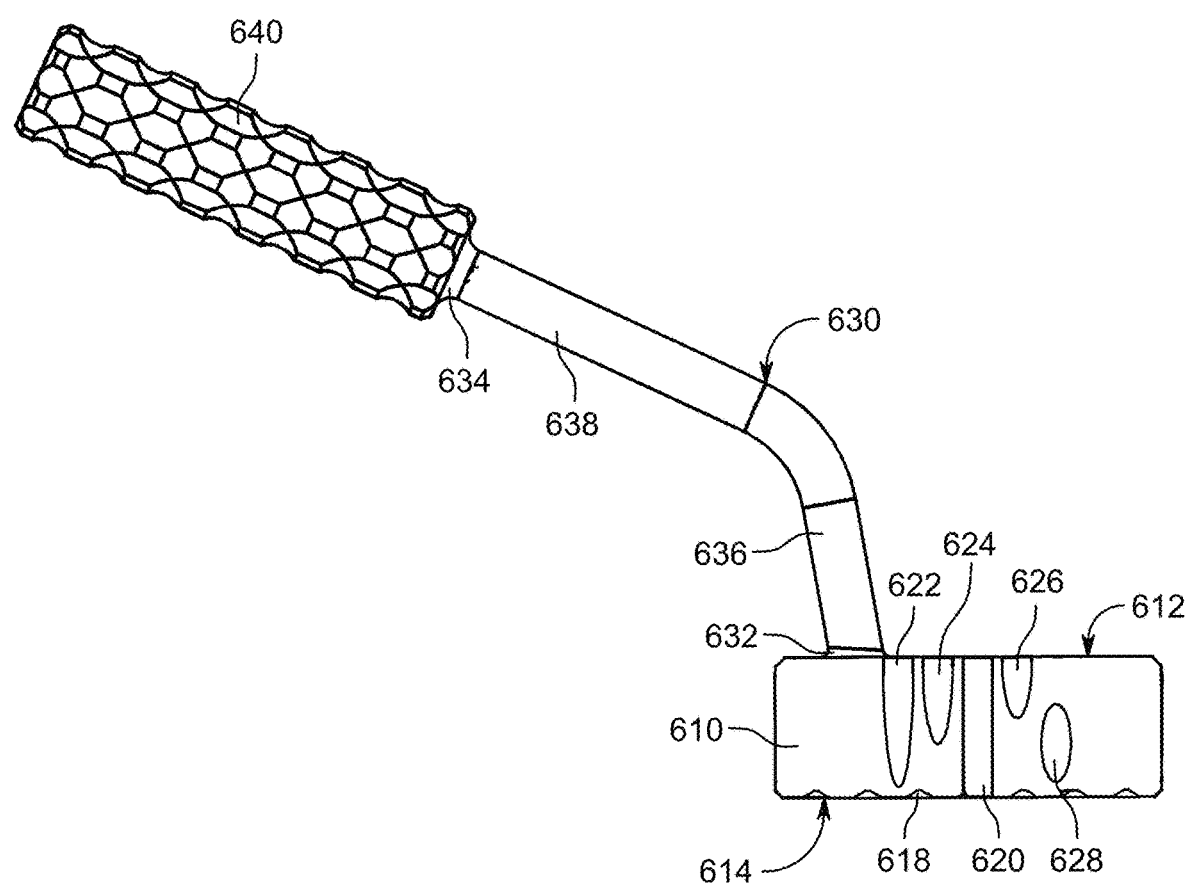
FIG. 65 is a cross-sectional side view of the alignment device of FIG. 60 taken along line 65-65, in accordance with an aspect of the present invention.
Figure 66:
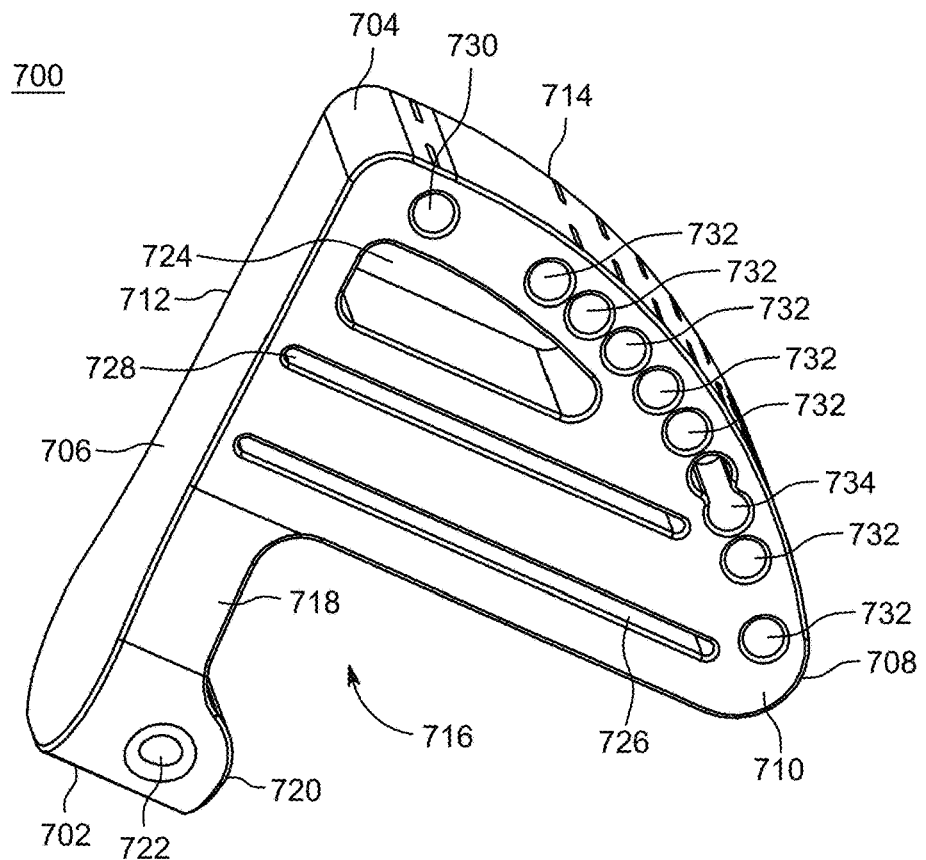
FIG. 66 is a first side perspective view of another embodiment of a cut guide, in accordance with an aspect of the present invention.

The alignment device 600 is shown in FIGS. 59-65. The alignment device 600 may include a base 610, a shaft 630 coupled to the base 610, and a handle 640 coupled to the shaft 630. The base 610 may include a top surface 612 and a bottom surface 614. The base 610 may also include at least one alignment marking 616. The at least one alignment marking 616 may be positioned on, for example, the top surface 612 or a side surface of the base 610. In an embodiment shown in FIGS. 59, 60, 63 and 64, the at least one alignment marking 616 is, for example, two alignment markings 616 positioned on the top surface 612, an alignment marking 616 positioned on a front side of the base 610, and an alignment marking 616 positioned on a rear side of the base 610. The two alignment markings 616 positioned on the top surface 612 may include a first alignment marking 616 positioned at the proximal end and a second alignment marking 616 positioned at the distal end. As best seen in FIG. 61, the bottom surface 614 may be, for example, textured or include a plurality of grooves or other surface contours 618.

Figure 59:
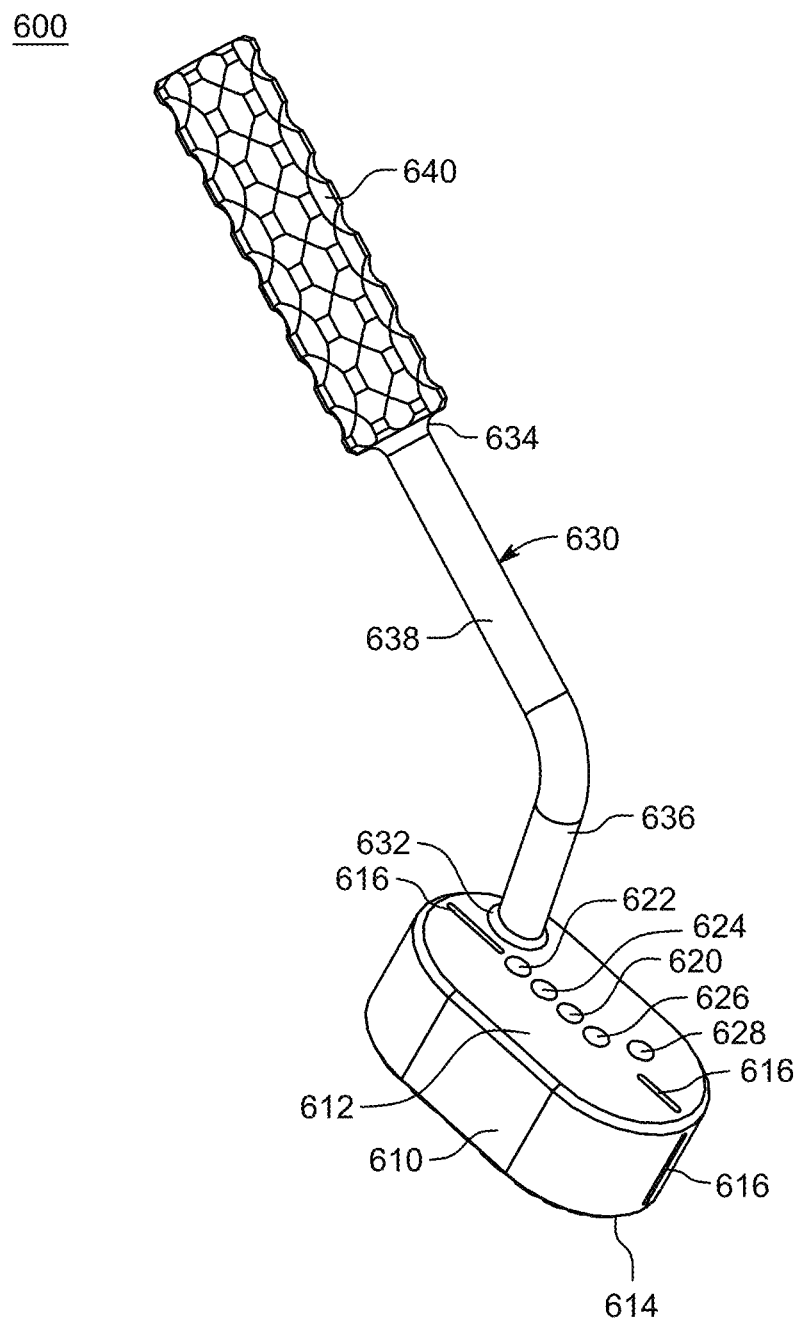
FIG. 59 is a perspective view of an embodiment of an alignment device, in accordance with an aspect of the present invention.
Figure 60:
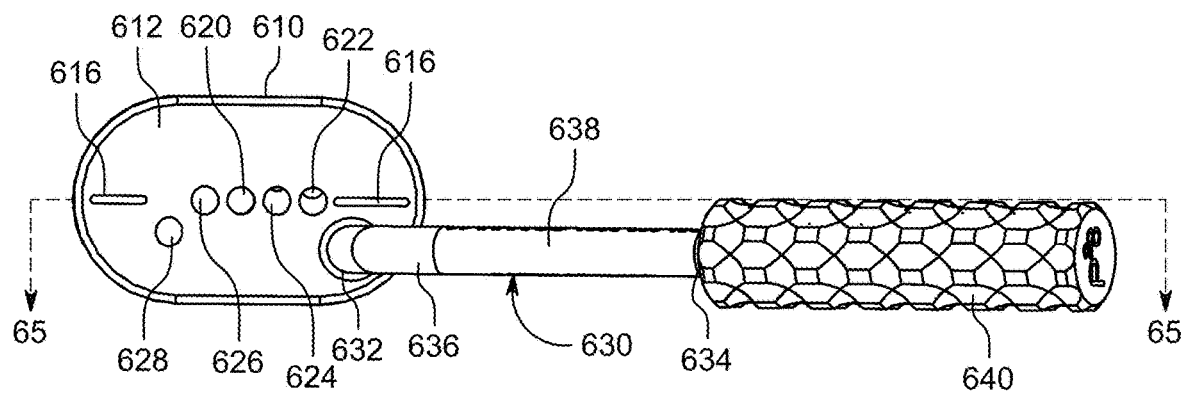
FIG. 60 is a top view of the alignment device of FIG. 59, in accordance with an aspect of the present invention.

Further as shown in FIGS. 59 and 61, the base 610 may include a plurality of openings 620, 622, 624, 626, 628. The openings 622, 624, 626, 628 may be positioned at a specific rotation angle as they extend through the base 610 from the top surface 612 to the bottom surface 614. For example, the base 610 may include a zero opening 620 positioned near a center of the base 610. The zero opening 620 may have, for example, an insertion angle of 0° for inserting a guide wire, k-wire or the like into a patient at a 0° angle. The zero opening 620 may be used for positioning and aligning the alignment device 600. The base 610 may also include a first angled opening 622 positioned near the shaft 630. The first angled opening 622 may have, for example, a first rotation angle ranging from 10° to 19° and a guide wire, k-wire or the like may be inserted through the opening 622. In an embodiment, the first angled opening 622 may be, angled, for example, 7.5° and may have a rotation angle of, for example, 15°. A second angled opening 624 may be positioned between the zero opening 620 and the first angled opening 622. The second angled opening 624 may have, for example, a second rotation angle ranging from 20° to 29° and a guide wire, k-wire or the like may be inserted through the opening 624. In an embodiment, the second angled opening 624 may be, angled, for example, 11° and may have a rotation angle of, for example, 22°. A third angled opening 626 may be positioned proximal the zero opening 620. The third angled opening 626 may have, for example, a third rotation angle ranging from 30° to 39° and a guide wire, k-wire or the like may be inserted through the opening 626. In an embodiment, the third angled opening 626 may be, angled, for example, 15° and may have a rotation angle of, for example, 30°. The base 610 may also include a fourth angled opening 628 positioned proximal to the third angled opening 626. The fourth angled opening 628 may have, for example, a fourth rotation angle ranging from 40° to 50° and a guide wire, k-wire or the like may be inserted through the opening 628. In an embodiment, the fourth angled opening 628 may be, angled, for example, 22.5° and may have a rotation angle of, for example, 45°. As shown in the depicted embodiment of FIGS. 59-61 and 65, the openings 620, 622, 624, 626 may be positioned linearly along the top surface 612 of the base 610. The fourth angled opening 628 may be, for example, positioned offset from the openings 620, 622, 624, 626. The openings 620, 622, 624, 626, 628 may be positioned in alternative 2D layouts that ensure that the plantar portion of the osteotomy terminates a certain distance from the joint line, for example, approximately 10 mm. In another embodiment, the first angled opening 622 may be angled, for example, 7.5° for a rotation angle of 15°, the second angled opening 624 may be angled, for example, 12.5° for a rotation angle of 25°, the third angled opening 626 may be angled, for example, 17.5° for a rotation angle of 35°, and the fourth angled opening 628 may be angled, for example, 22.5° for a rotation angle of 45°.

With continued reference to FIGS. 59-65, the shaft 630 includes a first end 632 coupled to the base 610 and a second end 634 coupled to the handle 640. The shaft 630 may include a first segment 636 near the first end 632 and a second segment 638 near the second end 634. The first segment 636 may be angled relative to the second segment 638. The shaft 630 may be positioned offset to one side of the top surface 612.

Referring now to FIGS. 66-71, the cut guide 700 is shown. The cut guide 700 includes a first or distal end 702 opposite a second or proximal end 704, a first side 706 opposite a second side portion 708, and a top surface 710 opposite a bottom surface 712. The top surface 710 may be, for example, parallel to the bottom surface 712. The cut guide 700 may also include a curved portion 714 extending from the proximal end 704 to the second side portion 708. The distal end 702 of the cut guide 700 may include a recessed region 716 extending into the cut guide 700 and forming a leg portion 718. The leg portion 718 may include a foot portion 720 extending from the first side 706 toward the second side portion 708. The foot portion 720 may include an opening 722 for receiving a guide wire, k-wire or the like, as described in greater detail below with reference to FIGS. 92-94. The opening 722 may extend through the cut guide 700 from the top surface 710 to the bottom surface 712.

With continued reference to FIGS. 66-69, the cut guide 700 may also include a window 724 positioned near the proximal end 704. The window 724 may extend through the cut guide 700 from a top surface 710 to a bottom surface 712. The window 724 may be positioned and sized, for example, to provide visualization of the bone. In addition, the cut guide 700 may include at least one cutting slot 726, 728 extending between the first side 706 and the second side 708. The cutting slots 726, 728 may also extend through the cut guide 700 from a top surface 710 to a bottom surface 712. In the embodiment depicted in FIGS. 66-69, the cut guide 700 may include, for example, two cutting slots 726, 728. The first cutting slot 726 may be positioned, for example, adjacent to the recessed region 716. The second cutting slot 728 may be, for example, positioned between the first cutting slot 726 and the window 724. The first and second cutting slots 726, 728 may be, for example, positioned parallel to each other.

Figure 67:
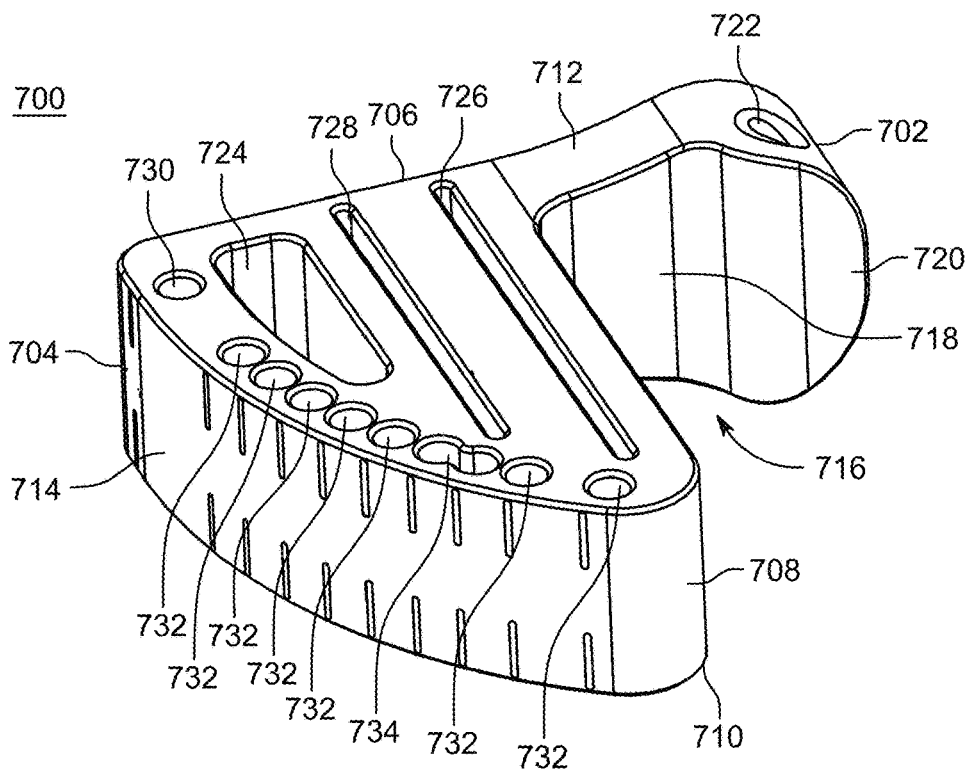
FIG. 67 is a second side perspective view of the cut guide of FIG. 66, in accordance with an aspect of the present invention.
Figure 68:
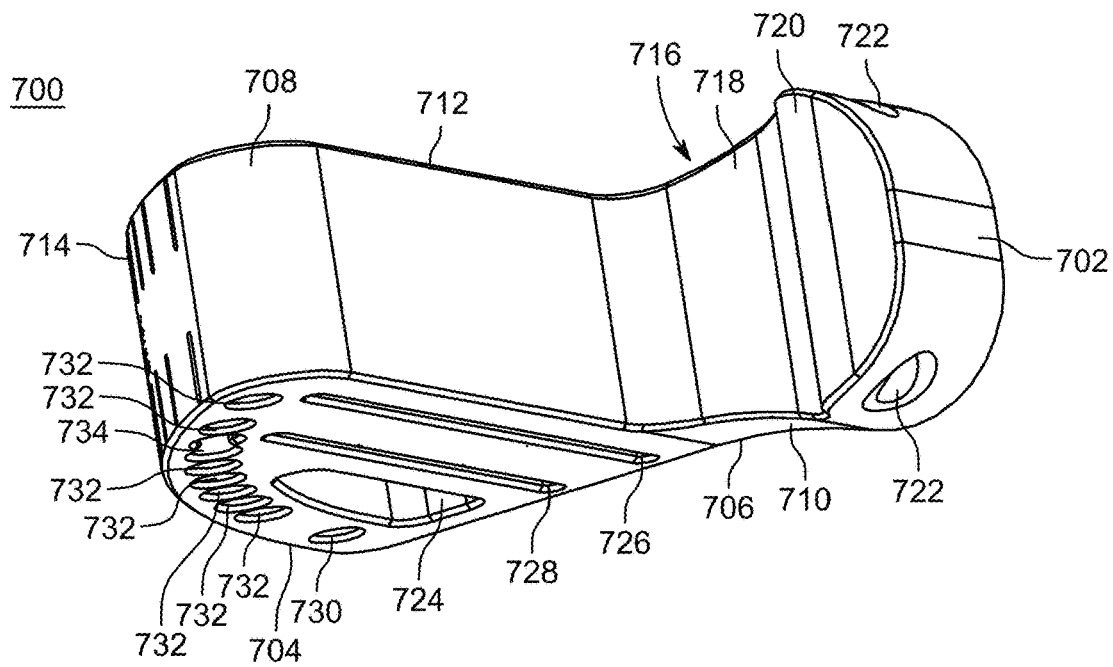
FIG. 68 is a distal end perspective view of the cut guide of FIG. 66, in accordance with an aspect of the present invention.
Figure 69:
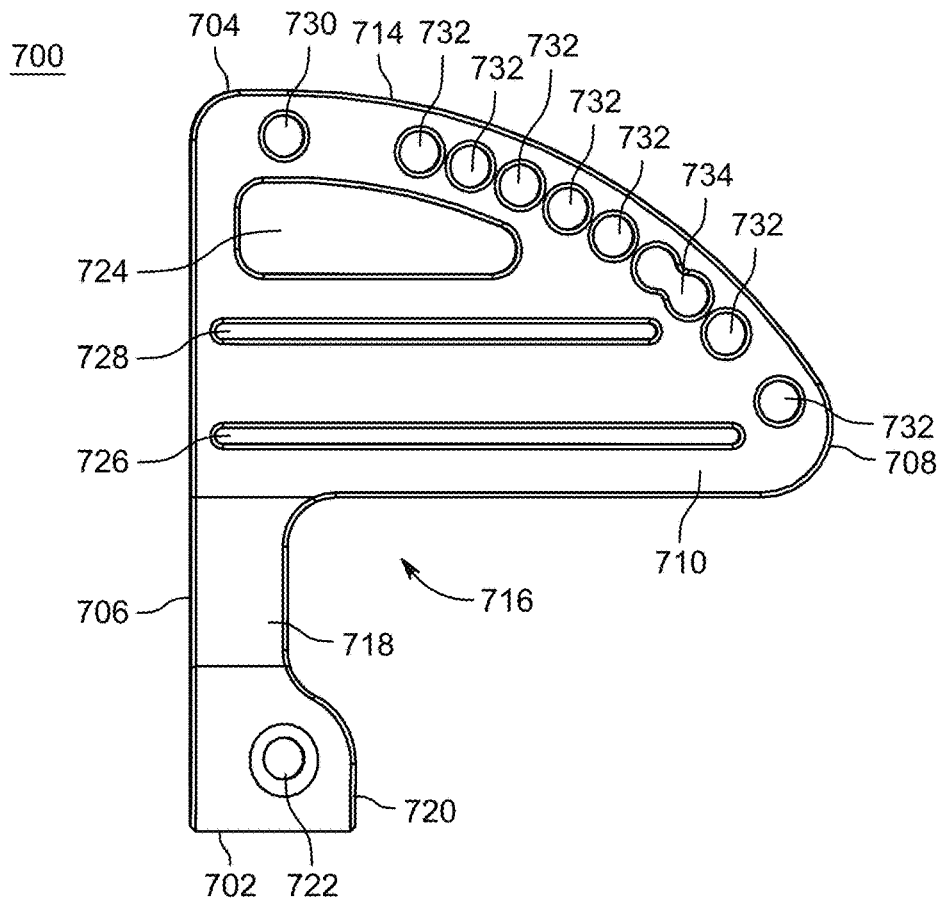
FIG. 69 is a top view of the cut guide of FIG. 66, in accordance with an aspect of the present invention.
Figure 70:
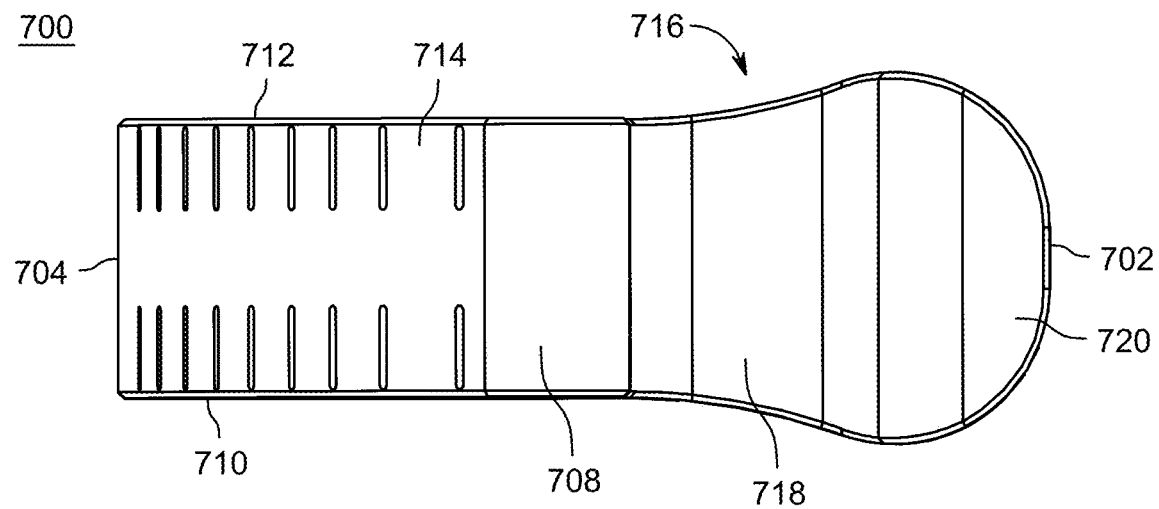
FIG. 70 is a side view of the cut guide of FIG. 66, in accordance with an aspect of the present invention.
Figure 71:
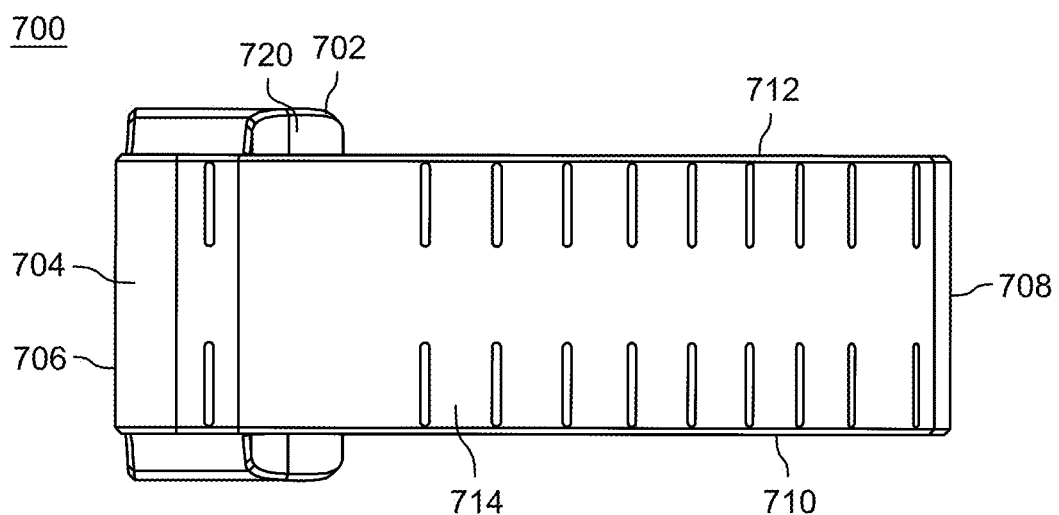
FIG. 71 is an end view of the cut guide of FIG. 66, in accordance with an aspect of the present invention.

The cut guide 700 may further include a first or zero opening 730 and a plurality of second openings 732 positioned along the curved portion 714 of the cut guide 700, as shown in FIGS. 66-69. The cut guide 700 may also include, for example, at least one double opening 734 positioned along the curved portion 714 of the cut guide 700, as shown in FIGS. 66-69. Depending on the size of the cut guide 700, the cut guide 700 may include at least one double opening 734 if the openings 732 of the desired osteotomy cut angles overlap along the curved portion 714 of the cut guide 700. The openings 730, 732, 734 may extend through the cut guide 700 from the top surface 710 to the bottom surface 712. The openings 730, 732, 734 may be, for example, positioned along the curvature of the curved portion 714. The openings 730, 732 may be sized and shaped or configured to receive a k-wire, guide wire, or the like, described in greater detail below with reference to FIGS. 92-94. The double opening 734 may be formed by a portion of two openings 732 overlapping. The double opening 734 may be sized and shaped or configured to receive a single k-wire, guide wire, or the like in two different positions within the double opening 734. Referring now to FIG. 67, the first opening 730 may be, for example, a 0° opening and the second openings 732 and double opening 734 may have angles relative to a line connecting the first opening 730 and the distal opening 722. The angles of the second openings 732 and the double opening 734 range from, for example, approximately 8° to 60°, and more preferably approximately 13° to 55°. In an embodiment, the second openings 732 may include angles of, for example, 13°, 18°, 23°, 28°, 33°, 38°, 42°, 47° and 55° with the 38° and 42° angles forming a double opening 734. Alternative angles between approximately 13° to 55° are also contemplated. Further, the double opening 734 may include two different angles within the above range of angles.

Figure 75:
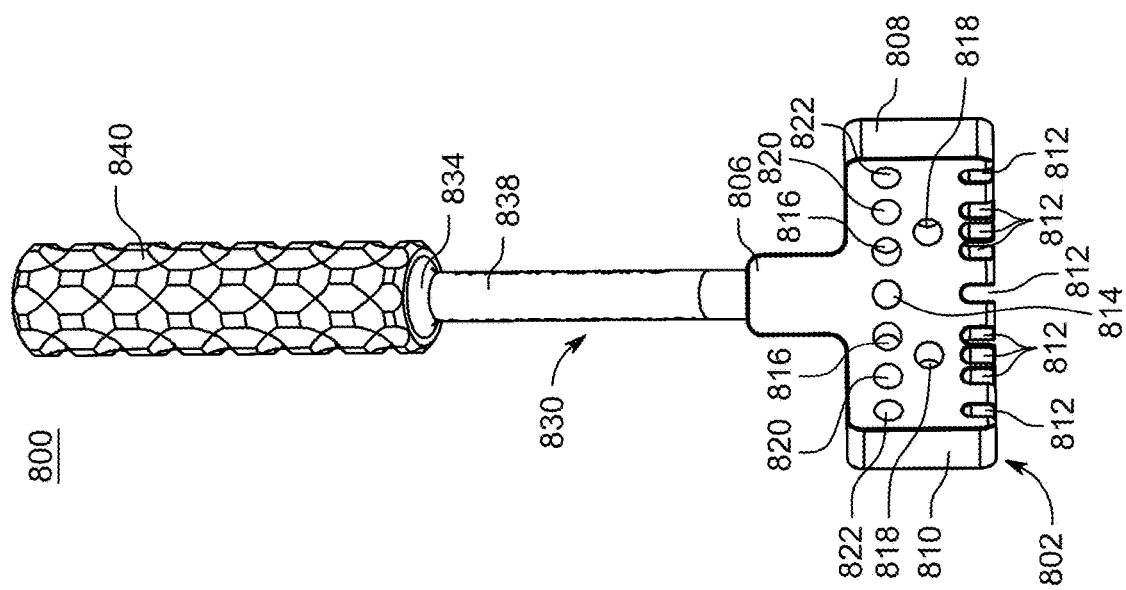
FIG. 75 is a bottom view of the position rotation device of FIG. 72, in accordance with an aspect of the present invention.
Figure 76:
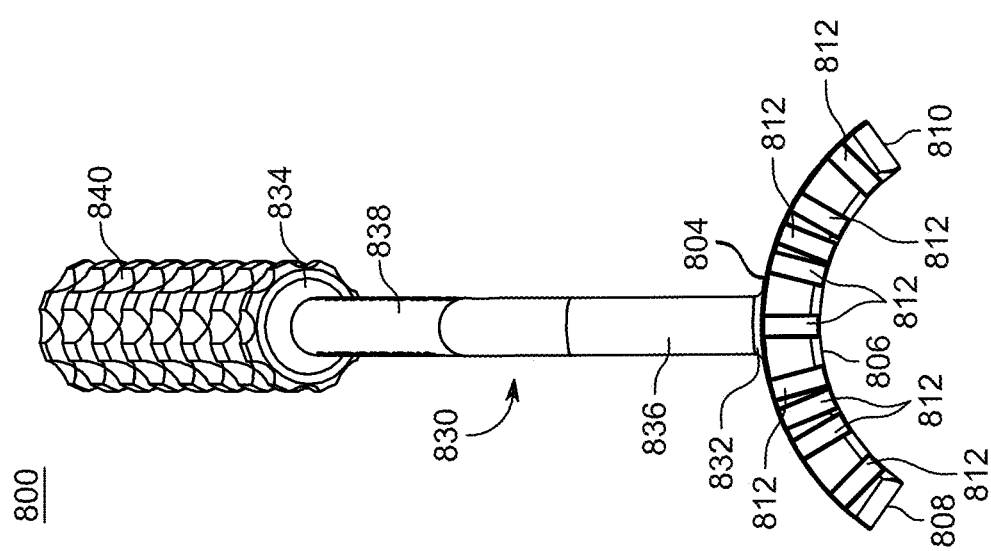
FIG. 76 is a front view of the position rotation device of FIG. 72, in accordance with an aspect of the present invention.

The position rotation device 800 is shown in FIGS. 72-77. The rotation device includes a base 802 with a top surface 804 opposite a bottom surface 806, as shown in FIG. 76. The base 802 also includes a first end 808 opposite a second end 810. The base 802 may be, for example, curved to form a semi-circle or arc as the base 802 extends from the first end 808 to the second end 810, as shown in FIG. 76. The base 802 may also optionally include a plurality of alignment grooves 812. The alignment grooves 812 may be inset into a front side of the base 802 and may extend from the top surface 804 through the base 802 to the bottom surface 806.

With continued reference to FIGS. 72-75, the base 802 further includes a first or zero opening 814 positioned, for example, centered between the first end 808 and the second end 810 of the base 802. The zero opening 814 may be positioned adjacent to the first end 832 of the shaft 830. The zero opening 814 may also be positioned, for example, near a back side of the base 802. The zero opening 814 may have, for example, an insertion angle for a guide wire, k-wire or the like of 0° as the opening 814 extends from the top surface 804 to the bottom surface 806. The zero opening 814 may be used for positioning and aligning the position rotation device 800 on a patient. The zero opening 814 may be, for example, sized and shaped or configured to receive a guide wire, k-wire or the like, as described in greater detail below with reference to FIGS. 96 and 97.

Figure 73:
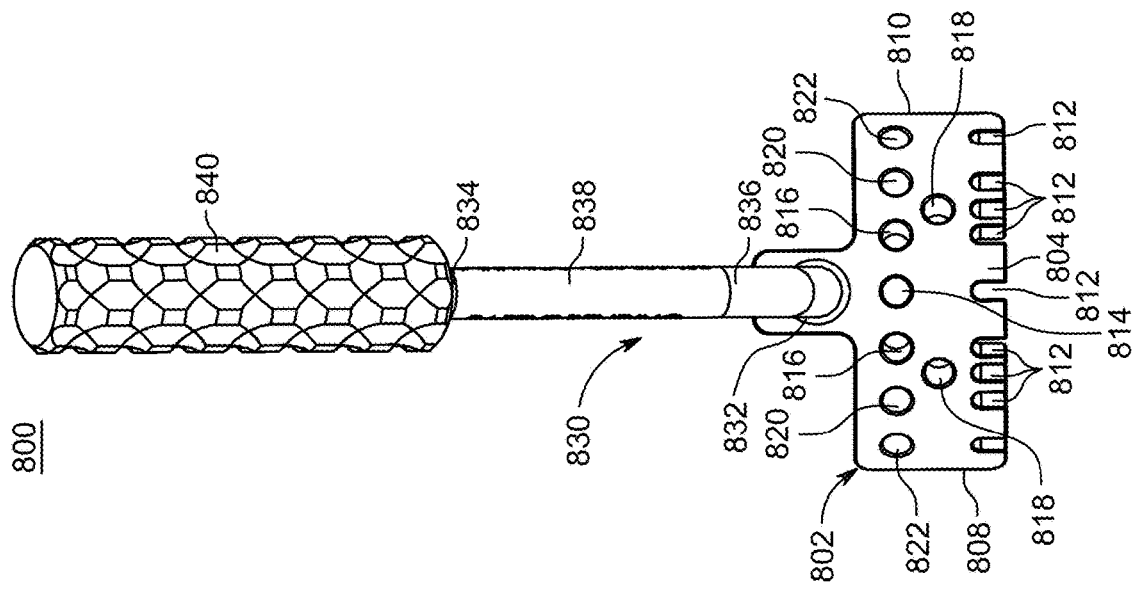
FIG. 73 is a top view of the position rotation device of FIG. 72, in accordance with an aspect of the present invention.
Figure 72:
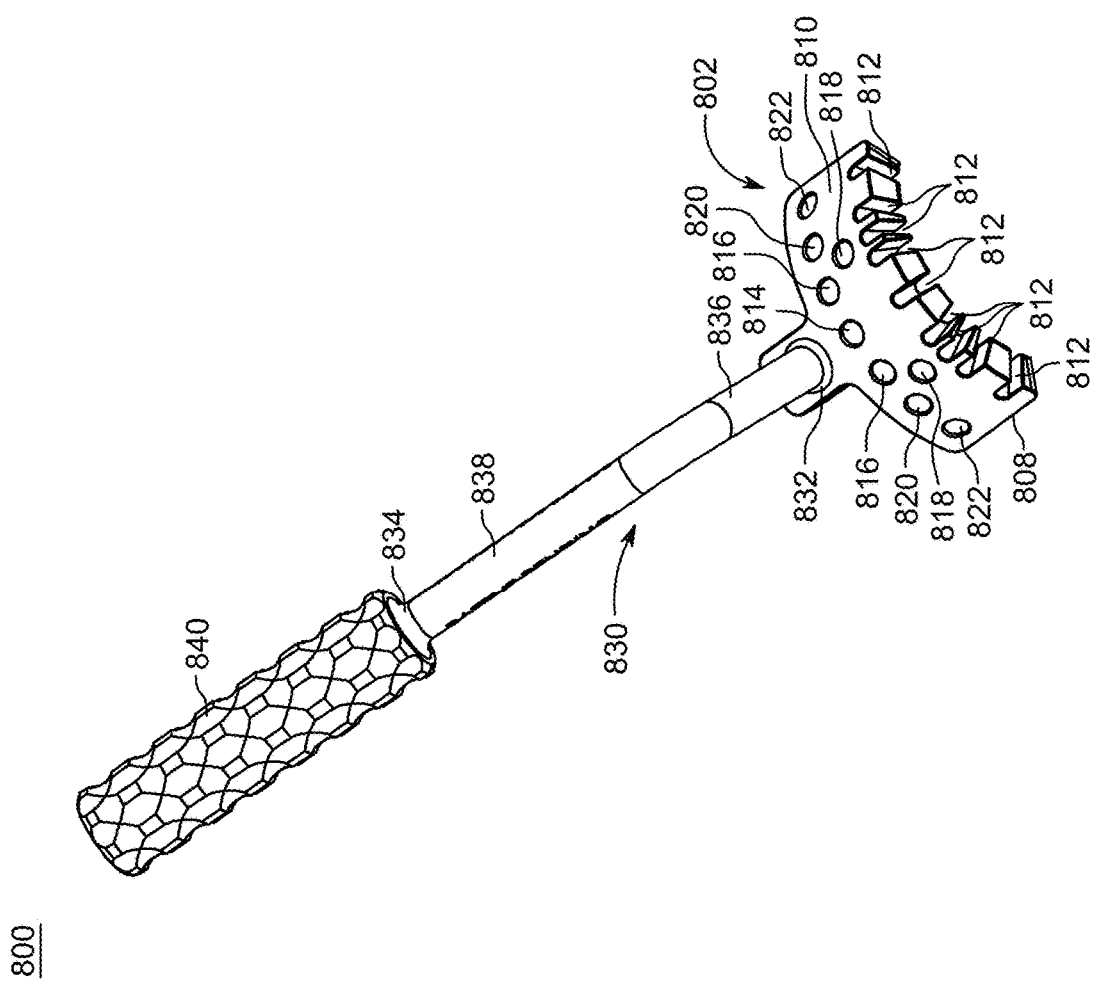
FIG. 72 is a top perspective view of another embodiment of a position rotation device, in accordance with an aspect of the present invention.

As shown in FIGS. 72, 73 and 75, the base 802 may also include two first angled openings 816. One first angled opening 816 may be positioned between the zero opening 814 and the first end 808 and be adjacent to the zero opening 814. The second first angled opening 816 may be positioned between the zero opening 814 and the second end 810 and also be adjacent to the zero opening 814. The first angled openings 816 may have, for example, first rotation angles relative to the zero opening 814. The first rotation angles may, for example, range from 10° to 19° and may receive a guide wire, k-wire or the like.

The base 802 may further include two second angled openings 818, as shown in FIGS. 72, 73 and 75. One second angled opening 818 may be positioned between the zero opening 814 and the first end 808 and the other second angled opening 818 may be positioned between the zero opening 814 and the second end 810. As shown in the depicted embodiment, the second angled openings 818 may be positioned between the first angled openings 816 and the alignment grooves 812. The second angled openings 818 may have, for example, second rotation angles relative to the zero opening 814. The second rotation angles may, for example, range from 20° to 29° and may receive a guide wire, k-wire or the like.

In addition, as shown in FIGS. 72, 73 and 75, the base 802 may include two third angled openings 820. One third angled opening 820 may be positioned between the zero opening 814 and the first end 808 and the other third angled opening 820 may be positioned between the zero opening 814 and the second end 810. The third angled openings 820 may have, for example, third rotation angles relative to the zero opening 814. The third rotation angles may, for example, range from 30° to 39° and may receive a guide wire, k-wire or the like. The third angled openings 820 may be positioned adjacent to the first angled openings 816 and offset from the second angled openings 818.

Further, the base 802 may include two fourth angled openings 822, as shown in FIGS. 72, 73 and 75. One fourth angled opening 822 may be positioned between the zero opening 814 and a first end 808 and the other fourth angled opening 822 may be positioned between the zero opening 814 and a second end 810. The fourth angled openings 822 may have, for example, fourth rotation angles relative to the zero opening 814. The fourth rotation angles may, for example, range from 40° to 50° and may receive a guide wire, k-wire or the like. The fourth angled openings 822 may be positioned adjacent to the third angled openings 820 and offset from the second angled openings 818.

As shown in FIGS. 72, 73 and 75, the openings 814, 816, 818, 820, 822 may each be, for example, aligned with an alignment groove 812 of the plurality of alignment grooves 812. The openings 814, 816, 820, 822 may be positioned linearly along the base 802 as it curves from the first end 808 to the second end 810. It is also contemplated that the openings 814, 816, 818, 820, 822 may be positioned, for example, linearly along the base 802 as it curves from the first end 808 to the second end 810. Alternatively, each of the openings 816, 818, 820, 822 may be, for example, offset from the zero opening 814. The openings 816, 818, 820, 822 may be positioned, for example, between the zero opening 814 and the alignment grooves 812.

Figure 74:
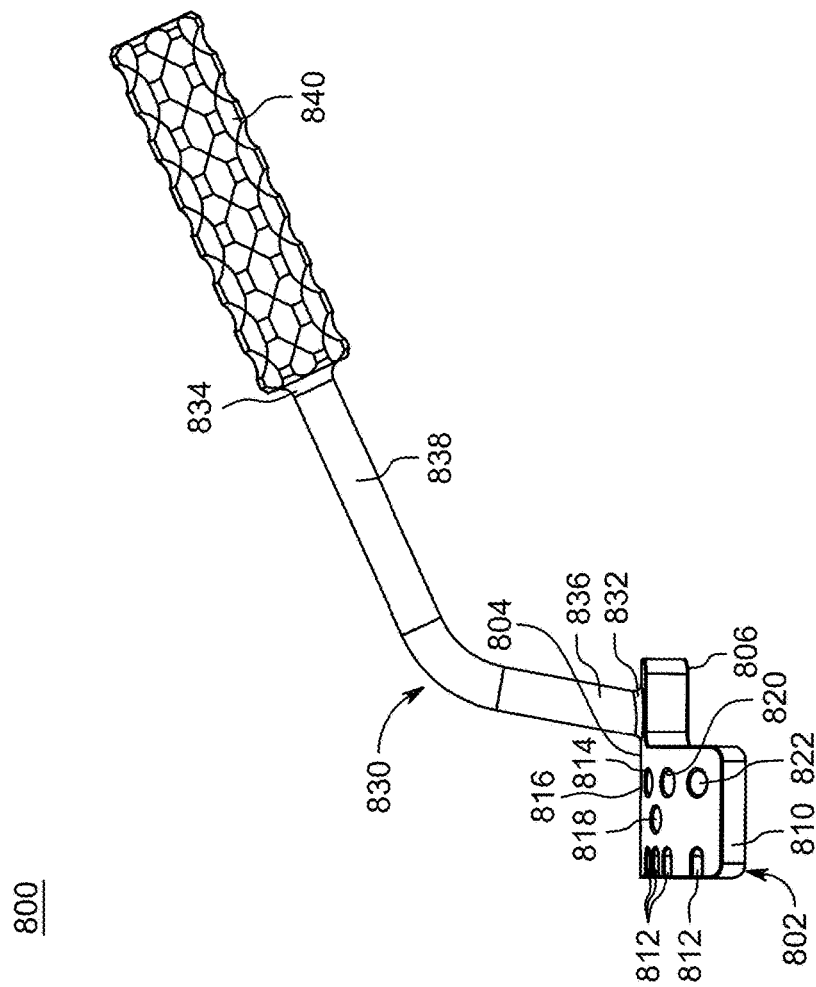
FIG. 74 is a side view of the position rotation device of FIG. 72, in accordance with an aspect of the present invention.
Figure 77:
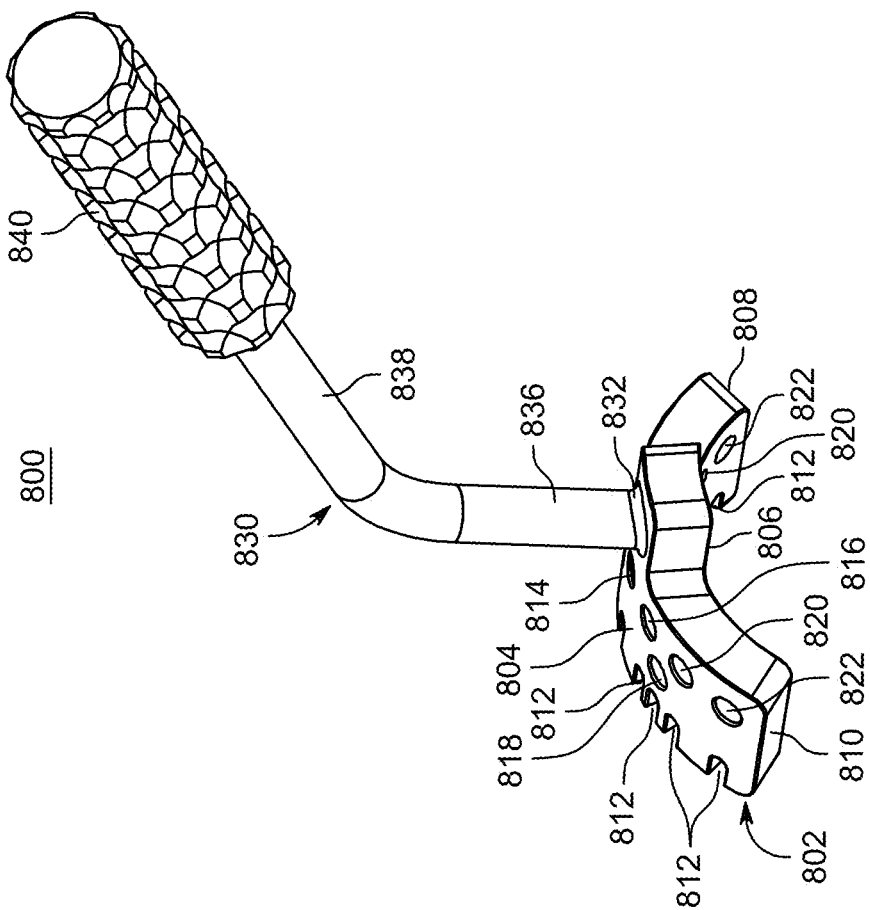
FIG. 77 is a rear perspective view of the position rotation device of FIG. 72, in accordance with an aspect of the present invention.

The shaft 830 may include a first end 832 and a second end 834, as shown in FIGS. 72-77. The first end 832 may be coupled to the top surface 804 of the base 802 near a center point of the base 802. The second end 834 may be coupled to a handle 840. The shaft 830 may include a first segment 836 near the first end 832 and a second segment 838 near the second end 834. As shown in FIGS. 74 and 77, the first segment 836 may be angled relative to the second segment 838.

Figure 78:
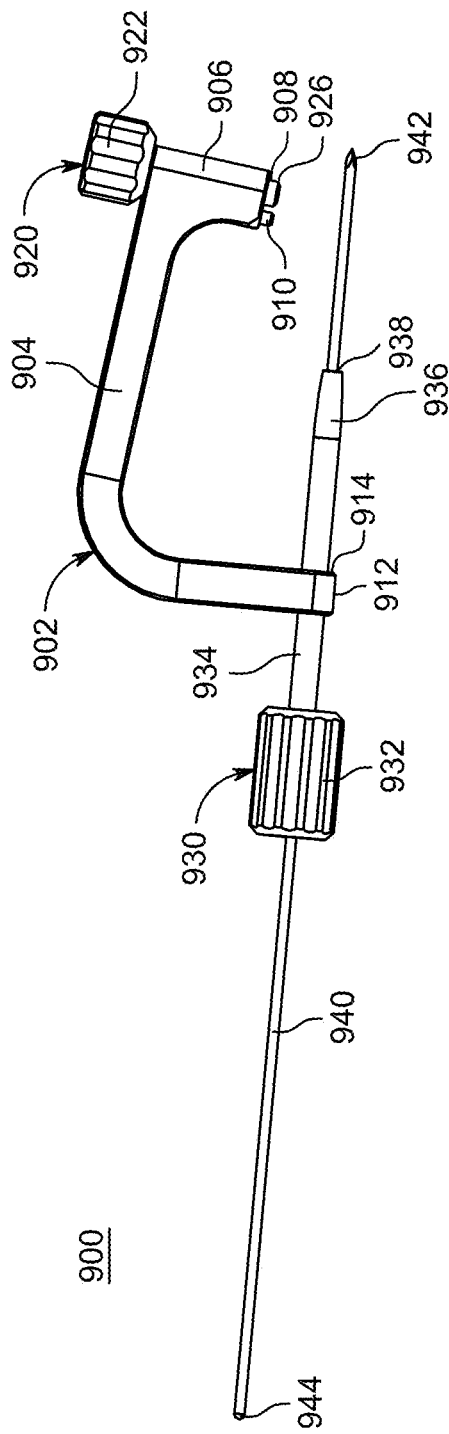
FIG. 78 is a side view of an alignment guide, in accordance with an aspect of the present invention.
Figure 79:
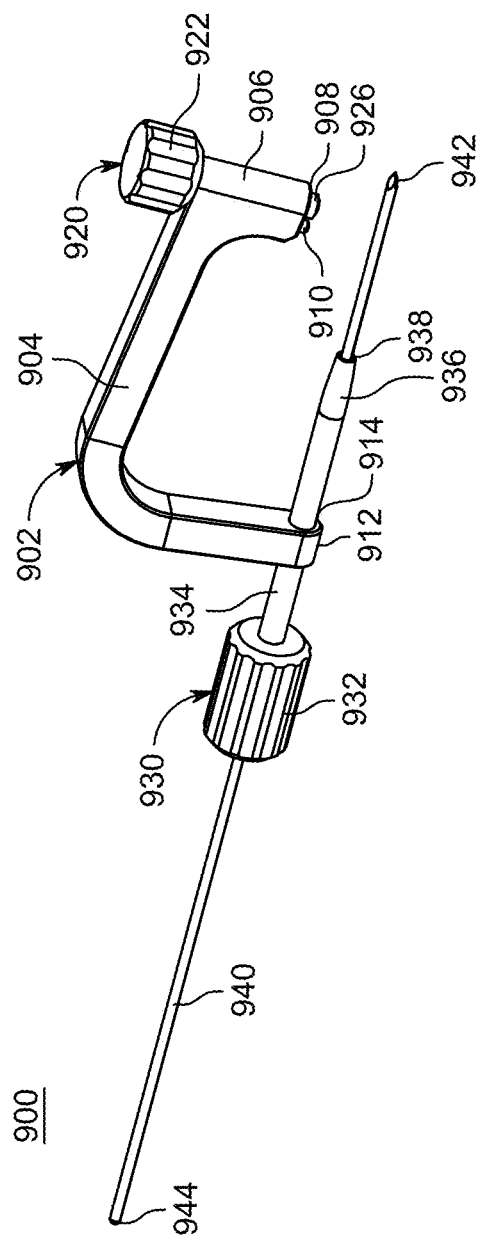
FIG. 79 is a side perspective view of the alignment guide of FIG. 78, in accordance with an aspect of the present invention.
Figure 80:
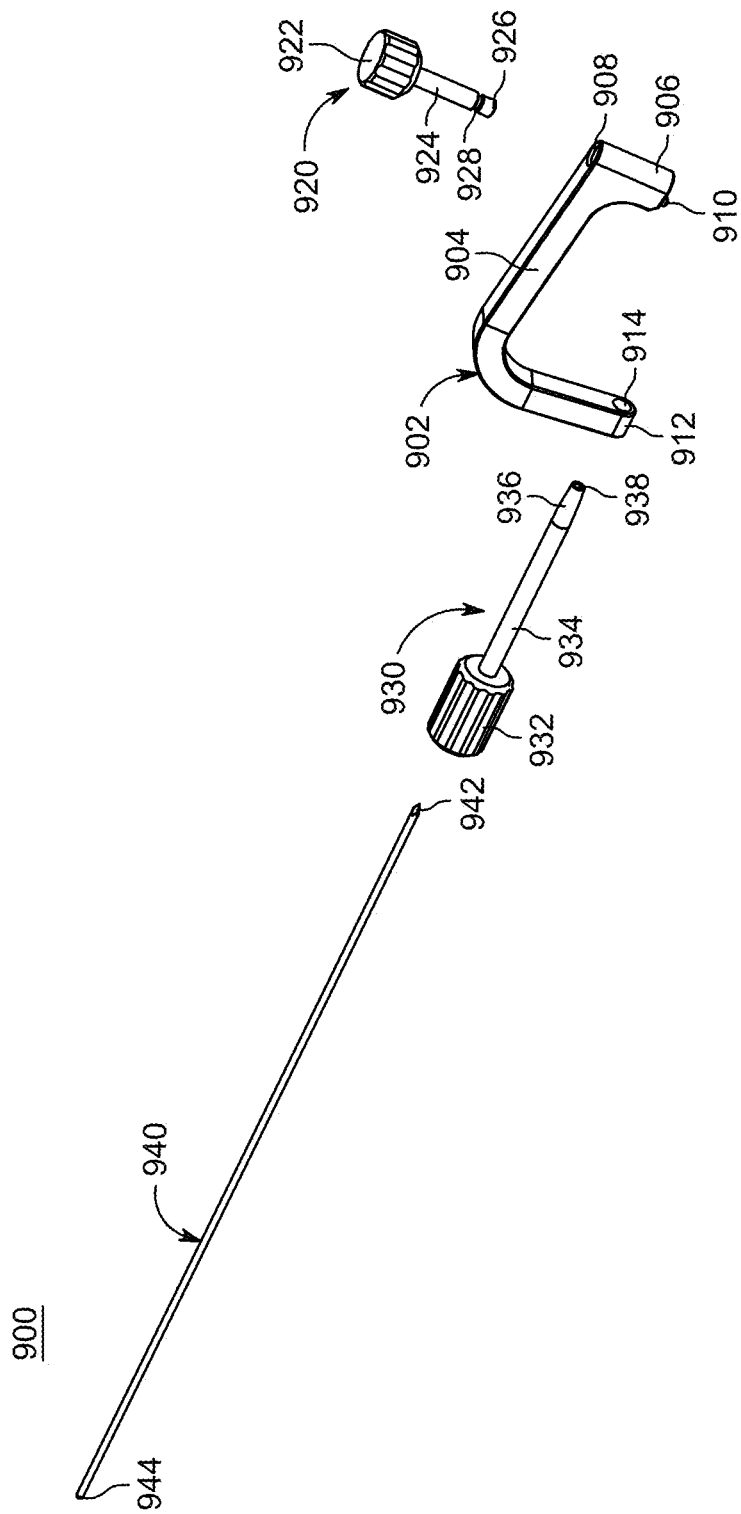
FIG. 80 is an exploded, side perspective view of the alignment guide of FIG. 78, in accordance with an aspect of the present invention.
Figure 81:
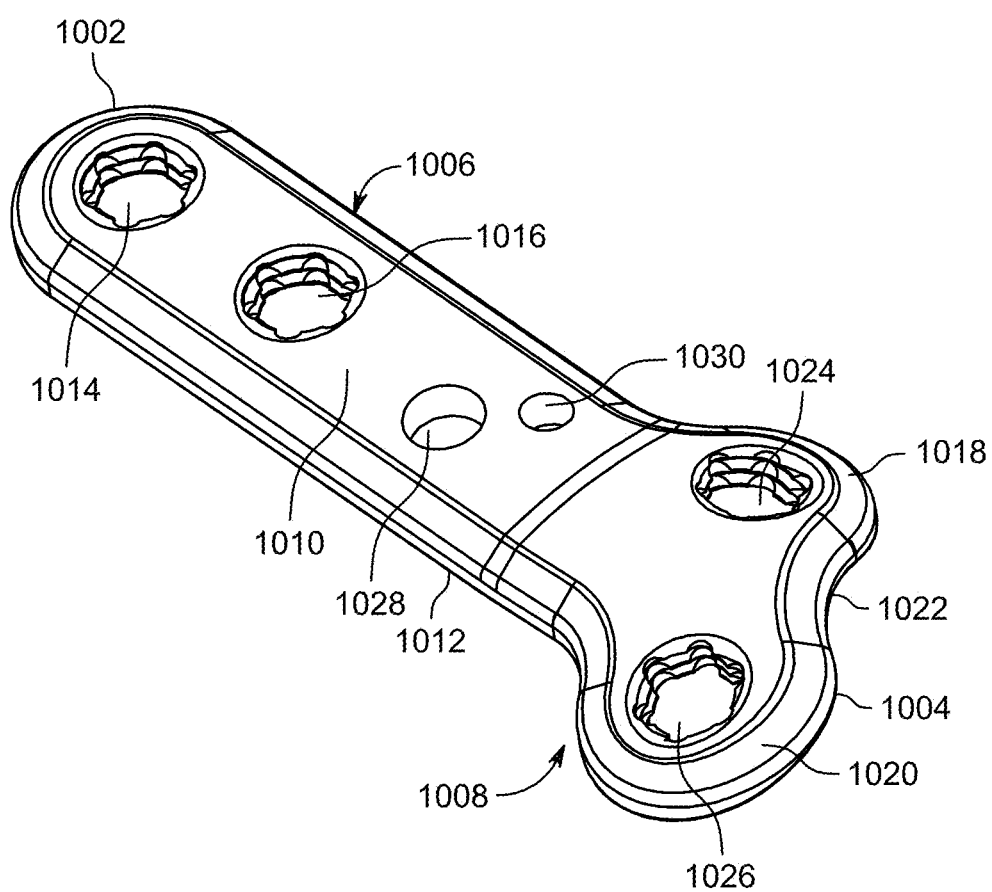
FIG. 81 is a top perspective view of another embodiment of a bone plate, in accordance with an aspect of the present invention.
Figure 82:
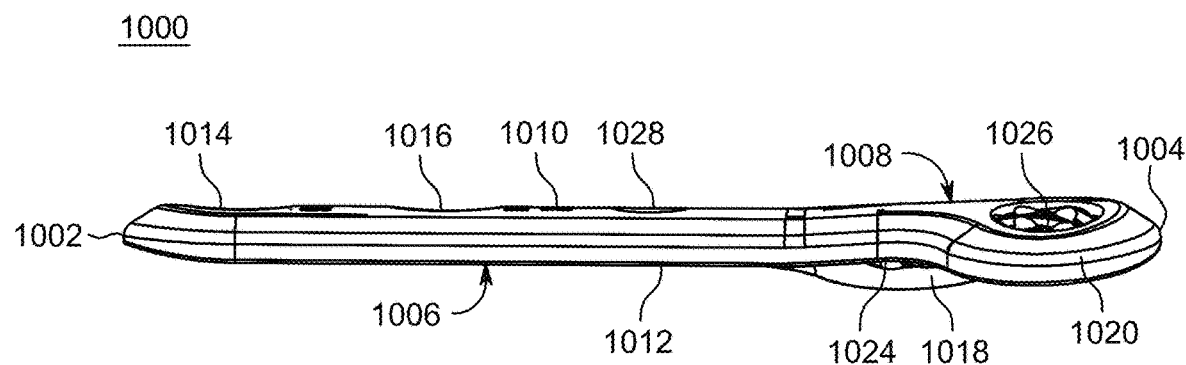
FIG. 82 is a first side view of the bone plate of FIG. 81, in accordance with an aspect of the present invention.
Figure 83:
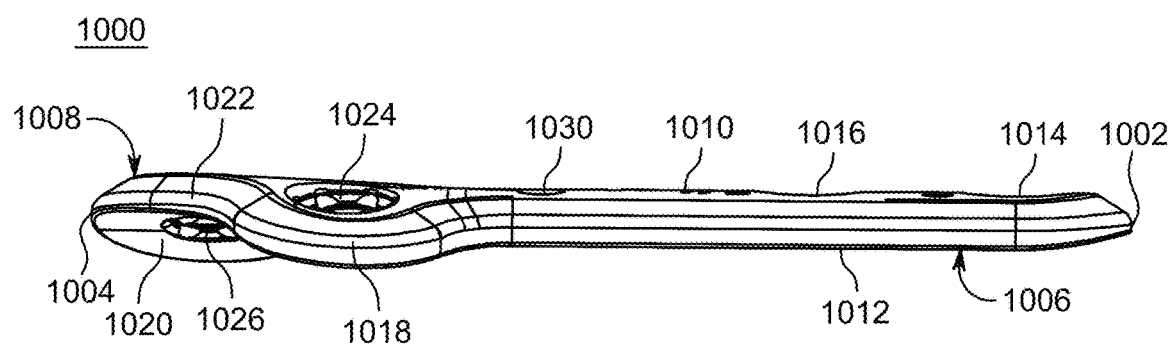
FIG. 83 is a second side view of the bone plate of FIG. 81, in accordance with an aspect of the present invention.
Figure 84:
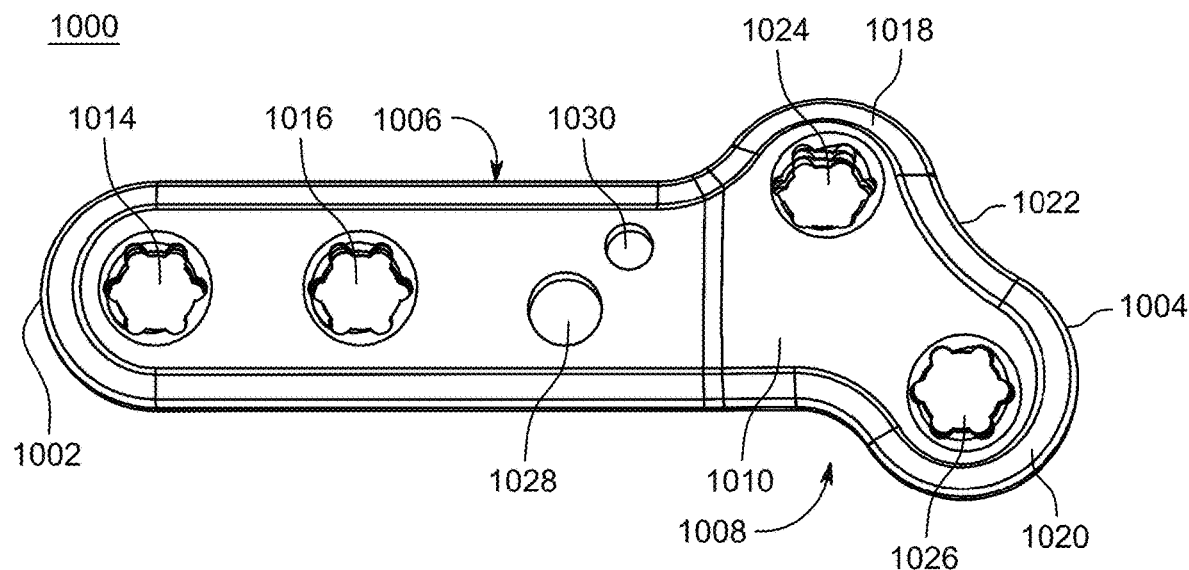
FIG. 84 is a top view of the bone plate of FIG. 81, in accordance with an aspect of the present invention.
Figure 85:
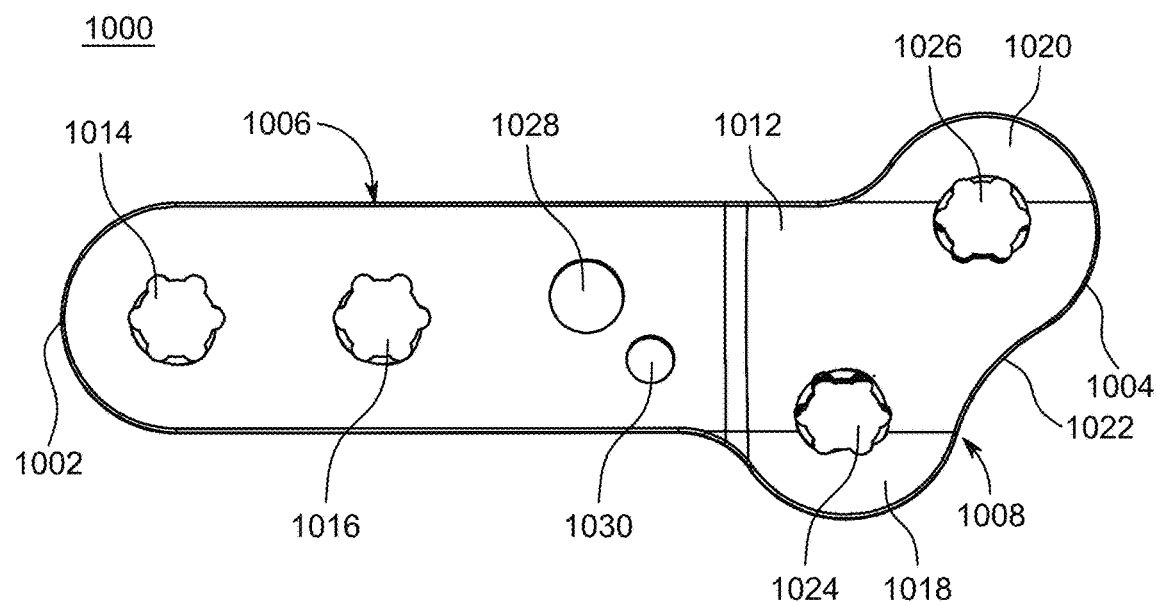
FIG. 85 is a bottom view of the bone plate of FIG. 81, in accordance with an aspect of the present invention.

The alignment guide 900 is shown in FIGS. 78-80. The alignment guide 900 includes a body or alignment guide 902, a fixation member 920, a guide pin protector 930, a guide wire or pin 940, and a fastener 1160 (See FIGS. 105 and 106). The body 902 may include an arm 904 with an attachment portion 906 at a first end and an alignment portion 912 at a second end. The arm 904 may be, for example, angled or curved over the alignment portion 912. The body 902 may also include a through hole 908 in the attachment portion 906 of the body 902, as seen in FIG. 80. Further, the body 902 may include an alignment protrusion 910 extending away from the attachment portion 906, as shown in FIGS. 78-80, for engaging an opening 1030 in a bone plate 1000 of FIGS. 81-87. The alignment protrusion 910 may be used to position the bone plate alignment guide apparatus 900 on the bone plate 1000. The through hole 908 may be positioned, for example, adjacent to the alignment protrusion 910, as shown in FIGS. 78-80. The alignment portion 912 may include, for example, a through hole 914, as shown in FIGS. 79-80. The hole 914 may be straight or angled to a desired insertion position relative to the arm 904 of the body 902.

The fixation member 920 may include a knob portion 922 and a shaft portion 924 with an engagement portion 926 for engaging the bone plate 1000 of FIGS. 81-87. The engagement portion 926 may be, for example, threaded to engage corresponding threads in an opening 1028 in the bone plate 1000, deformable to be removeably press fit into the opening 1028 in the bone plate 1000, or similar configurations that achieve a coupling of the guide apparatus 900 to the second alignment guide opening 1028 of the bone plate 1000. The shaft portion 924 of the fixation member 920 may also include a groove or recessed region 928 positioned adjacent to the engagement portion 926.

The guide pin protector or tissue protector 930, as shown in FIGS. 78-80, may include a handle portion 932 at a first end and a shaft 934 extending away from the handle portion 932 to a tip 938 at a second end. The shaft 934 may taper at the second end to form the tip 936. The guide pin protector 930 may also include a through hole 938 extending from the first end to the second end to enable a guide wire 940 to pass through the tissue protector 930 and into a patient. The guide wire 940 may include a first end 942 and a second end 944. The first end 942 may be, for example, sharp or pointed for insertion into the patient.

Figure 86:
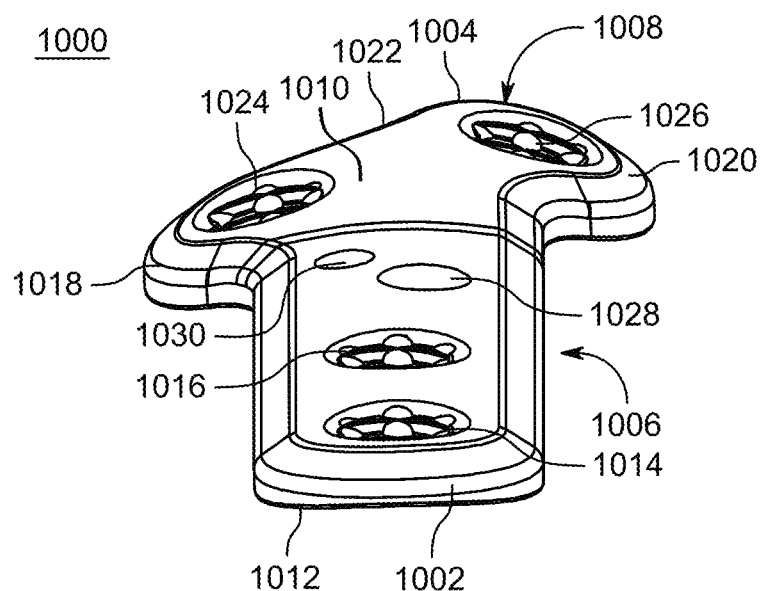
FIG. 86 is a first end perspective view of the bone plate of FIG. 81, in accordance with an aspect of the present invention.
Figure 87:
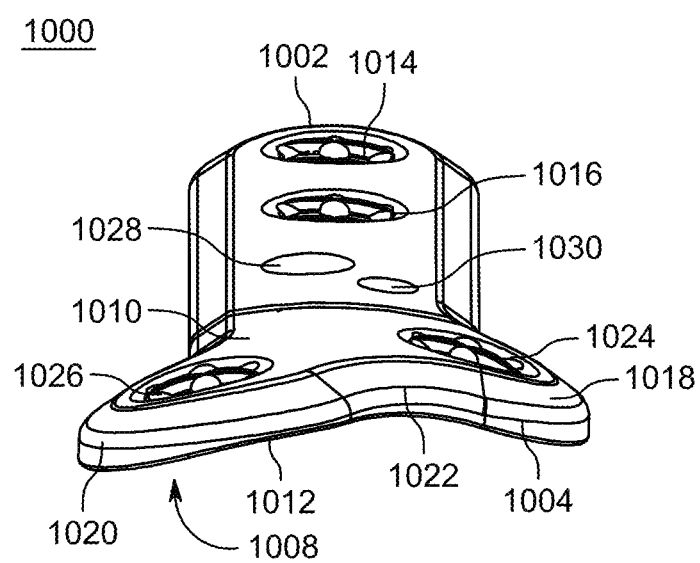
FIG. 87 is a second end perspective view of the bone plate of FIG. 81, in accordance with an aspect of the present invention.

The plate or implant 1000 is shown in FIGS. 81-87. The plate 1000 may include a first end 1002 and a second end 1004 opposite the first end 1002. The plate 1000 may also include a first portion 1006 extending from the first end 1002 and a second portion 1008 extending from the first portion 1006 to the second end 1004. The plate 1000 may also include a top surface 1010 opposite a bottom surface 1012. As shown in FIGS. 86 and 87, the top surface 1010 may be, for example, curved as the plate 1000 extends from a first side to a second side, perpendicular to the longitudinal axis of the plate 1000. In addition, the bottom surface 1012 may be, for example, curved to match the shape or curvature of the bone receiving the plate 1000 as the plate 1000 extends from the first side to the second side, perpendicular to the longitudinal axis of the plate 1000.

With continued reference to FIGS. 81-87, the first portion 1006 may include at least one opening 1014, 1016 for receiving a fastener or bone screw (not shown). The at least one opening 1014, 1016 may include, for example, a first opening 1014 positioned near the first end 1002 and a second opening 1016 positioned adjacent to the first opening 1014. The openings 1014, 1016 may include a threaded portion on the interior surface of the openings 1014, 1016. The threaded portion may have, for example, at least one scallop or cutout forming a break in the threads of the threaded portion. The threaded portion and at least one cutout are shaped to lock the fastener or bone screw in the openings 1014, 1016. The at least one opening 1014, 1016 may be tapered from the top surface 1010 to the bottom surface 1012 of the plate 1000. Although only two openings 1014, 1016 are shown in the depicted embodiment, it is also contemplated that the first portion 1006 may include, for example, more than two openings 1014, 1016 to provide for additional fastening locations to secure the first portion 1006 of the plate 1000 to a patient. The first portion 1006 may also include a first alignment guide opening 1028 for receiving the alignment protrusion 910 of the alignment guide 900. In addition, the first portion 1006 may include a second alignment guide opening 1030 for receiving the engagement portion 926 of the fixation member 920 to secure the alignment guide 900 to the plate 1000.

With continued reference to FIGS. 81-87, the second portion 1008 may include a first lobe 1018 extending out from a first side of the plate 1000 and a second lobe 1020 extending out from a second side of the plate 1000. The second lobe 1020 may extend away from a longitudinal axis of the plate 1000 farther than the first lobe 1018 extends away forming a curved region 1022 between the first and second lobes 1018, 1020. The second portion 1008 may include at least one opening 1024, 1026. For example, a third opening 1024 may be positioned in the first lobe 1018 and a fourth opening 1026 may be positioned in a second lobe 1020. The openings 1024, 1026 may also include a threaded portion on the interior surface of the openings 1024, 1026. The threaded portion may have, for example, at least one scallop or cutout forming a break in the threads of the threaded portion. The threaded portion and at least one cutout are shaped to lock the fastener or bone screw in the openings 1024, 1026. The at least one opening 1024, 1026 may be tapered from the top surface 1010 to the bottom surface 1012 of the plate 1000. Although only two openings 1024, 1026 are shown in the depicted embodiment, it is also contemplated that the second portion 1008 may include, for example, more than two openings 1024, 1026 to provide for additional fastening locations to secure the second portion 1008 of the plate 1000 to a patient.

Although only one plate 1000 is shown, it is contemplated that the plate 1000 may be available in varying lengths to correspond to the varying angles of the osteotomy and the corresponding vertical inclination angles. As would be understood by one of ordinary skill in the art, as the vertical inclination angle increases the cut will be longer, thus needing a longer plate 1000 for proper placement along the bones. As the size of the plate 1000 increases, the positions of the openings 1014, 1016, 1024, 1026 and alignment openings 1028, 1030 may vary to correctly position the alignment device 900 on the plate 1000 and the openings 1014, 1016, 1024, 1026 on the bone portions. Further, the orientation of the alignment opening 1028 to the alignment opening 1030 may change as the length of the plate 1000 and the vertical inclination angle of the osteotomy changes. The change in orientation of the alignment guide openings 1028, 1030 provides a more perpendicular screw fixation relative to the osteotomy by changing the alignment guide placement.

The foot plate guide 1100 is shown in FIGS. 88-90. The foot plate guide 1100 may include a foot plate 1102, a foot plate k-wire guide 1110, a retainer member 1130 and a guide wire, k-wire or the like 1140. The foot plate 1102 may also include a plurality of holes 1106 extending through the plate 1102 from a top surface to a bottom surface. The foot plate k-wire guide 1110 may include a first end 1112 opposite a second end 1114 and a first side 1118 opposite a second side 1120. The foot plate k-wire guide 1110 may also include a center opening 1116 extending between the first and second ends 1112, 1114 and the first and second sides 1118, 1120. The foot plate k-wire guide 1110 may also include a plurality of guide wire openings 1122 extending through each of the first side 1118 and second side 1120. As shown, the plurality of guide wire openings 1122 may be, for example, a plurality of slots 1122 positioned in two columns on each of the first side 1118 and second side 1120. The plurality of openings 1122 may, for example, range from 1 to 26 openings. The openings 1122 may, for example, correspond to the rotation angle as described in greater detail below with respect to the surgical method. When the foot plate k-wire guide 1110 is attached to the foot plate 1102, the openings 1122 may be parallel to the foot plate 1102 allowing for k-wires to be inserted or placed parallel to the ground when the foot is pushed up against the foot plate.

A surgical method of using the osteotomy system of FIGS. 59-87 is shown in FIGS. 88-106. The surgical method may be a proximal rotational metatarsal osteotomy performed through a proximal metatarsal oblique plane osteotomy correcting the deformity through rotation. The surgical method may correct a metatarsal internal rotation and the hallux valgus deformity by rotating the metatarsal through an oblique plane with no bone resection. The surgical method may be performed, for example, with no loss of metatarsal length and a broader bone surface contact than with a transverse proximal osteotomy procedure. The surgical method also may allow for correcting a transverse plane deformity by locating the metatarsal parallel to the second metatarsal and correcting an axial plane deformity, i.e. malrotation, to position the bone, for example, first metatarsal, on top of the sesamoids. The surgical method results in a complete transverse and coronal plane deformity correction.

The surgical method may include evaluating the severity of the deformity on an anterior-posterior foot x-ray by measuring the intermetatarsal angle. The intermetatarsal angle is obtained by measuring the divergence between the first and second metatarsals. Next, the angle to be corrected is measured to determine the degrees necessary to place the metatarsal head over the sesamoid complex. There may be a limited capacity to evaluate the metatarsal malrotation, due to sesamoid subluxation. In one embodiment, axial sesamoid x-rays can give a rough estimate of first ray malrotation. In another embodiment, a preoperative CT scan may be performed, which could assess metatarsal rotation and sesamoid subluxation. In another embodiment, the metatarsal rotation angle may be assessed by measuring the angle between the floor and hallux with a goniometer.

Once the intermetatarsal angle and rotation angle are determined, then the angle of correction or osteotomy cut angle may be determined. In order to avoid having to perform calculations during surgery, the angle of correction or osteotomy cut angle may be determined using Table 5 below. Table 5 includes the most commonly seen values for rotation angle and the most common intermetatarsal angles. In addition, Table 5 includes the osteotomy cut angle selected for each group of rotation angles and intermetatarsal angles. Therefore, it is also contemplated that in alternative embodiments, the osteotomy cut angles listed in Table 5 may be different based on an alternative grouping of the rotation angles and intermetatarsal angles. If there is a remaining interphalangeal deformity then an optional phalangeal osteotomy, for example, an Akin osteotomy, may be performed.

TABLE 5

| | | Rotation Angle | | | |
|---|---|---|---|---|---|
| | | 10°-19° | 20°-29° | 30°-39° | 40°-50° |
| Intermetatarsal Angle | 8°-10° | 38 | 28 | 23 | 13 |
| | 11°-12° | 47 | 33 | 28 | 18 |
| | 13°-14° | 55 | 38 | 33 | 23 |
| | 15°-17° | 55 | 42 | 38 | 28 |
| | 18°-20° | 55 | 47 | 42 | 33 |

Once the correction is determined, a medial approach may be performed. The method may include making an incision, for example, a medial or dorsomedial incision, over the proximal first metatarsal. The method may also optionally include a lateral release for hallux valgus correction to relocate the first metatarsal above the sesamoids. Next, the method may include dissection that is carried down to the base of the first metatarsal. Then, a line or marking 1052 may be etched on the first metatarsal, for example, along the medial midline using a bovie, light skiving with a sagittal saw, electrocautery, or marking pen, as shown in FIGS. 92-101.

Next, the foot plate guide 1100 may be assembled by obtaining a foot plate 1102, a foot plate k-wire guide 1110, and a retainer member 1130. The feet 1124 of the foot plate k-wire guide 1110 may be inserted into the plurality of holes 1106 in the foot plate 1102 from a top surface, as shown in FIGS. 88-90. The securement openings 1136 of the retainer member 1130 may be aligned with the feet 1124 of the guide 1110 on a bottom surface of the foot plate 1102 and positioned to secure or lock the retainer member 1130 and guide 1110 to the foot plate 1102, as shown in FIGS. 89 and 90.

With continued reference to FIGS. 89 and 90, the method may further include placing the patient's foot on the foot plate 1102. Then, using fluoroscopy the first tarsometatarsal joint may be located and a point, for example, approximately 1-2 cm from the joint may be marked. In an embodiment, where the osteotomy cut angle is less than 47°, the point from the first tarsometatarsal joint may be, for example, approximately 1-1.5 cm from the joint. In another embodiment, where the osteotomy cut angle is greater or equal to 47°, the point from the first tarsometatarsal joint may be, for example, approximately 1.5-2 cm from the joint. Once the point is determined, a k-wire 1140 may be obtained and inserted through the guide 1110 and into the patient's foot. The k-wire 1140 may be inserted, for example, parallel to the weight-bearing surface, as guided by the foot plate k-wire guide 1110. In addition, the k-wire 1140 may be inserted, for example, perpendicular to the long axis of the first metatarsal. After the k-wire 1140 is inserted into the first metatarsal, fluoroscopy may be used to confirm the position of the k-wire 1140. Once the k-wire 1140 is in the desired position, the foot plate k-wire guide 1110 of the coupled foot plate guide 1100 may be slid off the k-wire 1140 and the foot plate guide 1100 may be disassembled after removal from the patient.

Figure 91:
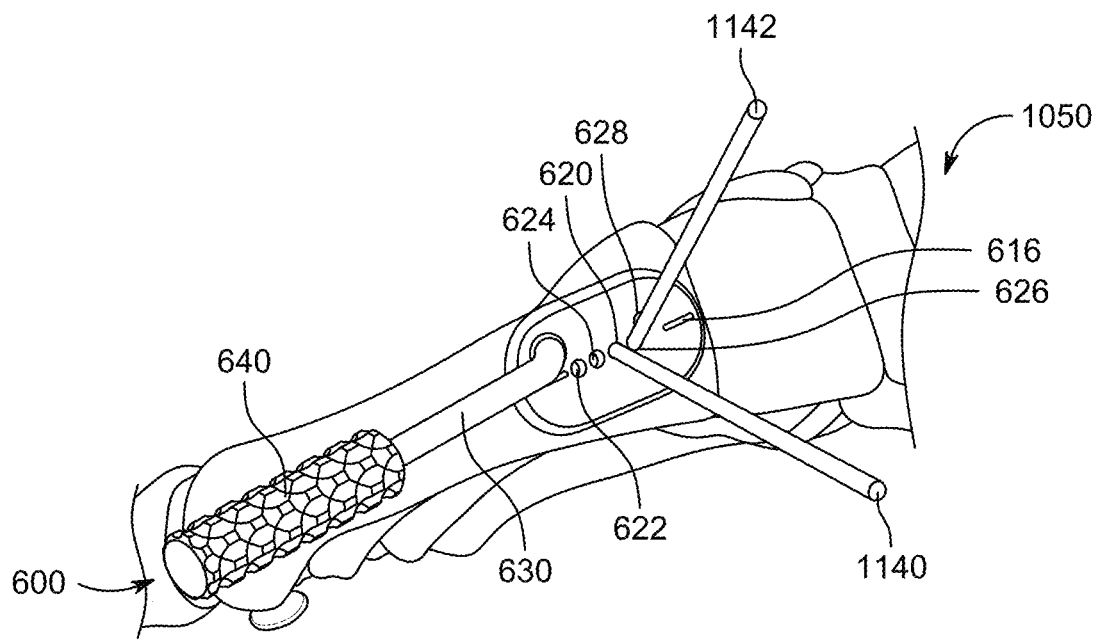
FIG. 91 is a side perspective view of the foot of FIG. 90 with the alignment device of FIG. 59 positioned on the foot, in accordance with an aspect of the present invention.

Referring now to FIG. 91, the zero opening 620 of the alignment device 600 may be slid over the k-wire 1140 and the bottom surface 614 of the alignment device 600 positioned on the foot 1050. Then, the at least one alignment marking 616 may be aligned with a bone marking or laser marking 1052 on the first metatarsal of the foot 1050. Based on the determined angle of correction, i.e., the rotation angle, a second k-wire or guide wire 1142 may be obtained and inserted into one of the openings 622, 624, 626, 628 that corresponds to the desire rotation angle from Table 5. For example, the second k-wire 1142 may be inserted into the third angled opening 626, as shown in FIG. 91. Next, the first k-wire 1140 may be removed from the patient.

Figure 92:
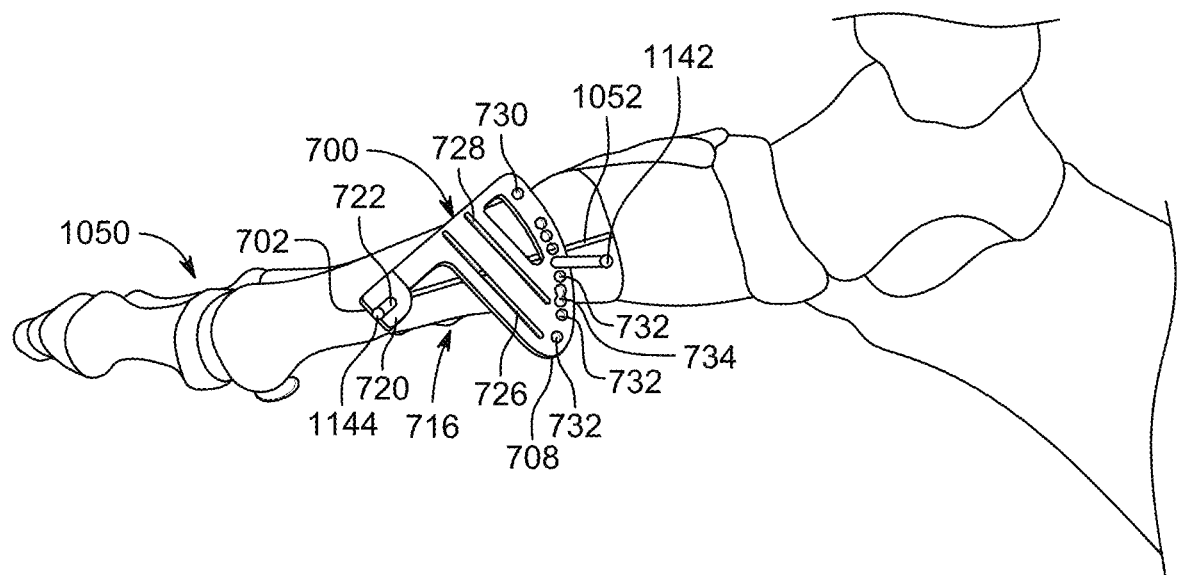
FIG. 92 is a side perspective view of the foot of FIG. 91 with the cut guide of FIG. 66 positioned on the foot, in accordance with an aspect of the present invention.
Figure 93:
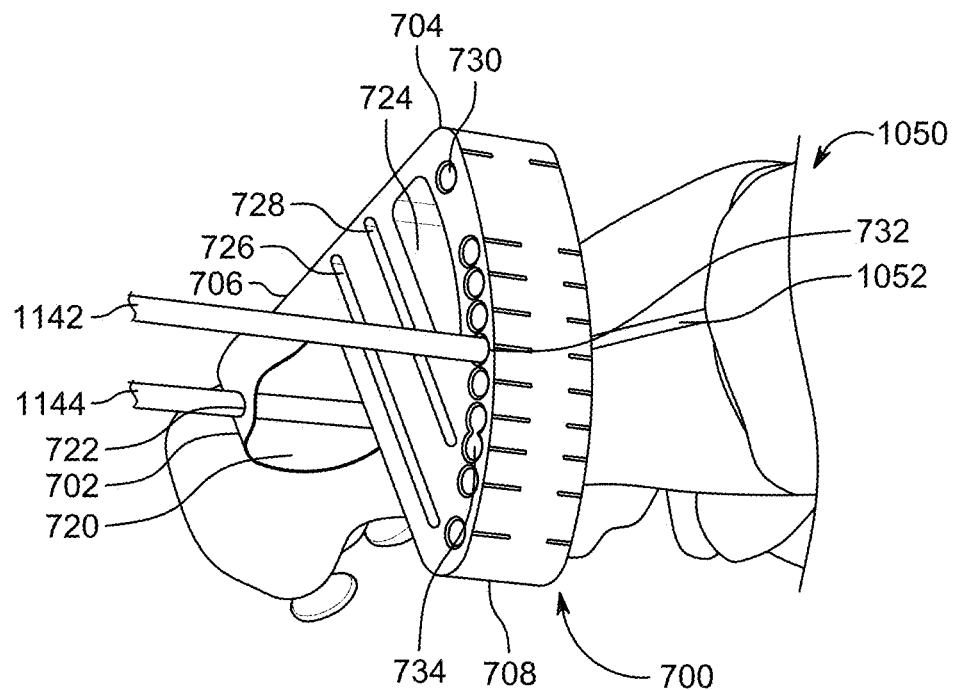
FIG. 93 is a proximal end, perspective view of the foot and cut guide of FIG. 92, in accordance with an aspect of the present invention.

As shown in FIGS. 92 and 93, the cut guide 700 may be positioned on the foot 1050. The opening 730, 732, 734 corresponding to the desired osteotomy cut angle may be slid over the second k-wire 1142. The side 710, 712 corresponding to the operative side of the cut guide 700 may be positioned away from the foot 1050, as shown in FIGS. 92 and 93. The distal end 702 of the cut guide 700 may be aligned on the bone marking 1052. Then, a third k-wire 1144 may be inserted through the opening 722 in the distal end 702 of the cutting guide 700 to intersect with the bone marking 1052.

Figure 94:
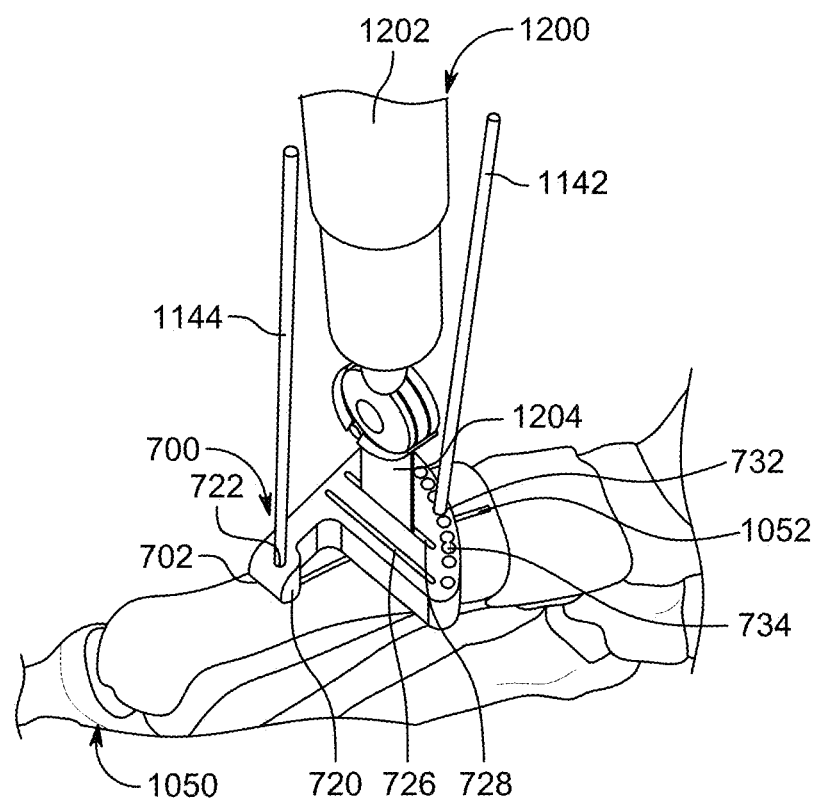
FIG. 94 is a side perspective view of the foot and cut guide of FIG. 92 with a saw inserted through the cut guide, in accordance with an aspect of the present invention.
Figure 95:
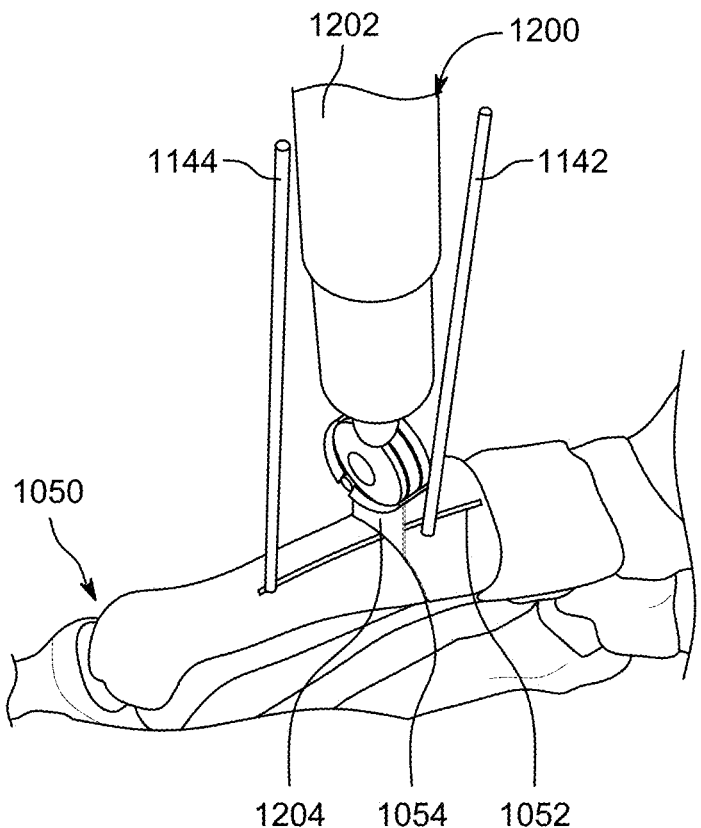
FIG. 95 is a side perspective view of the foot of FIG. 94 after the cut guide is removed, in accordance with an aspect of the present invention.

Referring now to FIG. 94, the saw 1200 may be used to perform the osteotomy. For example, the saw blade 1204 may be inserted through the cutting slot 726, 728 in the cut guide 700 to cut the first metatarsal. The cutting slot 726 may be, for example, used when a 55° osteotomy cut angle is calculated or when it is determined that the first k-wire 1140 was placed too close to the joint and the osteotomy cut should be at a more distal location to avoid the first tarsometatarsal joint space. In all other instances, the cutting slot 728 should be used. As shown in FIG. 94, the saw blade 1204 may be inserted into the second cutting slot 728 to cut the first metatarsal. After the saw blade 1204 passes through the entire selected cutting slot 726, 728, the cut guide 700 may be removed from the foot 1050. Then, the saw blade 1204 may be used to complete the osteotomy cut 1054, as shown in FIG. 95.

Figure 96:
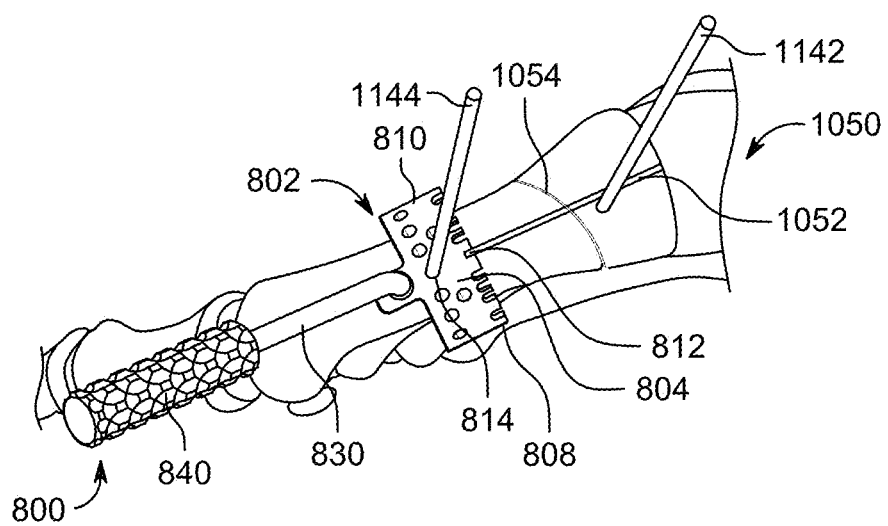
FIG. 96 is a side perspective view of the foot of FIG. 95 with the saw removed and the position rotation device of FIG. 72 positioned on the foot, in accordance with an aspect of the present invention.

After the osteotomy cut 1054 is complete, the position rotation device 800 may be inserted onto the distal k-wire 1144 in the foot 1050, as shown in FIG. 96. The first or zero opening 814 may be aligned with the distal k-wire 1144 and the position rotation device 800 may be slid onto the k-wire 1144. The position rotation device 800 may then be aligned onto the first metatarsal.

Figure 97:
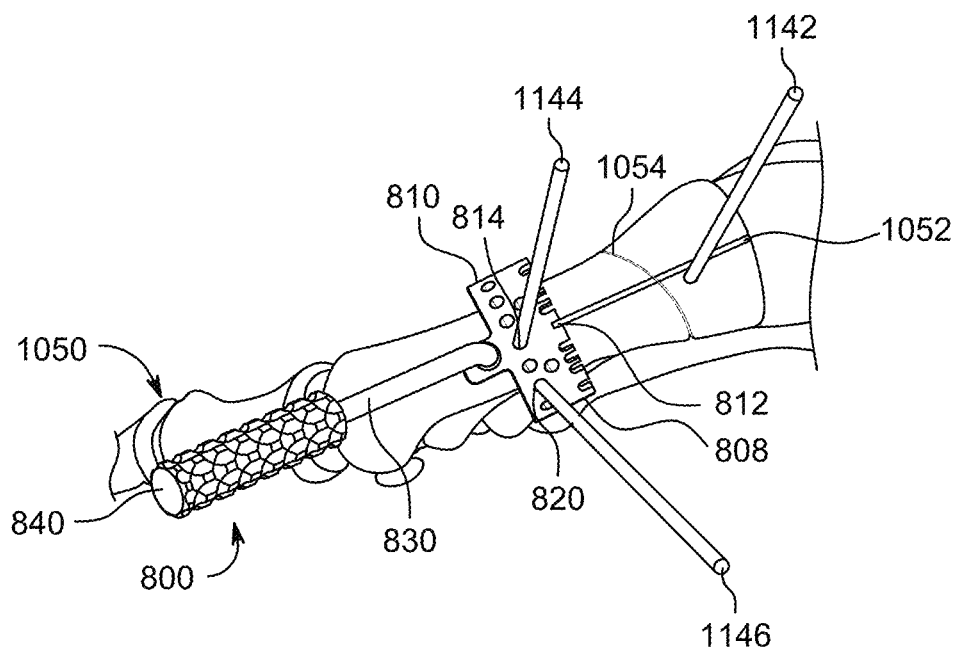
FIG. 97 is a side perspective view of the foot of FIG. 96 with a second k-wire inserted through the position rotation device, in accordance with an aspect of the present invention.

Next, as shown in FIG. 97, another k-wire 1146 may be inserted into an opening 816, 818, 820, 822 that corresponds to the rotation angle positioned below the bone marking 1052. In the depicted embodiment, the k-wire 1146 is inserted into the third angled opening 820 near the first end 808 of the position rotation device 800. Then, the k-wire 1144 and the position rotation device 800 may be removed from the foot 1050, as shown in FIG. 98.

Figure 98:
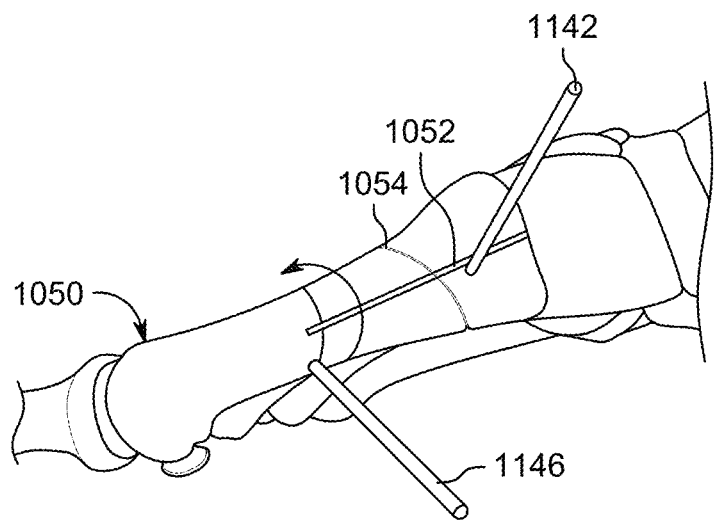
FIG. 98 is a side perspective view of the foot of FIG. 97 with the position rotation device removed, in accordance with an aspect of the present invention.
Figure 99:
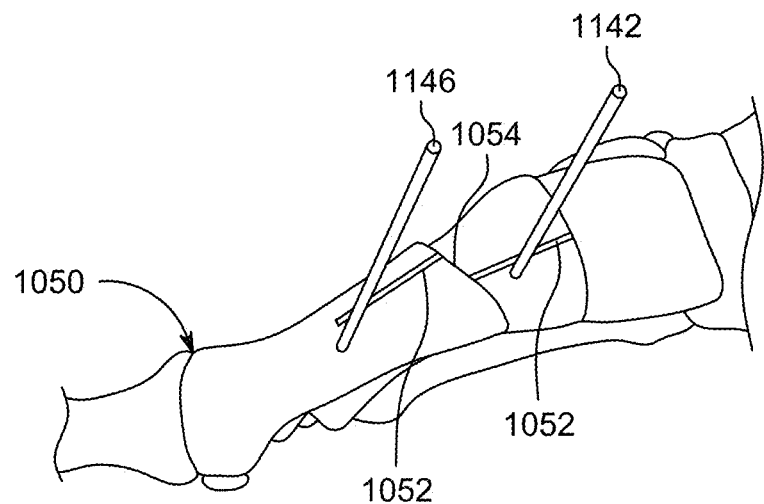
FIG. 99 is a side perspective view of the foot of FIG. 98 after rotation of distal bone segment, in accordance with an aspect of the present invention.
Figure 100:
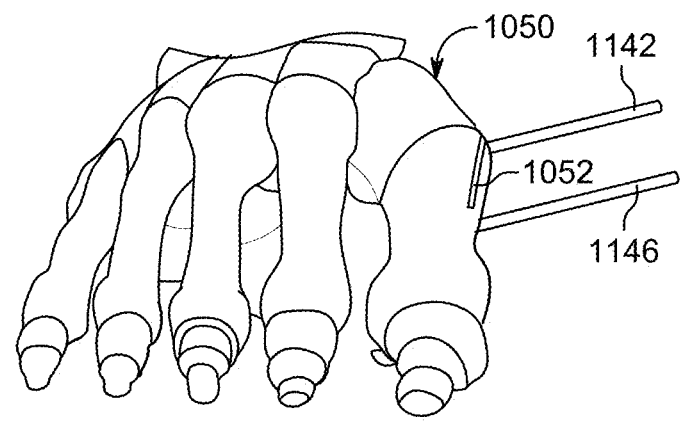
FIG. 100 is a distal end view of the foot of FIG. 99, in accordance with an aspect of the present invention.
Figure 101:
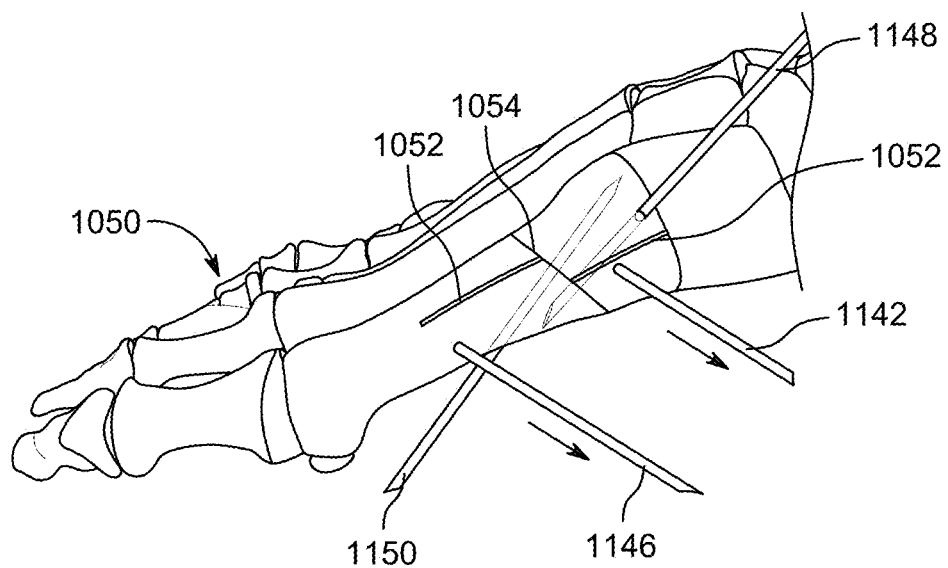
FIG. 101 is a side perspective view of the foot of FIG. 100 with temporary fixation members inserted across the osteotomy, in accordance with an aspect of the present invention.

Referring now to FIGS. 98 and 99, the k-wire 1146 positioned in the distal portion of the metatarsal may be rotated out of valgus until the distal k-wire 1146 is parallel with the k-wire 1142 positioned in the proximal portion of the metatarsal along the medial aspect of the first metatarsal. The distal k-wire 1146 may be rotated to the identified malrotation angle. The distal k-wire 1146 may be rotated with, for example, a lobster claw clamp (not shown) or pointed reduction forceps (not shown). Once the distal portion of the metatarsal is rotated, as shown in FIGS. 99 and 100, the method may include confirming that the medial cortex is flush without any step-off medially and with or without a dorsal step-off. Next, as shown in FIG. 101, a k-wire 1148 may be inserted into the foot 1050 across the osteotomy site 1054 from, for example, a dorsal to plantar direction to temporarily fix the osteotomy 1054. Then, another k-wire 1150 may be inserted from, for example, a plantar to dorsal direction for additional temporary fixation of the osteotomy site 1054. The method may also include using fluoroscopy to check correction. If the desired correction is achieved, then the k-wires 1142, 1146 may be removed.

Figure 102:
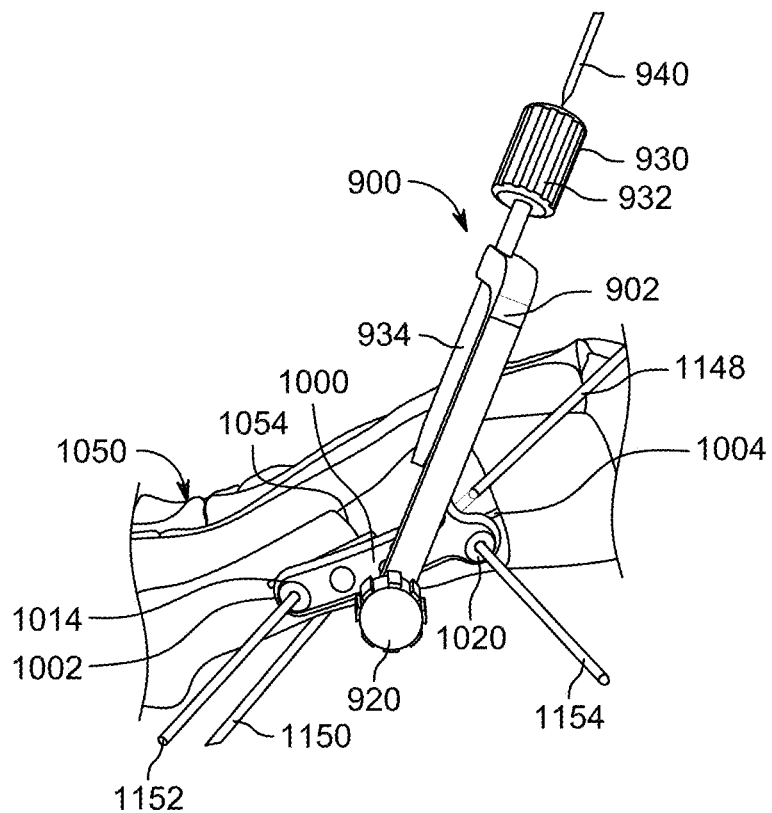
FIG. 102 is a side perspective view of the foot of FIG. 101 after the coupled alignment guide of FIG. 78 and the bone plate of FIG. 81 are attached to the foot, in accordance with an aspect of the present invention.
Figure 103:
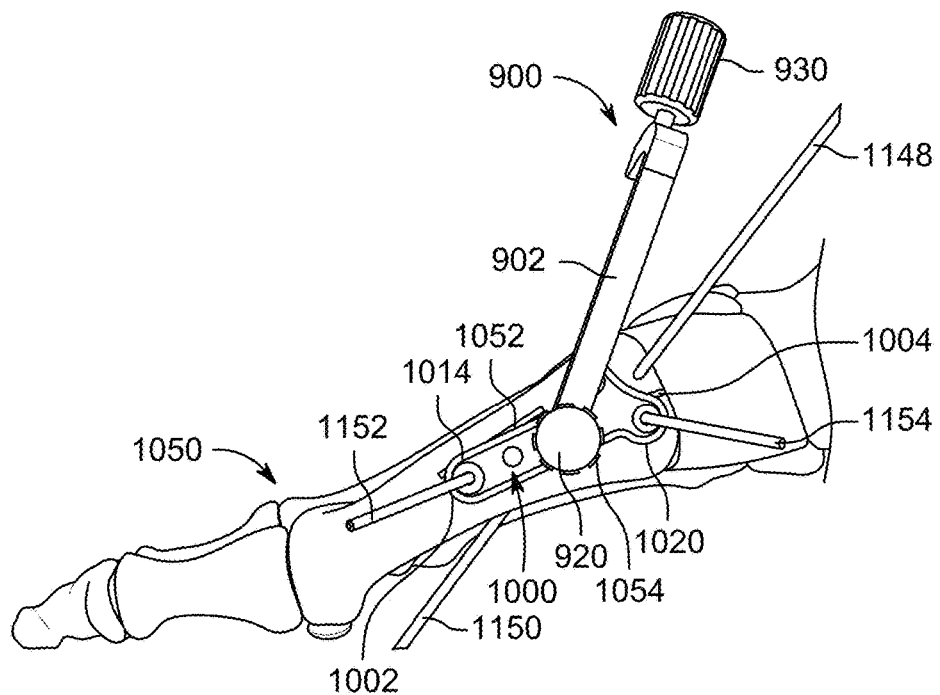
FIG. 103 is a side perspective view of the foot of FIG. 102 with the k-wire being inserted into the foot, in accordance with an aspect of the present invention.

The method may further include fixing the osteotomy site 1054, as shown in FIGS. 102-106. For example, obtaining an alignment guide 900 and a plate 1000 and coupling the plate 1000 to the alignment guide 900. The plate 1000 may be selected based on the osteotomy cut angle. The plate 1000 may be aligned with the alignment guide 900 by positioning the alignment protrusion 910 of the alignment guide 900, as shown in FIGS. 78-80, in the second alignment guide opening 1030 in the plate 1000, as shown in FIGS. 81 and 84-87. The plate 100 may be coupled to the alignment guide 900 by inserting the engagement portion 926 of the alignment guide 900 into the first alignment guide opening 1028 of the plate 1000, as discussed in greater detail above, which will not be described again here for brevity sake. Next, the coupled alignment guide 900 and plate 1000 may be placed medially on the first metatarsal, as shown in FIGS. 102 and 103. The plate 1000 may be centered along the long axis of the first metatarsal. In addition, the distal openings 1014, 1016 and the proximal openings 1024, 1026 may be positioned approximately equidistant from the osteotomy site 1054. Once the plate 1000 is in the desired position, the plate 1000 may be secured to the first metatarsal of the foot 1050 using at least one olive wire or fastener 1152, 1154. Next, the placement of the plate 1000 may be checked using fluoroscopy.

Figure 104:
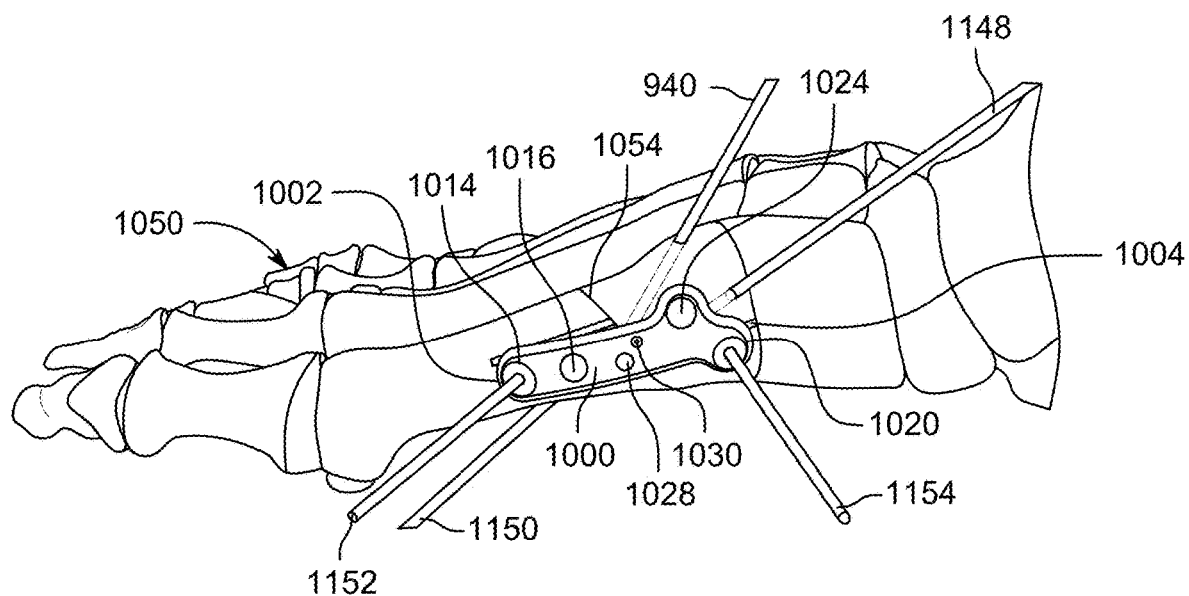
FIG. 104 is a side perspective view of the foot of FIG. 103 with the alignment guide removed from the plate, in accordance with an aspect of the present invention.
Figure 105:
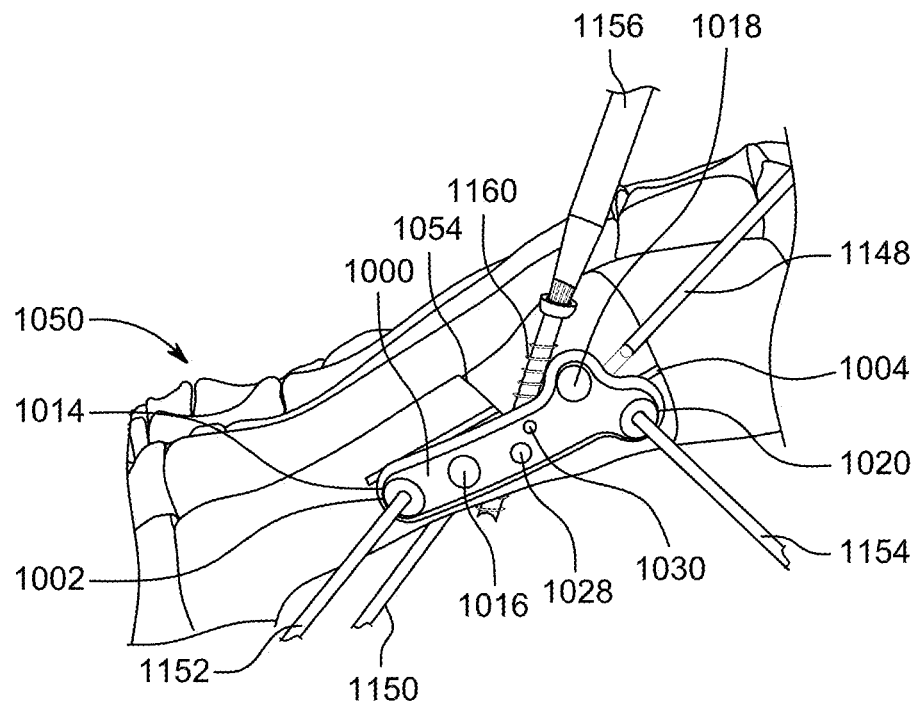
FIG. 105 is a side perspective view of the foot of FIG. 104 with a compression screw inserted across the osteotomy site, in accordance with an aspect of the present invention.
Figure 106:
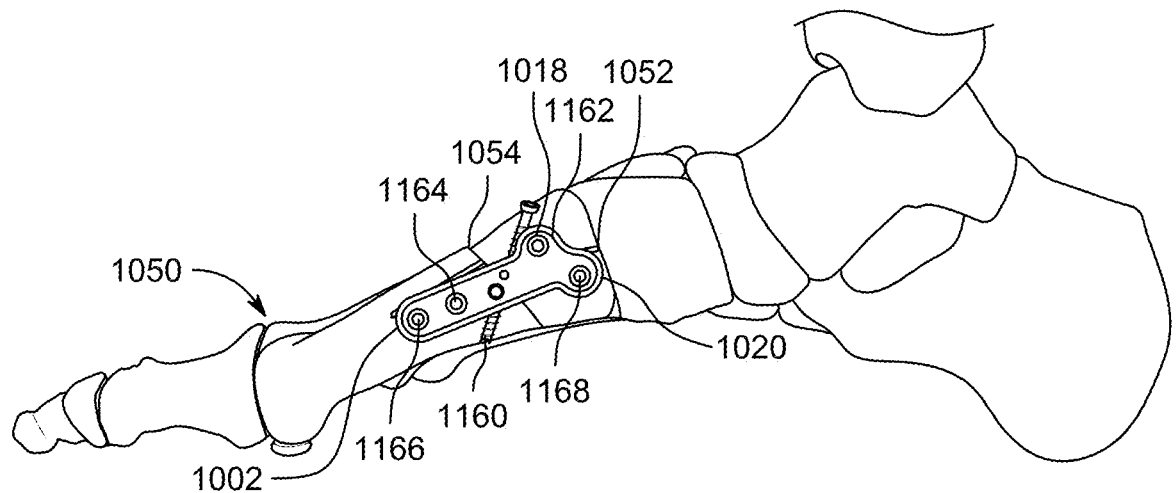
FIG. 106 is a side perspective view of the foot of FIG. 105 after the bone screws are inserted to secure the plate over the osteotomy site, in accordance with an aspect of the present invention.
Figure 107:
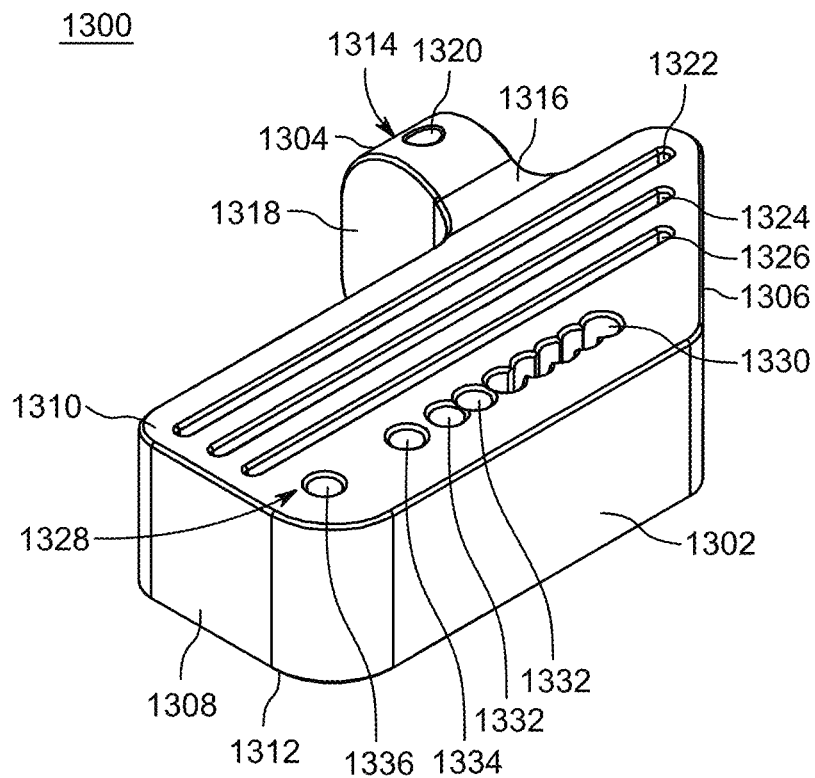
FIG. 107 is a first end perspective view of another cut guide, in accordance with an aspect of the present invention.
Figure 108:
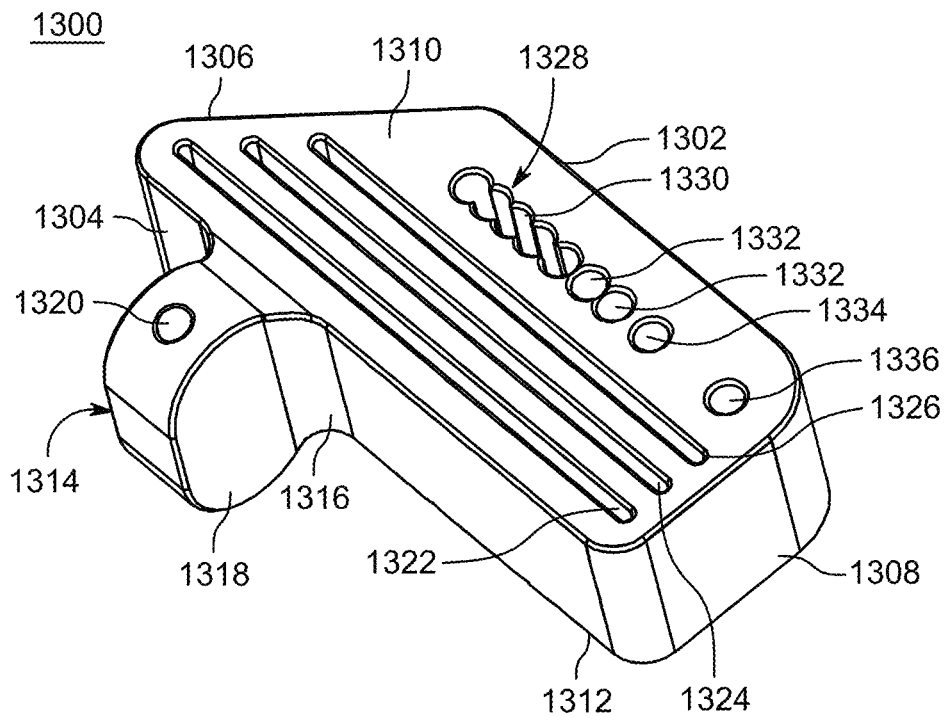
FIG. 108 is a second end perspective view of the cut guide of FIG. 107, in accordance with an aspect of the present invention.
Figure 109:
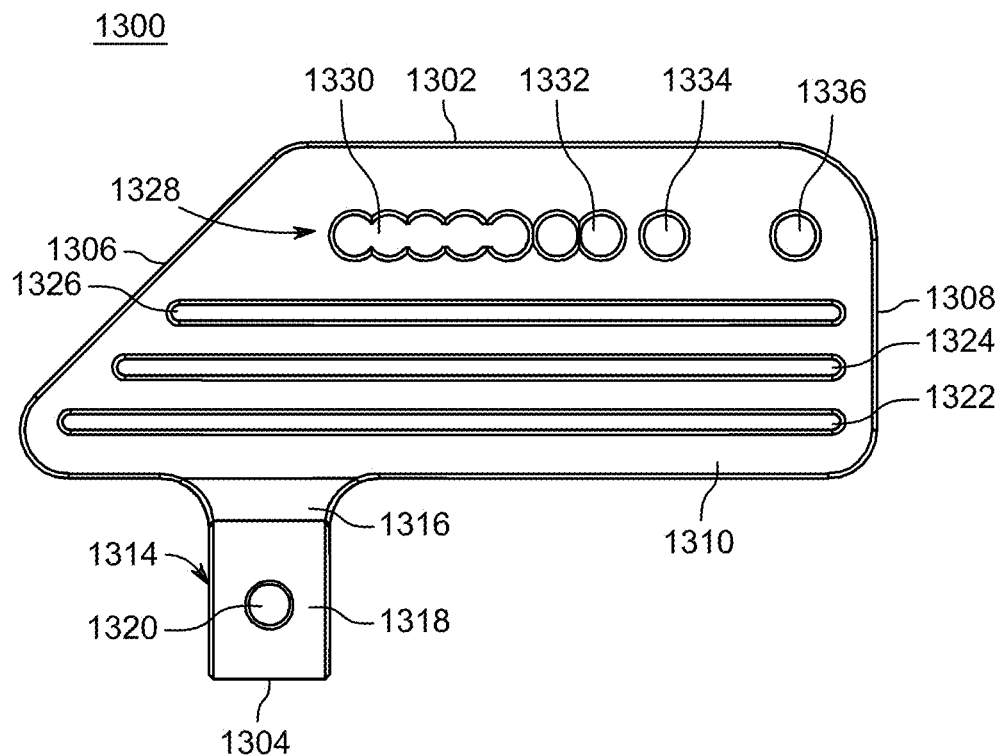
FIG. 109 is a right side view of the cut guide of FIG. 107, in accordance with an aspect of the present invention.
Figure 110:
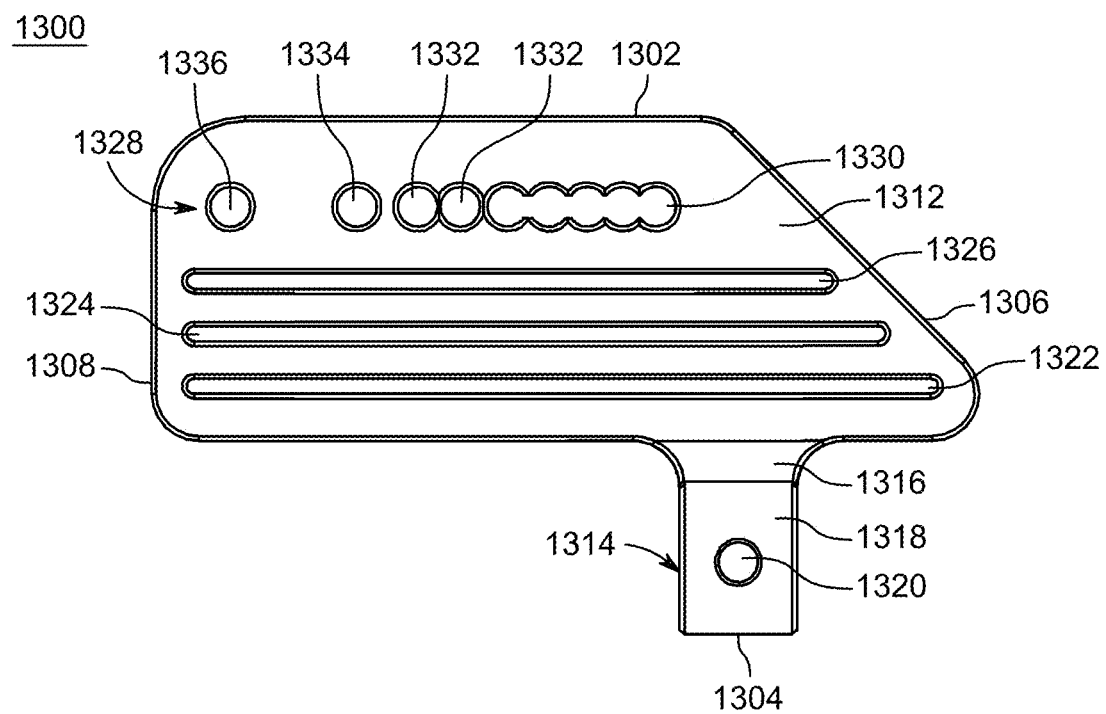
FIG. 110 is a left side view of the cut guide of FIG. 107, in accordance with an aspect of the present invention.

After the plate 1000 is temporarily secured to the first metatarsal using the olive wires 1152, 1154, a k-wire 940 may be inserted through the tissue protector 930 of the alignment guide 900 and across the osteotomy site 1054, as shown in FIG. 103. The position and length of the k-wire 940 may then be checked using fluoroscopy. When the k-wire 940 is in the correct position, the alignment guide 900 may be removed from the plate 1000, as shown in FIG. 104. The alignment guide 900 may be removed by, for example, disengaging the engagement portion 926 of the fixation member 920 from the plate 1000 and sliding the tissue protector 930 off the k-wire 940. Next, a cannulated drill may be inserted over the k-wire 940 to drill an opening (not shown) for inserting a compression screw 1160 across the osteotomy site 1054. After drilling the opening (not shown), the compression screw 1160 should be selected by, for example, taking measurements for the size and length of the screw 1160 needed. The selected compression screw 1160 may then be inserted across the osteotomy site 1054 and if necessary, countersunk into the metatarsal bone, as shown in FIG. 105. The compression screw 1160 may be inserted in a dorsal to plantar direction, as shown, or a plantar to dorsal direction by pushing the k-wire 940 most of the way through the metatarsal bone. Once the compression screw 1160 is secured across the osteotomy site 1054, the k-wire 940 may be removed from the patient's foot 1050, as shown in FIG. 106. Then, bone screws 1162, 1164, 1166, 1168 may be inserted through the openings 1014, 1016, 1024, 1026 and into the foot 1050, as shown in FIG. 106. After the screws 1162, 1164, 1166, 1168 are inserted into the foot 1050, fluoroscopy may be used to confirm the position of the plate 1000 and screws 1162, 1164, 1166, 1168.

When necessary, depending on the interphalangeal angle and metatarsophalangeal soft tissue balance, an Akin osteotomy may be performed to complete the correction. Finally, the final toe rotation may be checked and once the desired rotation is achieved the patient's incision may be closed.

Figure 111:
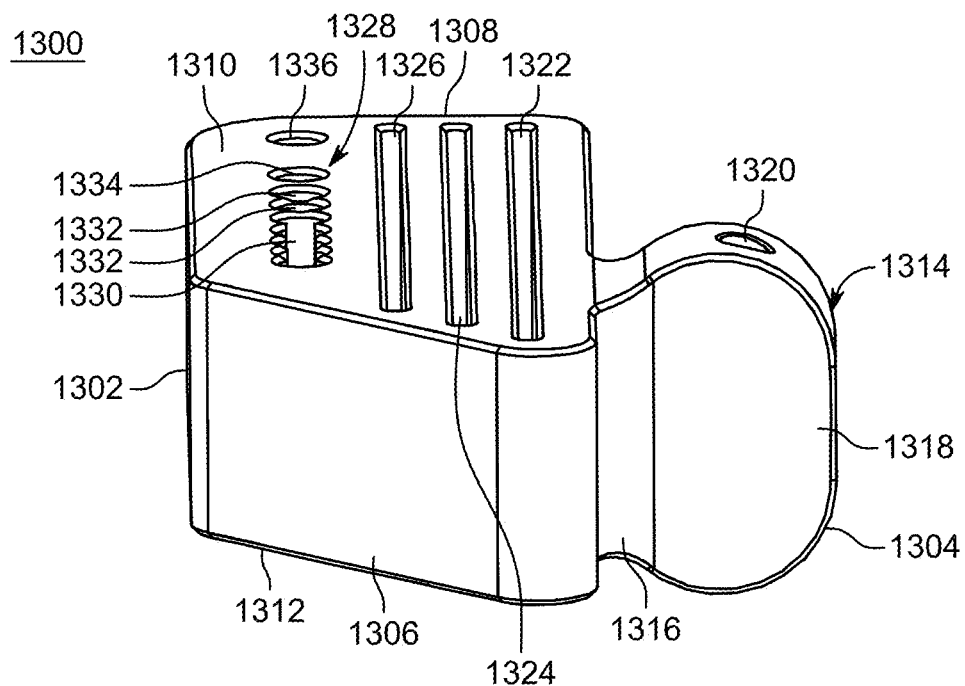
FIG. 111 is a first side perspective view of the cut guide of FIG. 107, in accordance with an aspect of the present invention.
Figure 112:
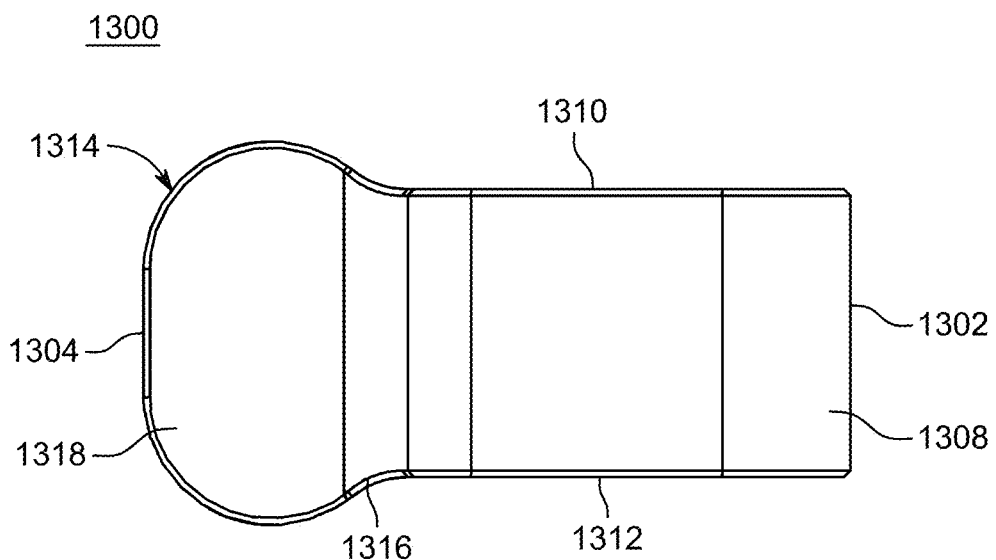
FIG. 112 is a second side view of the cut guide of FIG. 107, in accordance with an aspect of the present invention.
Figure 113:
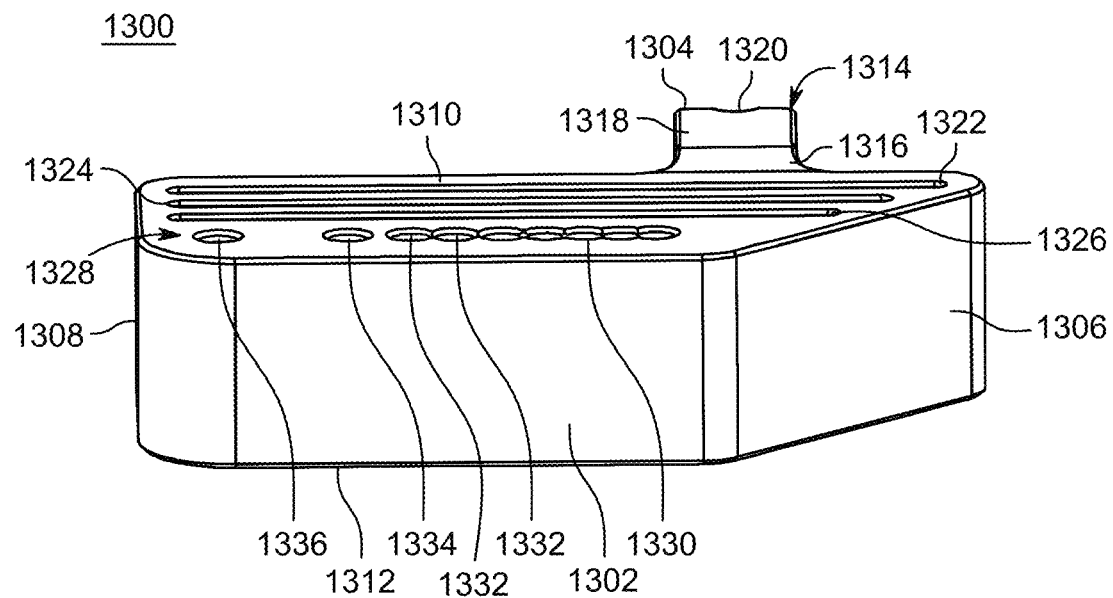
FIG. 113 is a first end perspective view of the cut guide of FIG. 107, in accordance with an aspect of the present invention.
Figure 114:
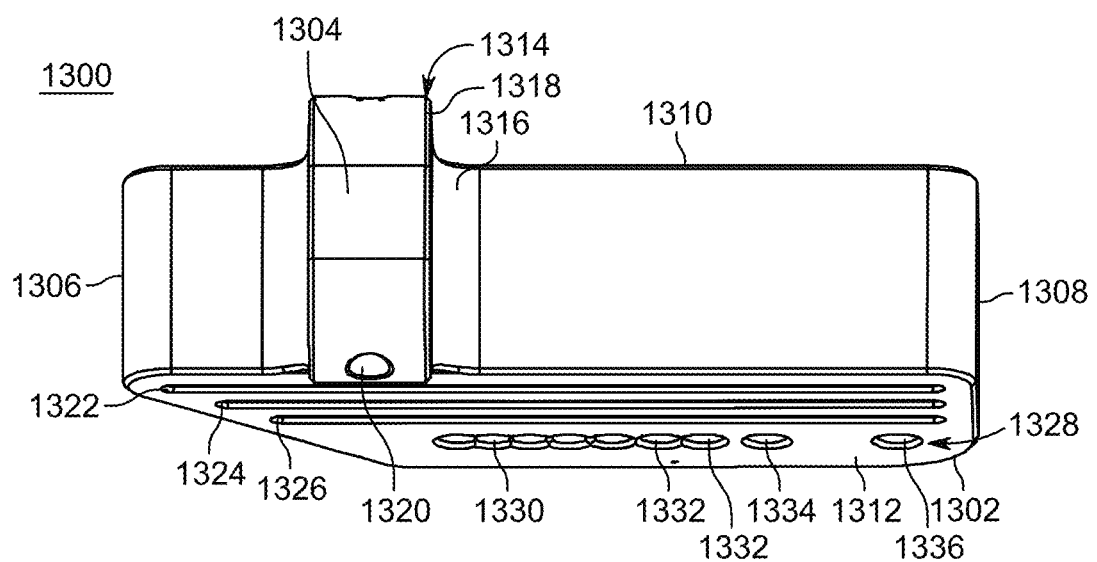
FIG. 114 is a second end perspective view of the cut guide of FIG. 107, in accordance with an aspect of the present invention.
Figure 115:
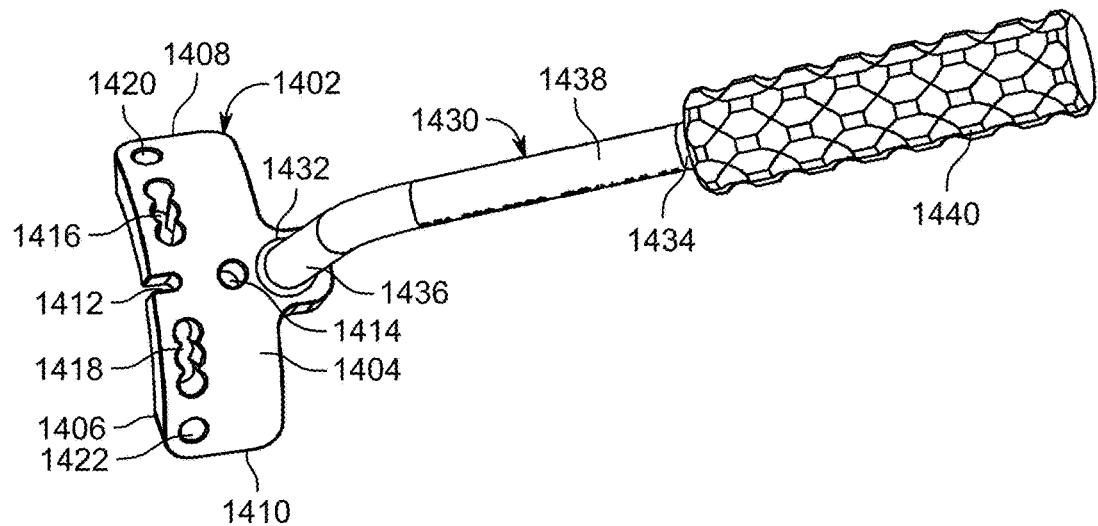
FIG. 115 is a top perspective view of another position rotation device, in accordance with an aspect of the present invention.
Figure 116:
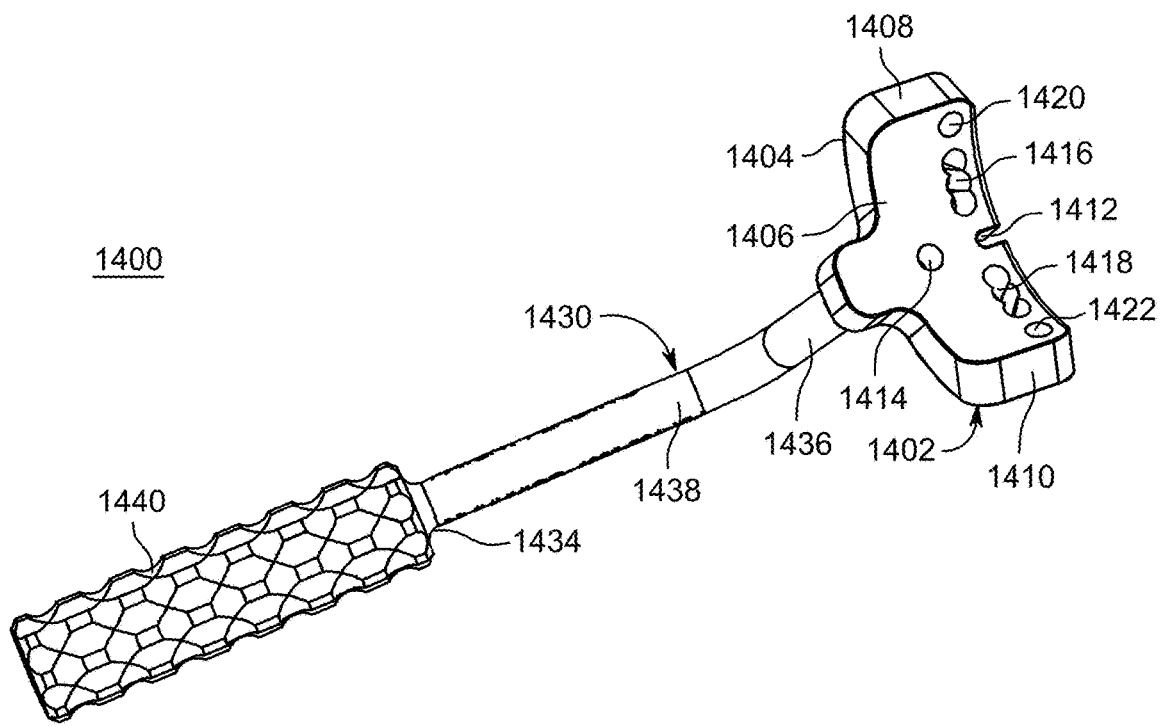
FIG. 116 is a bottom perspective view of the position rotation device of FIG. 115, in accordance with an aspect of the present invention.

Referring now to FIGS. 107-114, another cut guide 1300 is shown. The cut guide 1300 includes a first or proximal end 1302 positioned opposite a second or distal end 1304, a first side 1306 positioned opposite a second side 1308, and a right side 1310 positioned opposite a left side 1312. The first side 1306 may be, for example, angled as it extends from the proximal end 1302 to the distal end 1304. The right side 1310 may be, for example, positioned parallel to the left side 1312, as shown in FIG. 112. The cut guide 1300 may include an extension member 1314 extending away from the cut guide 1300 to the distal end 1304. The extension member 1314 may include a leg portion 1316 extending from a side of the cut guide 1300 and a foot portion 1318 extending away from the leg portion 1316. The foot portion 1318 may, for example, have a height that is greater than a height of the leg portion 1316, as shown in FIGS. 111, 112 and 114. The right side 1306 may include, for example, a curved portion from the leg portion 1316 to the foot portion 1318 and the left side 1308 may also include, for example, a curved portion from the leg portion 1316 to the foot portion 1318. The foot portion 1318 may include an opening 1320 extending through the foot portion 1318 from the right side 1310 to the left side 1312. The opening 1320 may receive a guide wire, k-wire, or the like, to position the cut guide 1300 on a bone.

With continued reference to FIGS. 107-114, the cut guide 1300 may also include at least one cutting slot 1322, 1324, 1326 extending between the first side 1306 and the second side 1308. The at least one cutting slot 1322, 1324, 1326 may extend through the cut guide 1300 from the right side 1310 to the left side 1312. As shown in FIGS. 107-111 and 113-114, the cut guide 1300 may include, for example, three cutting slots 1322, 1324, 1326. The first cutting slot 1322 may be positioned, for example, adjacent to the distal end 1304 of the cutting guide 1300. The second cutting slot 1324 may be positioned, for example, adjacent to the first cutting slot 1322. The third cutting slot 1326 may be positioned, for example, toward the proximal end 1302 of the cutting guide 1300 and adjacent to the second cutting slot 1324. The second cutting slot 1324 may be positioned, for example, between the first cutting slot 1322 and the third cutting slot 1326. Each of the cutting slots 1322, 1324, 1326 may be, for example, positioned parallel to each other.

The cut guide 1300 may further include a plurality of openings 1328 positioned, for example, along the proximal end 1302 of the cut guide 1300, as shown in FIGS. 107-111, 113, and 114. The plurality of openings 1328 may include, for example, overlapping openings 1330, adjacent openings 1332, and individual openings 1334, 1336. The overlapping openings 1330 may include, for example, at least two openings that overlap to form a channel of openings. As depicted, the overlapping openings 1330 may include five openings that overlap. The adjacent openings 1332 may include, for example, at least two openings that are positioned directly next to each other and which do not overlap. In the illustrated embodiment, the cut guide 1300 includes the overlapping openings 1330 with five openings positioned proximate to the two adjacent openings 1332, the opening 1334 is positioned aligned with and spaced apart from the adjacent opening 1332, and the opening 1336 is positioned aligned with and spaced apart from the opening 1334. The openings 1330, 1332, 1334, 1336 may be sized and shaped or configured to receive a k-wire, guide wire, or the like, for engaging a bone of a patient. The openings 1330, 1332, 1334, 1336 may extend through the cut guide 1300 from the right side 1310 to the left side 1312. The openings 1330, 1332, 1334, 1336 may correspond to varying degrees of vertical inclination. In one embodiment, vertical inclination of the openings 1330, 1332, 1334, 1336 may range from, for example, approximately 13° to approximately 55°. In one embodiment, the openings 1330, 1332, 1334, 1336 may have vertical inclinations of, for example, 13°, 18°, 23°, 28°, 33°, 38°, 42°, 47° and 55°. In another embodiment, the openings 1330, 1332, 1334, 1336 may have vertical inclinations of, for example, at least one of 11°, 14°, 16°, 18°, 19°, 21°, 22°, 24°, 25°, 28°, 29°, 31°, 32°, 37°, 38°, 43°, 47°, and 51°. Alternative combinations of angles between approximately 13° to approximately 55° are also contemplated as would be understood by one of ordinary skill in the art.

Figure 117:
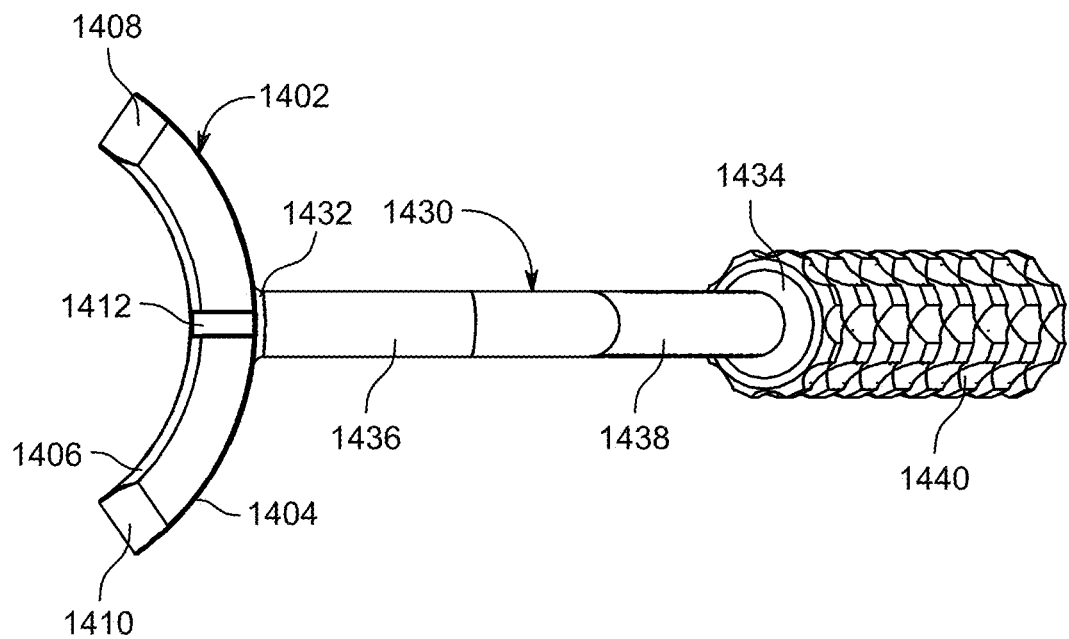
FIG. 117 is first side view of the position rotation device of FIG. 115, in accordance with an aspect of the present invention.
Figure 118:
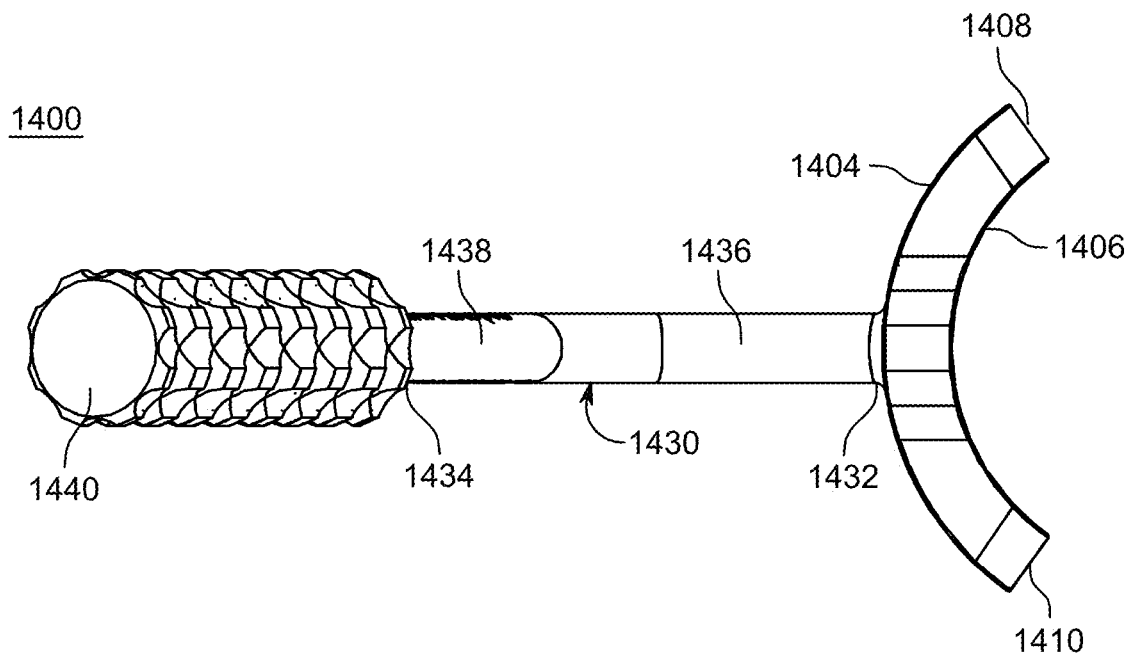
FIG. 118 is a second side view of the position rotation device of FIG. 115, in accordance with an aspect of the present invention.
Figure 119:
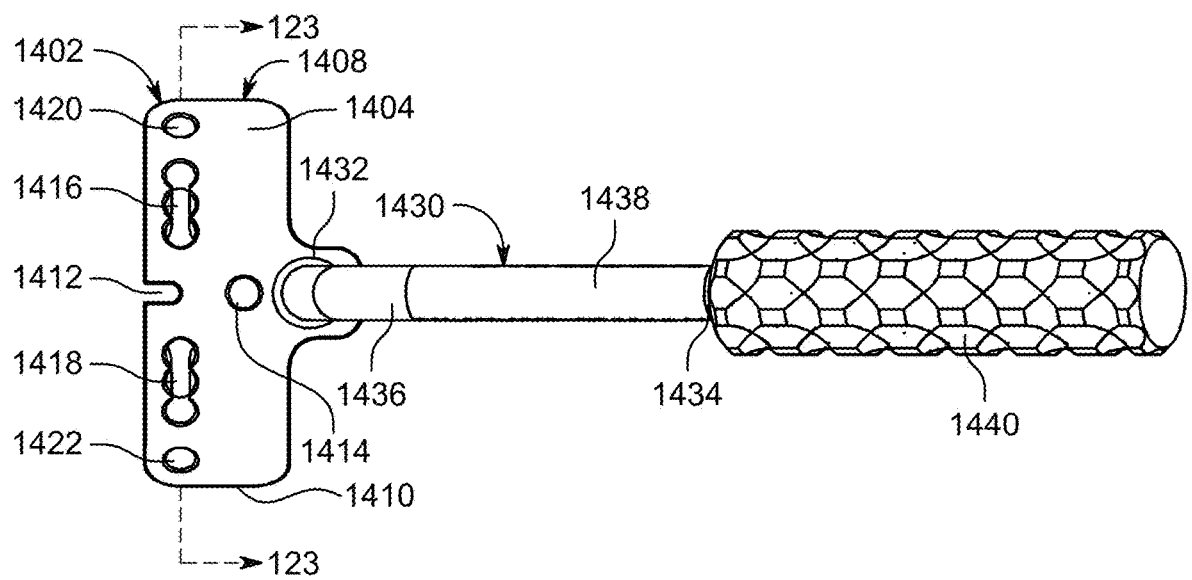
Figure 120:
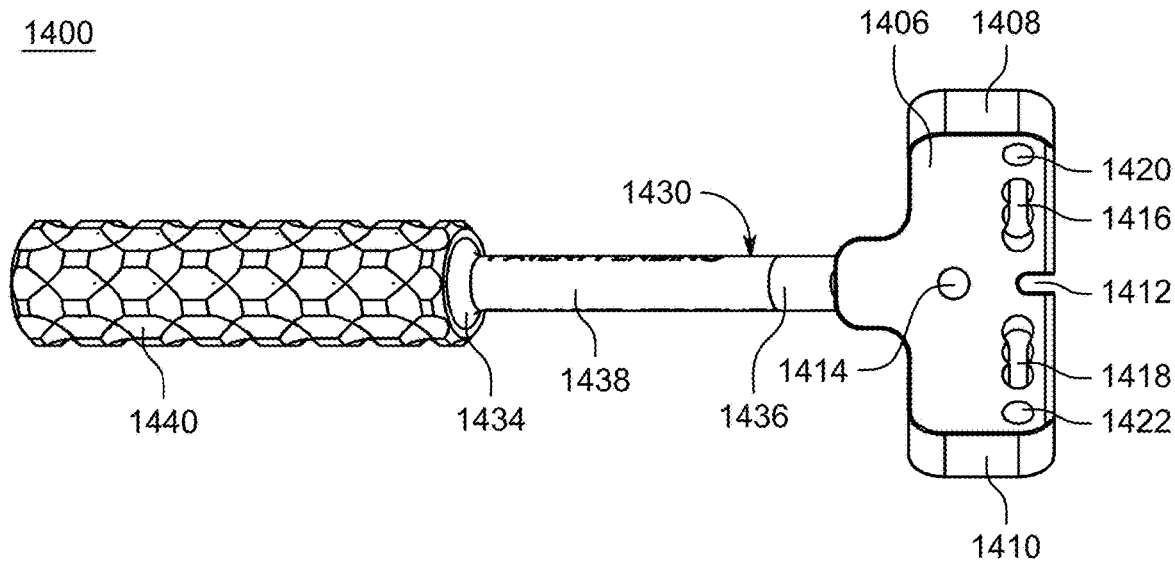
Figure 121:
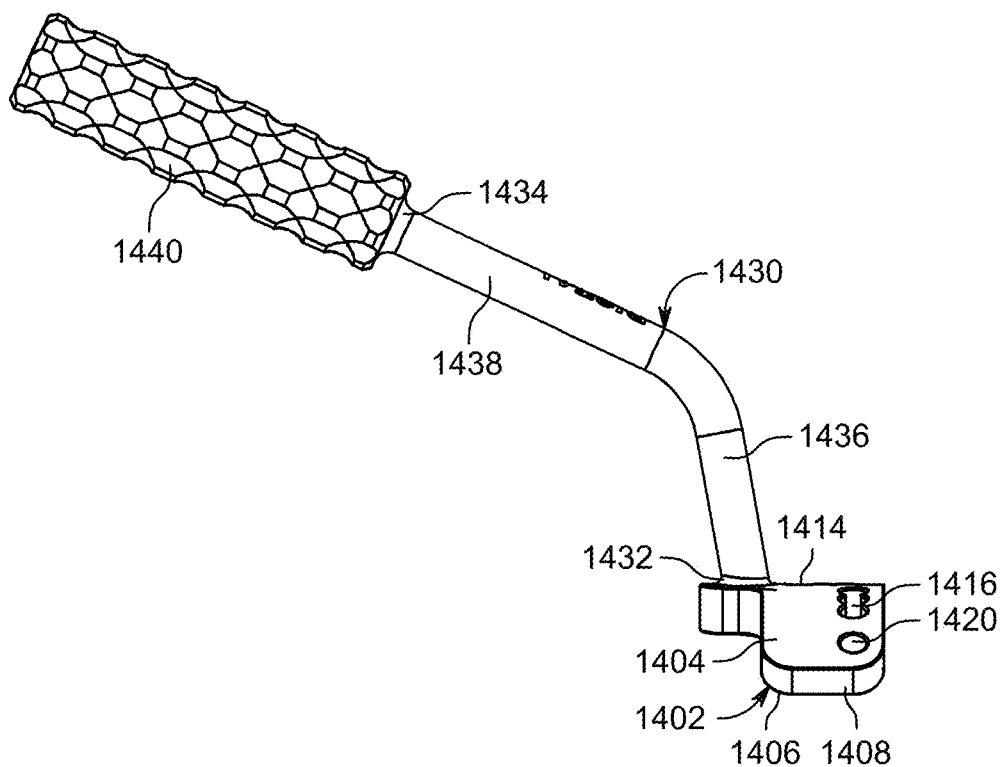
Figure 122:
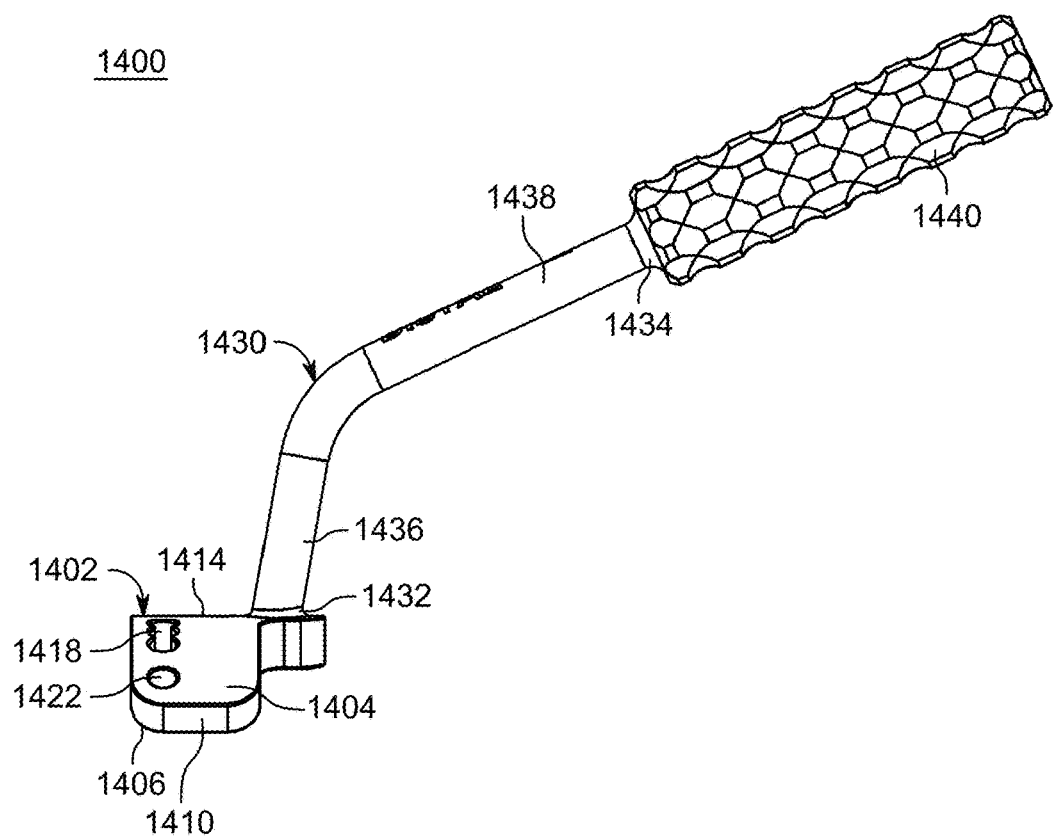
Figure 123:
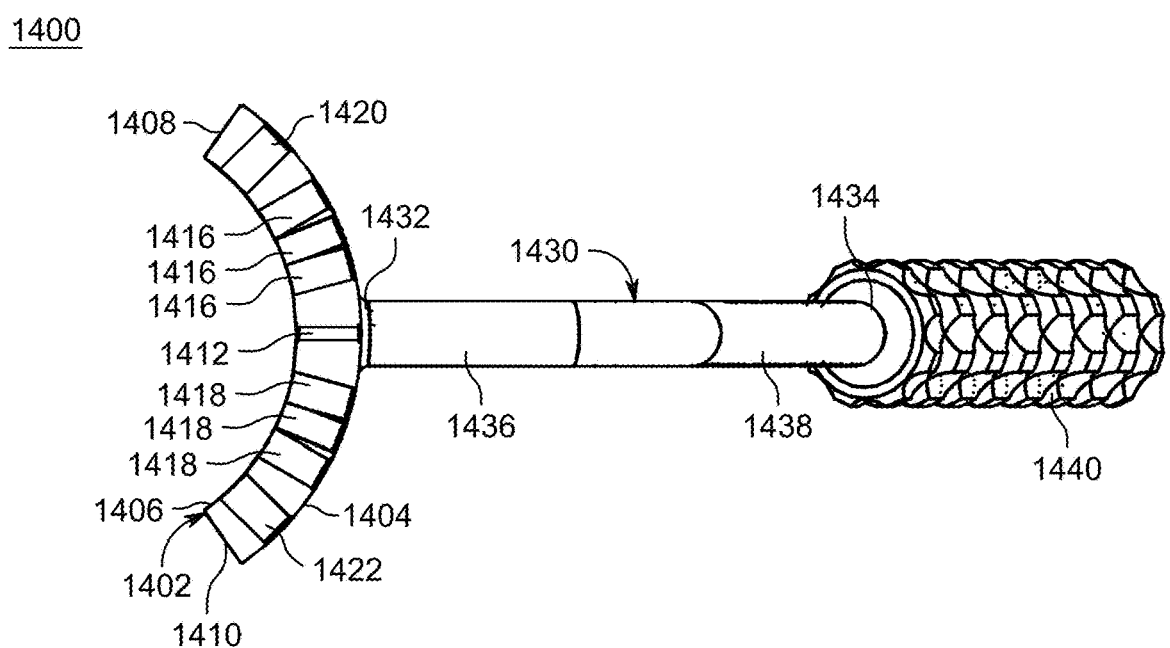

Another position rotation device 1400 is shown in FIGS. 115-123. The rotation device includes a base 1402 with a top surface 1404 opposite a bottom surface 1406, as shown in FIGS. 117, 118 and 123. The base 1402 also includes a first end 1408 opposite a second end 1410. The base 1402 may be, for example, curved to form a semi-circle or arc as the base 1402 extends from the first end 1408 to the second end 1410, as shown in FIGS. 117, 118, and 123. The base 1402 may also optionally include a center alignment groove 1412. The alignment groove 1412 may be inset into a front side of the base 1402 and may extend from the top surface 1404 through the base 1402 to the bottom surface 1406.

With continued reference to FIGS. 115-123, the base 1402 further includes a first or zero opening 1414 positioned, for example, centered between the first end 1408 and the second end 1410 of the base 1402. The zero opening 1414 may be positioned adjacent to the first end 1432 of the shaft 1430. The zero opening 1414 may also be positioned, for example, near a back side of the base 1402. The zero opening 1414 may have, for example, an insertion angle for a guide wire, k-wire or the like of 0° as the opening 1414 extends from the top surface 1404 to the bottom surface 1406. The zero opening 1414 may be used for positioning and aligning the position rotation device 1400 on a patient. The zero opening 1414 may be, for example, sized and shaped or configured to receive a guide wire, k-wire or the like, for aligning the rotation device 1400 on a patient's bone.

As shown in FIGS. 115, 116, 119, 120 and 123, the base 1402 may also include a first set of overlapping openings 1416. The openings 1416 may be positioned along the front side of the rotation device 1400 between the groove 1412 and the first end 1408. The base 1402 may also include a second set of overlapping openings 1418. The openings 1418 may be positioned along the front side of the rotation device 1400 between the groove 1412 and the second end 1410. The base 1402 may also include a third opening 1420 positioned along the front side of the rotation device 1400 between the first set of openings 1416 and the first end 1408. The base 1402 may also include a fourth opening 1422 positioned along the front side of the rotation device 1400 between the second set of openings 1418 and the second end 1410. The openings 1416, 1418, 1420, 1422 may be, for example, angled as they extend from the top surface 1404 to the bottom surface 1406. The first set of overlapping openings 1416 and the second set of overlapping openings 1418 may each include, for example, three openings. The three overlapping openings 1416, 1418 may each have an angle of rotation relative to the zero opening 1414, for example, the openings 1416, 1418 closest to the groove 1412 may have a rotation angle of approximately 10° to 19°. The next openings 1416, 1418 may have a rotation angle of, for example, approximately 20° to 29° and the outer most opening 1416, 1418 from the groove 1412 may have a rotation angle of, for example, approximately 30° to 39°. Finally, the third and fourth openings 1420, 1422 may have rotation angles relative to the zero opening 1414 of, for example, approximately 40° to 50°. In one embodiment, the rotation angles may be, for example, 15°, 25°, 35°, and 45°. In yet another embodiment, the rotation angles may be, for example, 15°, 22°, 30°, and 45°. The openings 1414, 1416, 1420, 1422 may be positioned linearly along the base 1402 as it curves from the first end 1408 to the second end 1410 and offset from the zero opening 1414. Alternatively, each of the openings 1416, 1418, 1420, 1422 may be, for example, offset from each other and the zero opening 1414.

With continued reference to FIGS. 115-123, the shaft 1430 may include a first end 1432 and a second end 1434. The first end 1432 may be coupled to the top surface 1404 of the base 1402 near a center point of the base 1402. The second end 1434 may be coupled to a handle 1440. The shaft 1430 may include a first segment 1436 near the first end 1432 and a second segment 1438 near the second end 1434. As shown in FIGS. 121 and 122, the first segment 1436 may be angled relative to the second segment 1438.

Figure 124:
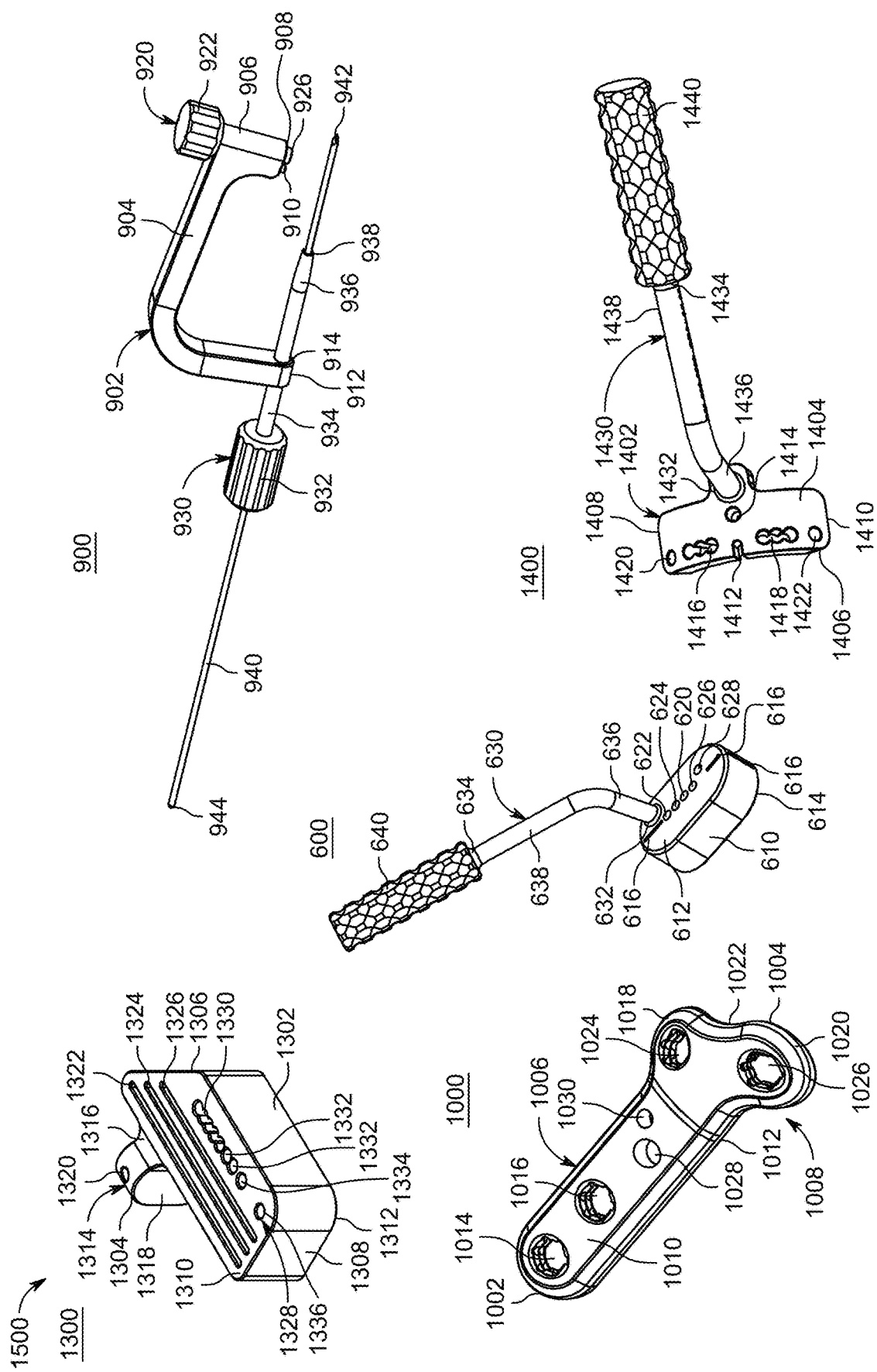

Referring now to FIG. 124, a system 1500 is shown. The system 1500 may include at least one of an alignment device 100, 150, 600, an alignment guide 900, a plate 500, 550, 1000, a cut guide 200, 700, 1300, and a position rotation device 300, 350, 800, 1400. As depicted, in one embodiment the system includes, for example, an alignment device 600, an alignment guide 900, a plate 1000, a cut guide 1300, and a position rotation device 1400. The system may include any combination of the alignment devices 100, 150, 600, alignment guides 900, plates 500, 550, 1000, cut guides 200, 700, 1300, and a position rotation devices 300, 350, 800, 1400 as would be understood by one of ordinary skill in the art.

As may be recognized by those of ordinary skill in the art based on the teachings herein, numerous changes and modifications may be made to the above-described and other embodiments of the present disclosure without departing from the scope of the disclosure. The alignment devices, cut guides, position rotation devices, plates, and other components of the devices, implants, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices, implants and systems may include more or fewer components or features than the embodiments as described and illustrated herein. For example, the components and features of the alignment devices of FIGS. 1-9, FIGS. 10-16, and FIGS. 59-65 may all be used interchangeably and in alternative combinations as would be modified or altered by one of skill in the art. Also, the components and features of the cut guides of FIGS. 17-22, FIGS. 66-71, and FIGS. 107-114 may all be used interchangeably and in alternative combinations as would be modified or altered by one of skill in the art. In addition, the components and features of the position rotation devices of FIGS. 23-28, FIGS. 29-34, FIGS. 72-77, and FIGS. 115-123 may all be used interchangeably and in alternative combinations as would be modified or altered by one of skill in the art. The components and features of the plates of FIGS. 35-41, FIGS. 42-48, and FIGS. 81-87 may all be used interchangeably and in alternative combinations as would be modified or altered by one of skill in the art. Further, the components and features of the systems disclosed herein and including any combination of the alignment devices of FIGS. 1-9, FIGS. 10-16, and FIGS. 59-65, the cut guides of FIGS. 17-22, FIGS. 66-71, and FIGS. 107-114, the position rotation devices of FIGS. 23-28, FIGS. 29-34, FIGS. 72-77, and FIGS. 115-123, the plates of FIGS. 35-41, FIGS. 42-48, and FIGS. 81-87, and the alignment guide of FIGS. 78-80 may all be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A position rotation device, comprising:
    a base, comprising:
        a first surface;
        a second surface opposite the first surface;
        a first end; and
        a second end opposite the first end;
        wherein the base is curved between the first end and the second end;
    an alignment groove extending through the base from the first surface to the second surface, and wherein the alignment groove extends into the base from a first side;
    a shaft coupled to and extending away from the first surface of the base, wherein the shaft has a first portion extending from the base to an intermediate point and a second portion extending from the intermediate point to a handle, and wherein the second portion is positioned at an obtuse angle to the first portion; and
    at least one opening positioned between the alignment groove and at least one of the first end and the second end, wherein the at least one opening comprises:
        at least one first opening positioned between the alignment groove and the first end, wherein the at least one first opening is a plurality of first openings, comprising:
            a first set of overlapping openings; and
            a third opening spaced apart from the first set of overlapping openings;
        at least one second opening positioned between the alignment groove and the second end, wherein the at least one second opening is a plurality of second openings, comprising:
            a second set of overlapping openings; and
            a fourth opening spaced apart from the second set of overlapping openings; and
        at least one alignment opening extending through the base from the first surface to the second surface, and wherein the at least one alignment opening is positioned adjacent to and spaced apart from the alignment groove.

2. The position rotation device of claim 1, wherein the alignment groove is inset into the first side.

3. The position rotation device of claim 1, wherein the position rotation device further comprises a zero opening, wherein the zero opening is centered between the first end and the second end.

4. The position rotation device of claim 3, wherein the zero opening is sized to receive at least one of a guide wire, a trocar and a k-wire.

5. The position rotation device of claim 3, wherein the zero opening has an insertion angle of zero degrees as the zero opening extends between the first surface and the second surface.

6. The position rotation device of claim 1, wherein the at least one first opening is positioned along the first side.

7. The position rotation device of claim 1, wherein the at least one second opening is positioned along the first side.

8. The position rotation device of claim 1, wherein the at least one first opening extends through the base from the first surface to the second surface.

9. The position rotation device of claim 1, wherein the at least one second opening extends through the base from the first surface to the second surface.

10. The position rotation device of claim 1, wherein the first set of overlapping openings comprises three openings.

11. The position rotation device of claim 10, wherein the second set of overlapping openings comprises three openings.

12. The position rotation device of claim 10, wherein each of the three openings of the first set of overlapping openings is angled as each of the three openings extend from the first surface to the second surface.

13. The position rotation device of claim 10, wherein each of the three openings of the second set of overlapping openings is angled as each of the three openings extend from the first surface to the second surface.

14. The position rotation device of claim 12, wherein the angles of rotation for each of the three openings of the first set of overlapping openings are different from each other and range from 10 degrees to 39 degrees.

15. The position rotation device of claim 13, wherein the angles of rotation for each of the three openings of the second set of overlapping openings are different from each other and range from 10 degrees to 39 degrees.

16. The position rotation device of claim 1, wherein the third opening is angled as it extends from the first surface to the second surface forming an angle, wherein the angle ranges between 10 degrees to 50 degrees, and wherein the fourth opening is angled as it extends from the first surface to the second surface, and wherein the angle ranges between 10 degrees to 50 degrees.

17. A position rotation device, comprising:
- a base, comprising:
  - a first surface;
  - a second surface opposite the first surface;
  - a first end; and
  - a second end opposite the first end;
  - wherein the base is curved between the first end and the second end to correspond with a curve of a metatarsal;
- an alignment groove extending through the base from the first surface to the second surface, and wherein the alignment groove extends into the base from a first side;
- a first opening positioned between the first end and the second end of the base; and
- at least one opening positioned between the first opening and at least one of the first end and the second end, wherein the at least one opening corresponds to at least one angle of rotation relative to the first opening.

18. A position rotation device, comprising:
- a base, comprising:
  - a first surface;
  - a second surface opposite the first surface;
  - a first end; and
  - a second end opposite the first end;
  - wherein the base is curved between the first end and the second end to correspond with a curve of a metatarsal;
- an alignment groove extending through the base from the first surface to the second surface, and wherein the alignment groove extends into the base from a first side;
- a shaft coupled to and extending away from the first surface of the base, wherein the shaft has a first portion extending from the base to an intermediate point and a second portion extending from the intermediate point to a handle, and wherein the second portion is positioned at an obtuse angled to the first portion;
- a first opening positioned between the first end and the second end of the base; and
- at least one opening positioned between the first opening and at least one of the first end and the second end.

* * * * *

UNITED STATES PATENT AND TRADEMARK OFFICE
CERTIFICATE OF CORRECTION

PATENT NO. : 11,642,142 B2
APPLICATION NO. : 16/841317
DATED : May 9, 2023
INVENTOR(S) : Wagner et al.

It is certified that error appears in the above-identified patent and that said Letters Patent is hereby corrected as shown below:

In the Claims

Column 32, Line 49: Claim 11, Delete "claim 10" and insert -- claim 1 --

Signed and Sealed this
Thirteenth Day of June, 2023

Katherine Kelly Vidal
*Director of the United States Patent and Trademark Office*